United States Patent
Deretic et al.

(10) Patent No.: US 11,878,018 B1
(45) Date of Patent: Jan. 23, 2024

(54) PHOSPHORYLATION OF SYNTAXIN 17 BY TBK1 CONTROLS AUTOPHAGY INITIATION

(71) Applicant: UNM RAINFOREST INNOVATIONS, Albuquerque, NM (US)

(72) Inventors: Vojo P. Deretic, Placitas, NM (US); Suresh Kumar, Kanpur (IN)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 0 days.

(21) Appl. No.: 16/721,502

(22) Filed: Dec. 19, 2019

Related U.S. Application Data

(60) Provisional application No. 62/782,696, filed on Dec. 20, 2018, provisional application No. 62/806,197, filed on Feb. 15, 2019.

(51) Int. Cl.
| | |
|---|---|
| *A61K 31/5377* | (2006.01) |
| *A61K 31/506* | (2006.01) |
| *A61P 35/00* | (2006.01) |
| *A61K 45/06* | (2006.01) |

(52) U.S. Cl.
CPC ........ *A61K 31/5377* (2013.01); *A61K 31/506* (2013.01); *A61K 45/06* (2013.01); *A61P 35/00* (2018.01)

(58) Field of Classification Search
None
See application file for complete search history.

(56) References Cited

U.S. PATENT DOCUMENTS 8,569,294 B2 * 10/2013 Fukunaga ............... A61P 25/18
544/320

FOREIGN PATENT DOCUMENTS

WO  WO 2011/070150 A1 * 6/2011 ............. C07K 14/82

OTHER PUBLICATIONS

Cruz et al., Journal of Cell Commuication and Signalling (2018), 12, pp. 83-90.*

* cited by examiner

*Primary Examiner* — Brian J Davis
(74) *Attorney, Agent, or Firm* — Henry D. Coleman; R. Neil Sudol

(57) ABSTRACT

The present invention relates to discovery that TBK1 phosphorylates Syntaxin 17 and that phosphorylation of Syntaxin 17 is intimate to control autophagy initiation. The present invention is directed to this discovery and the use of TBK1 inhibitors or inhibitors of Syntaxin 17 phosphorylation alone or in combination with additional bioactive agents to inhibit autophagy in the treatment of disease, especially the treatment of cancers. Methods of treating various cancers are disclosed using TBK1 inhibitors to patients with cancer and into cancerous tissues for the treatment of cancer including the inhibition, amelioration, reduction in metastasis and in recurrence of cancer in remission. Assays and methods for identifying compounds as inhibitors of Syntaxin 17 and as potential therapeutic agents for cancer and autoimmune diseases are also diseased herein.

20 Claims, 30 Drawing Sheets

Specification includes a Sequence Listing.

FIGURE 2
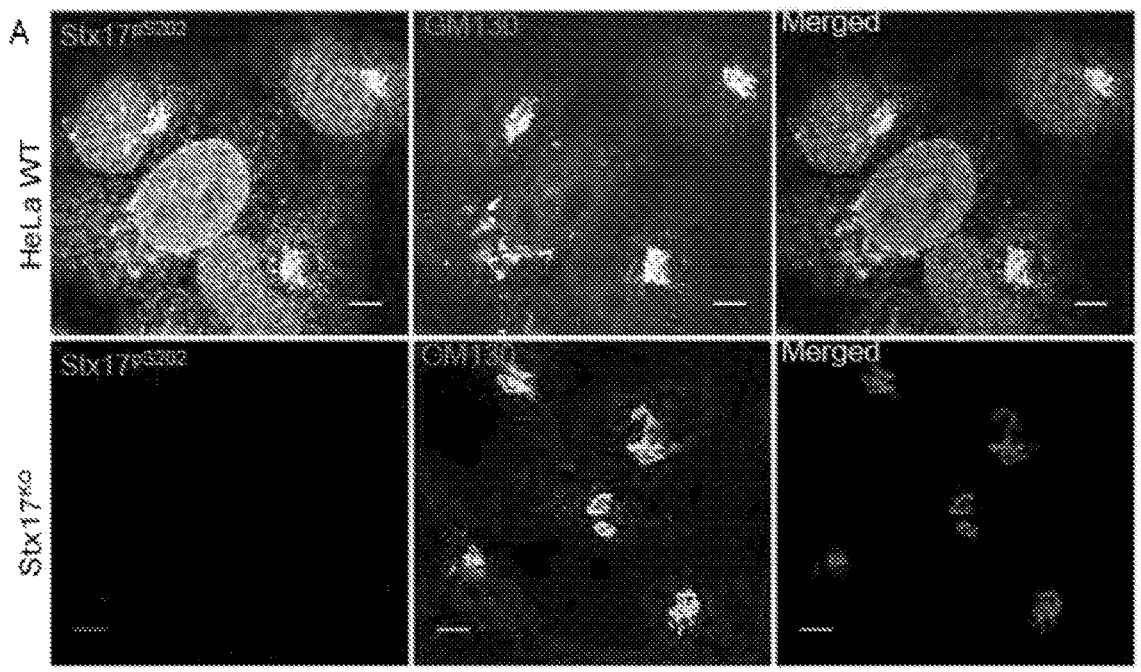
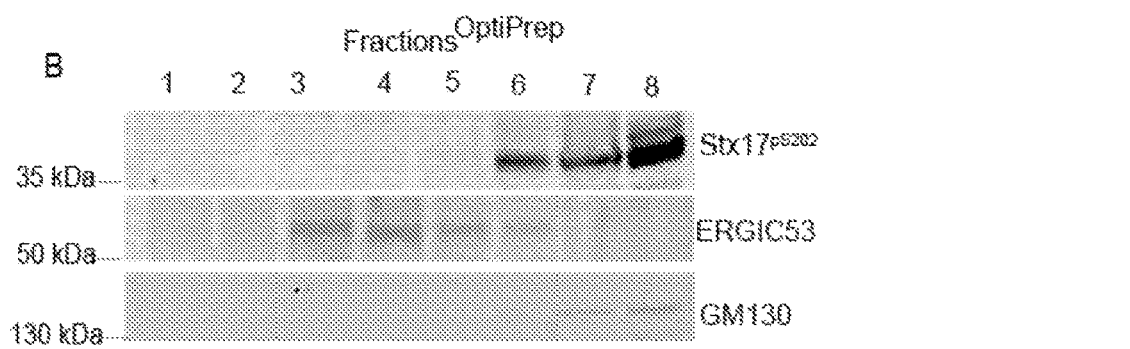
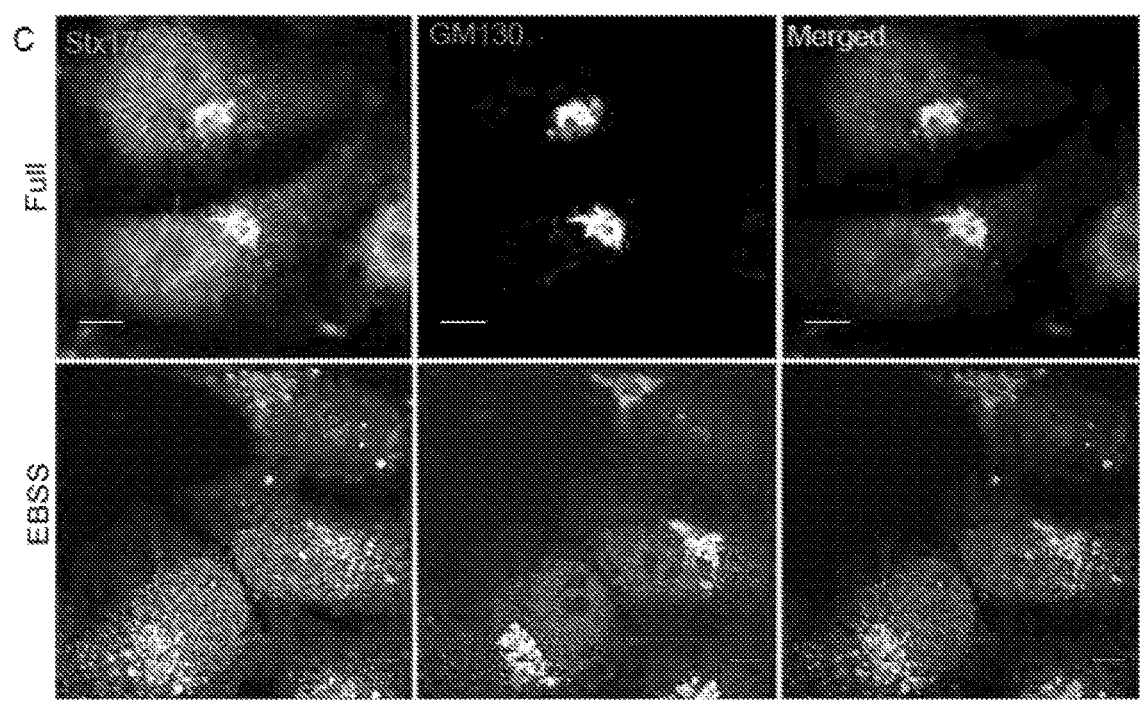

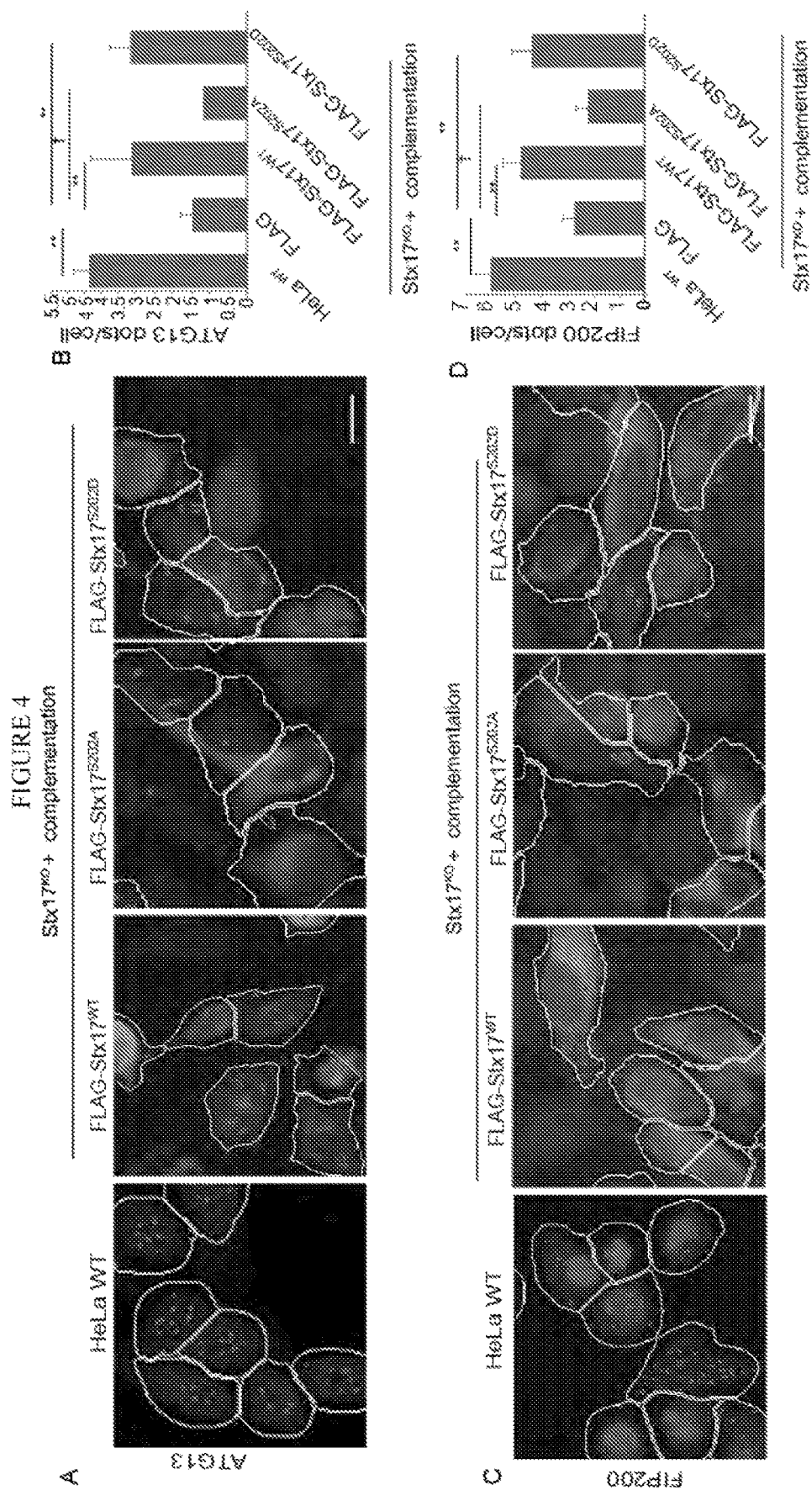

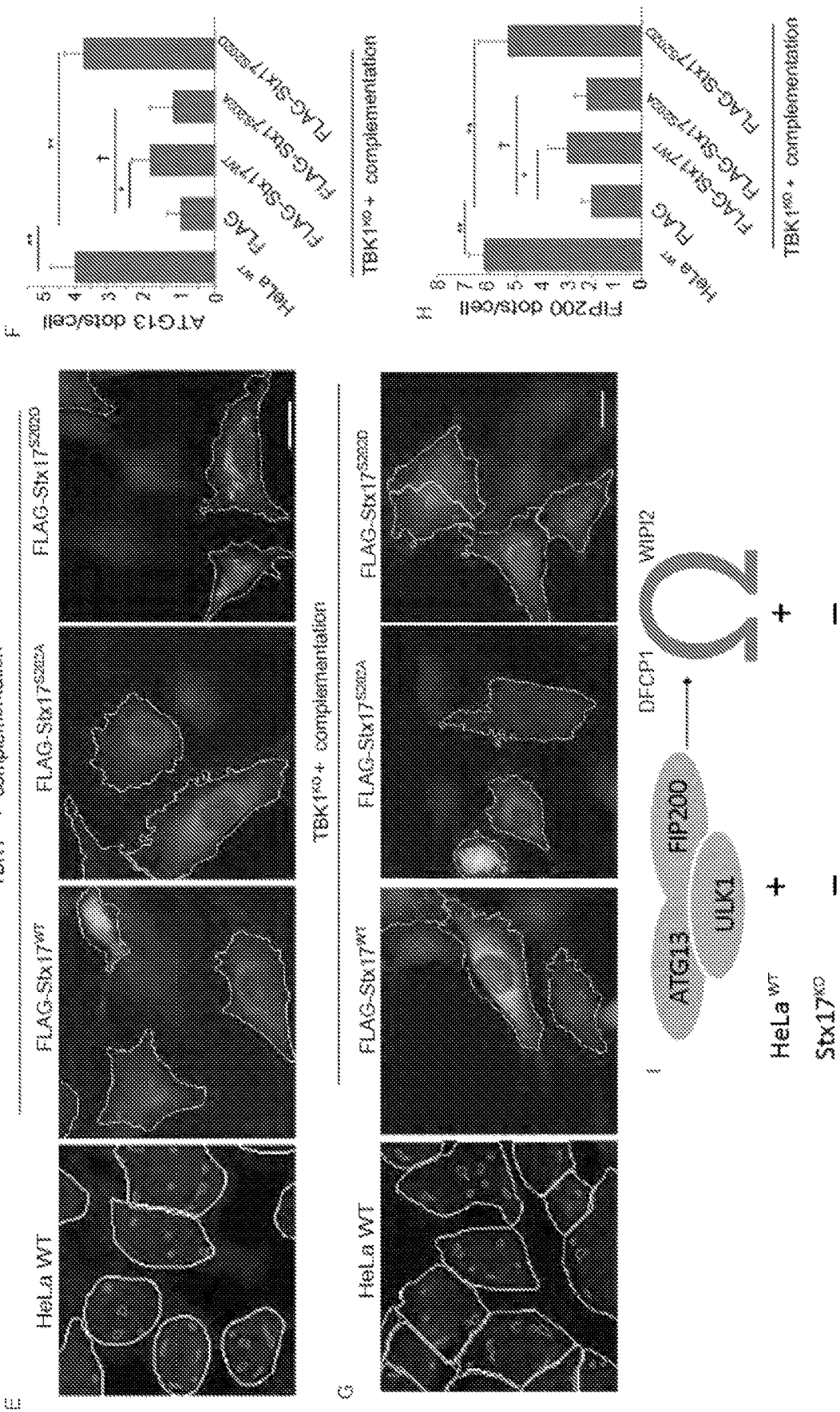

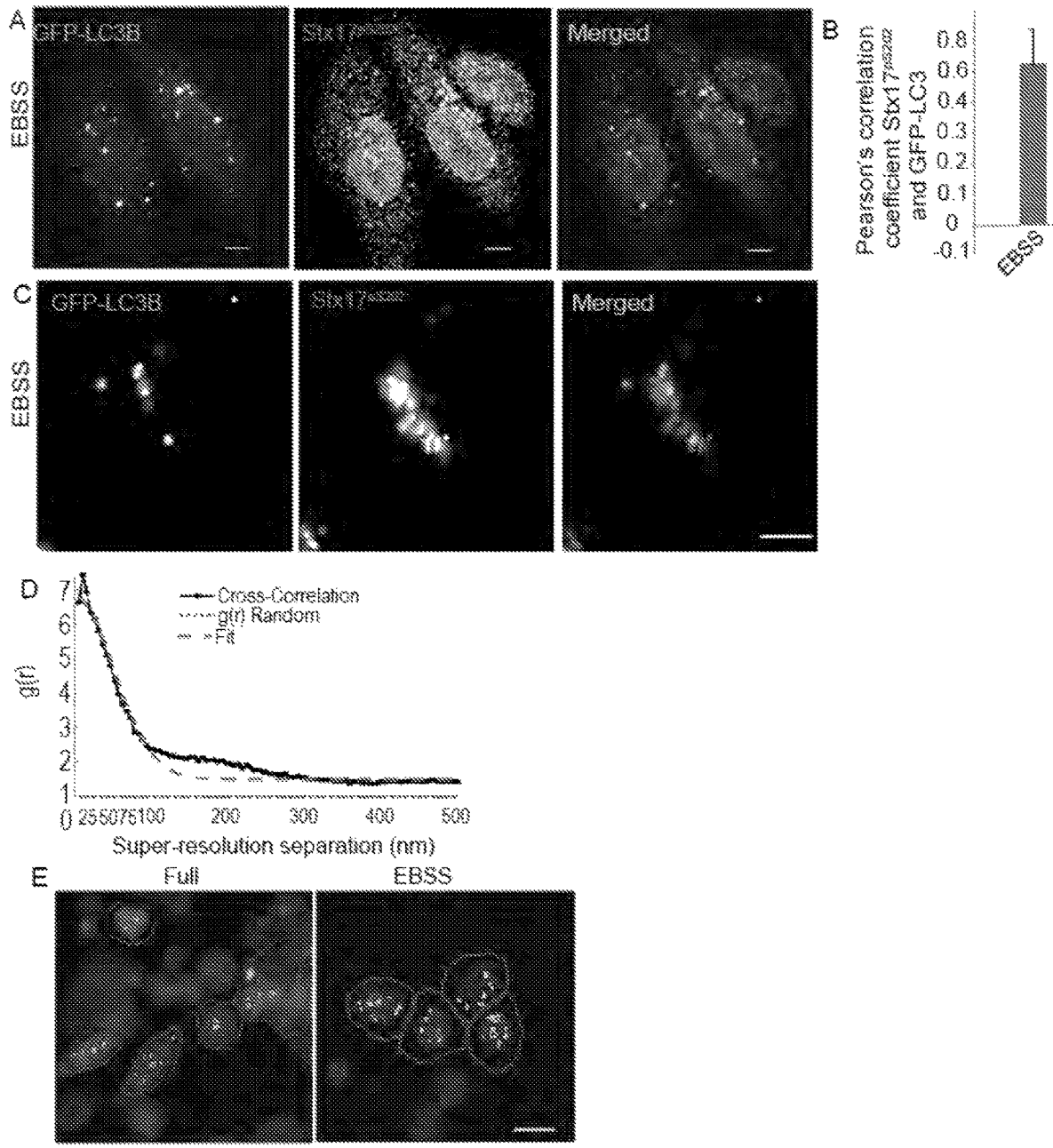

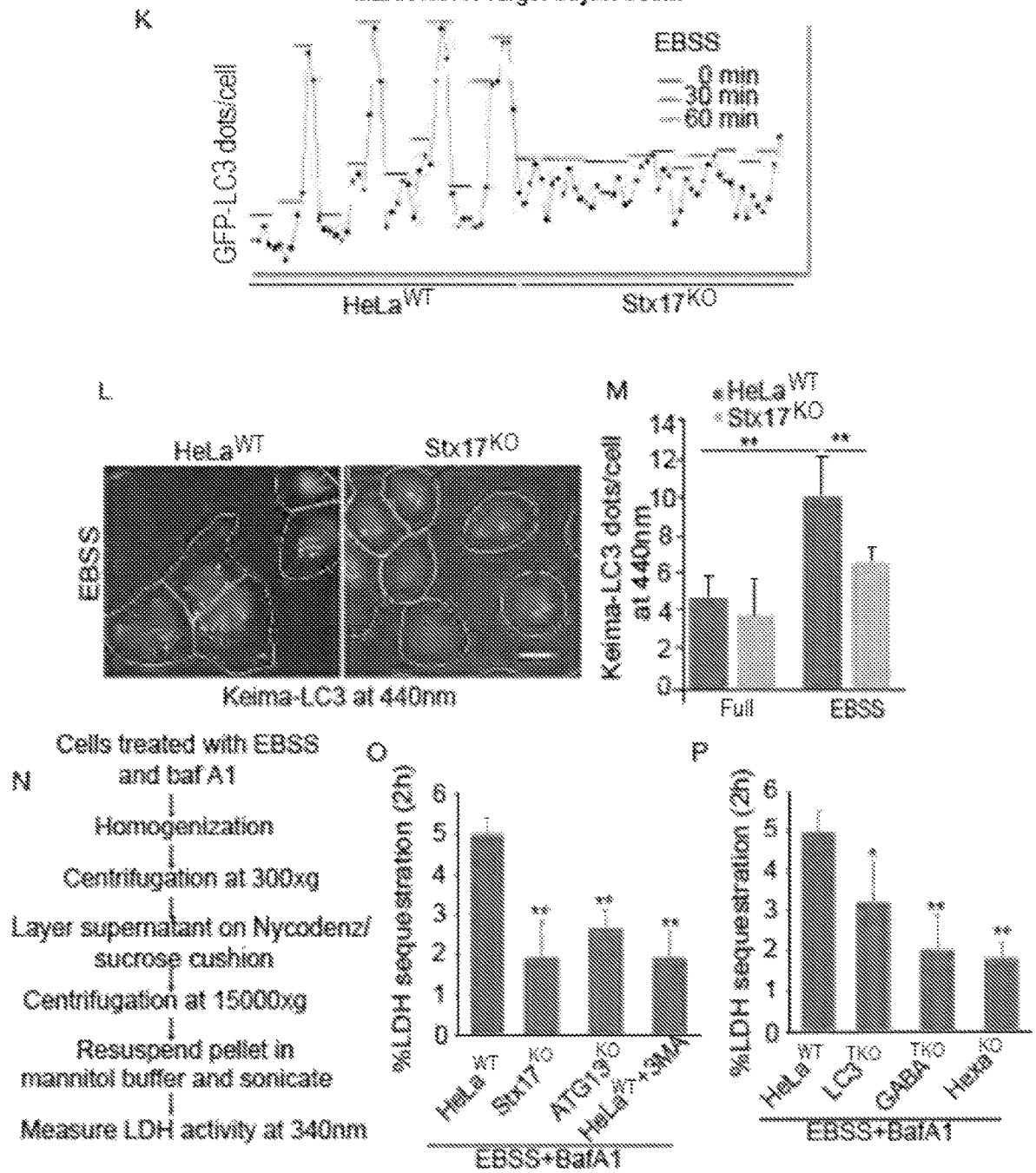

FIGURE 7 (cont'd)
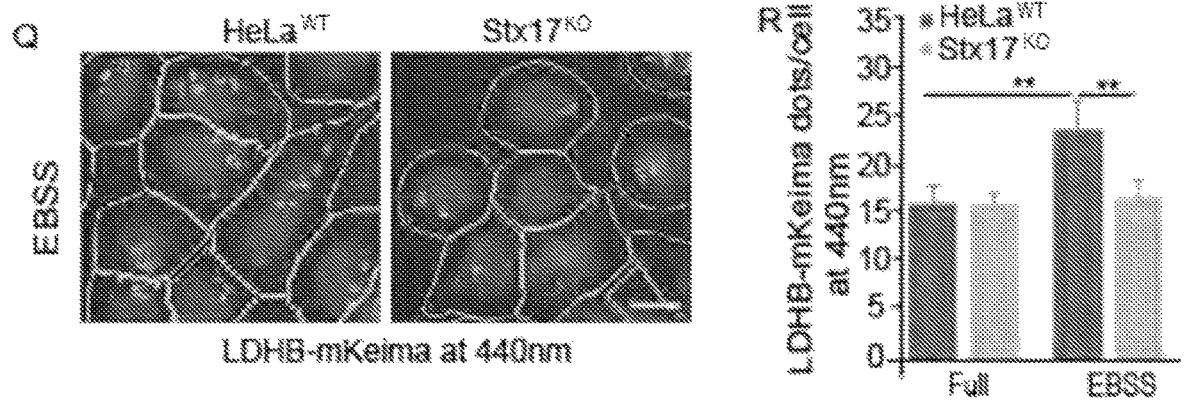
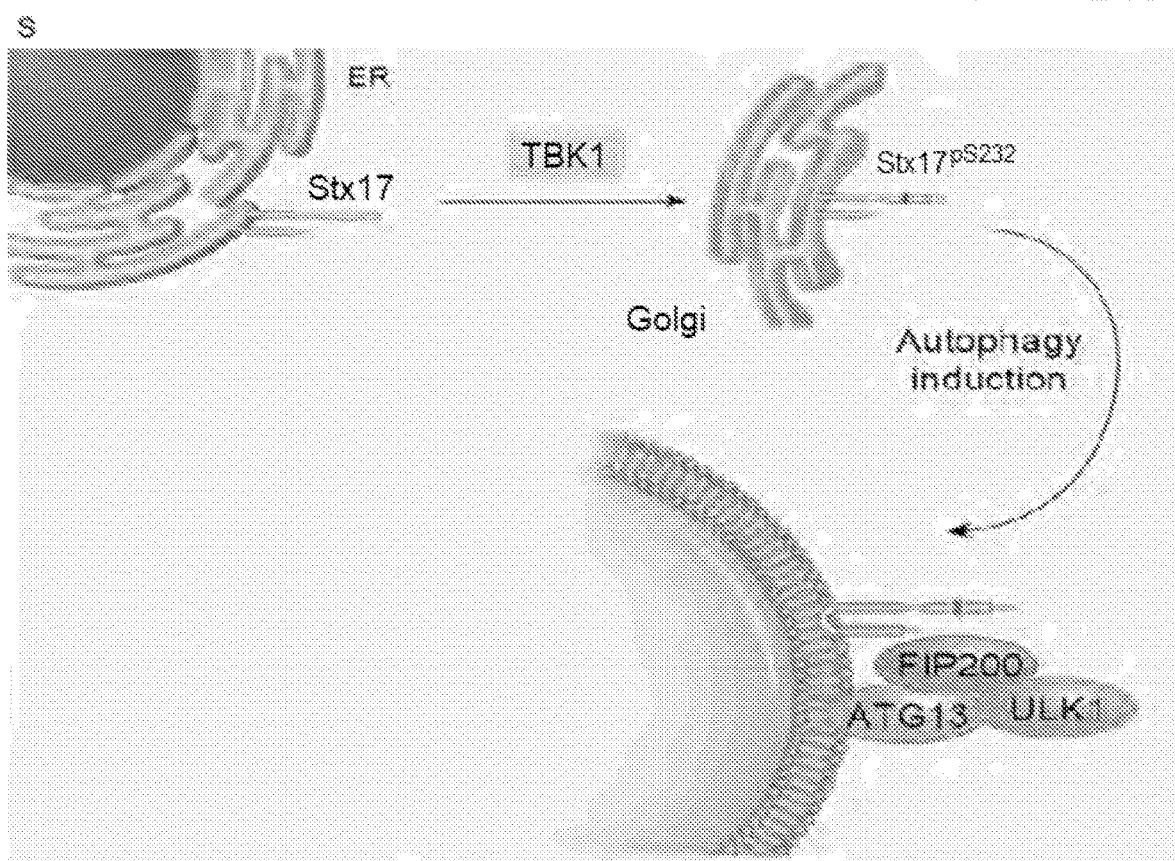

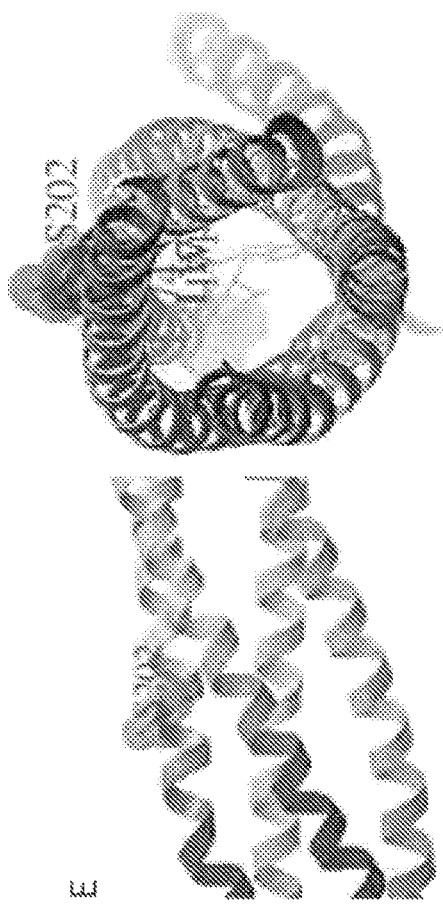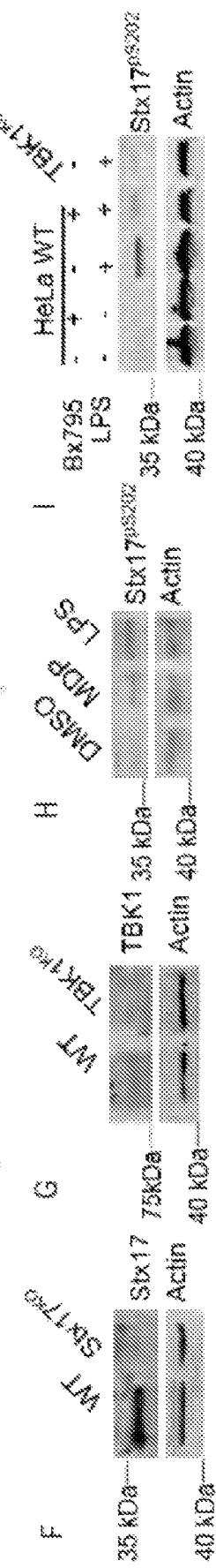

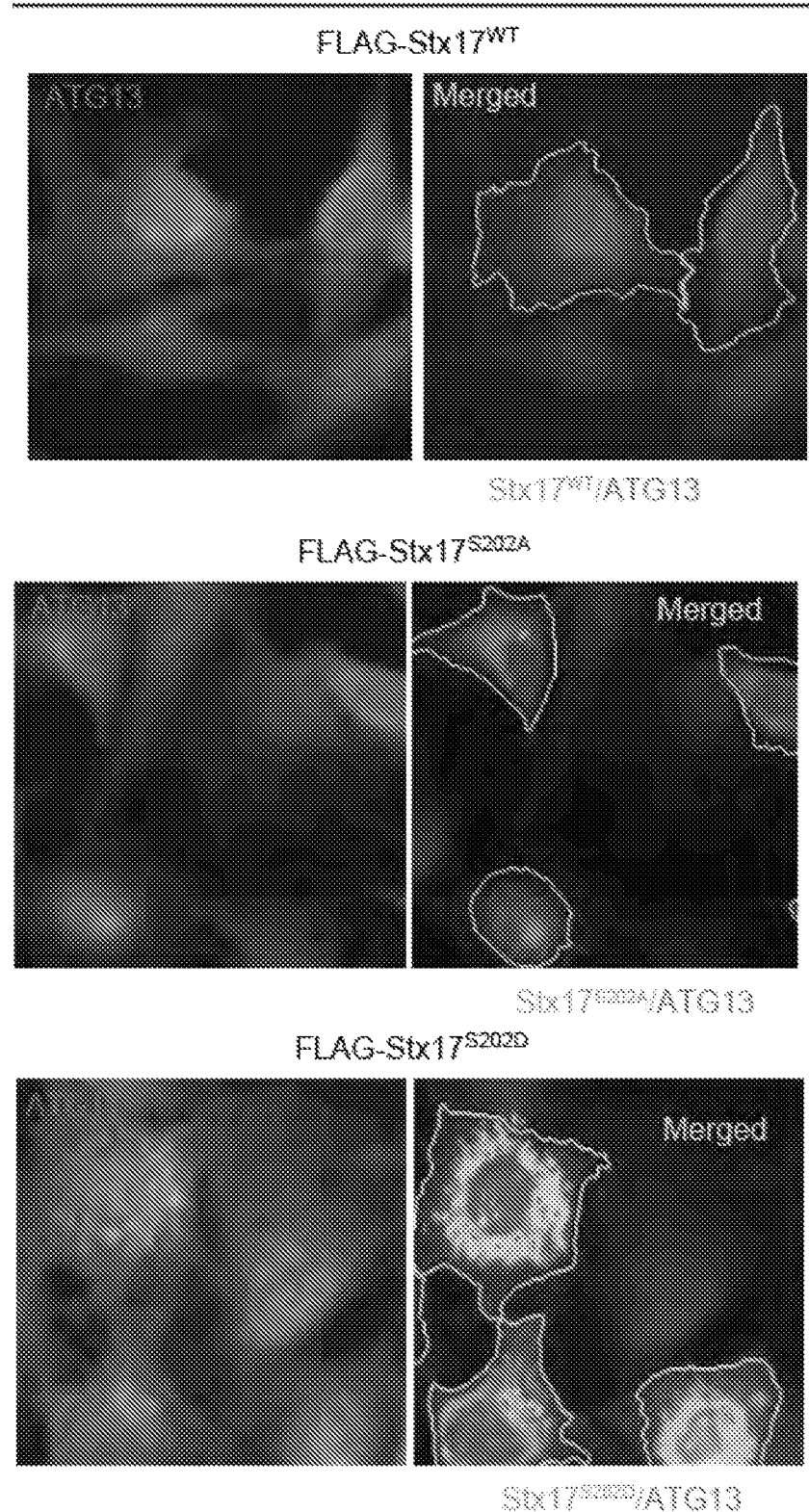

FIGURE 11 (cont'd)
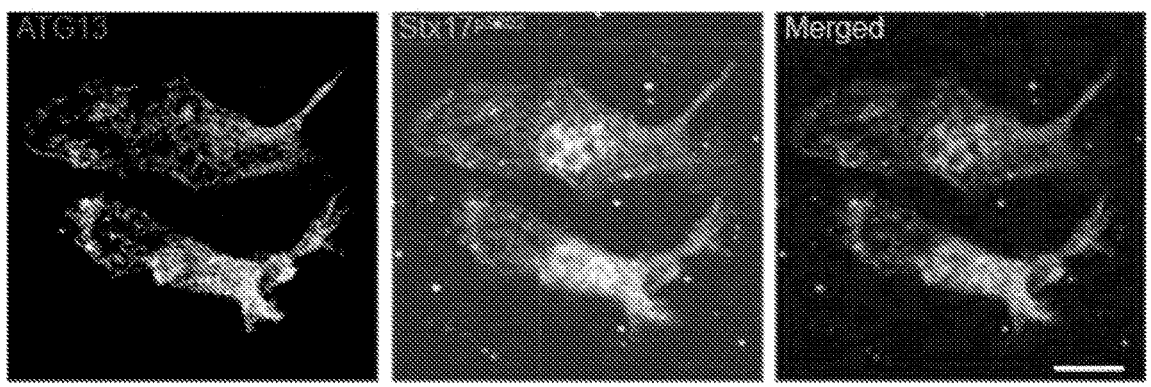
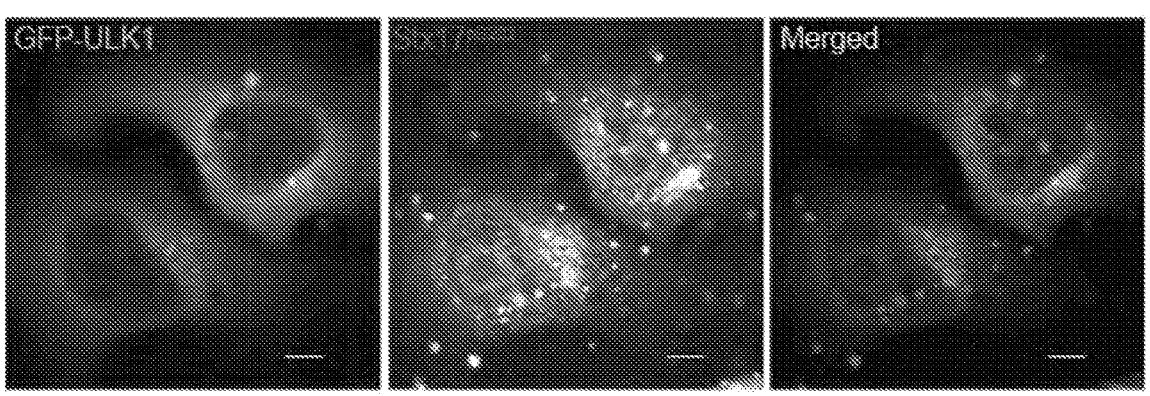
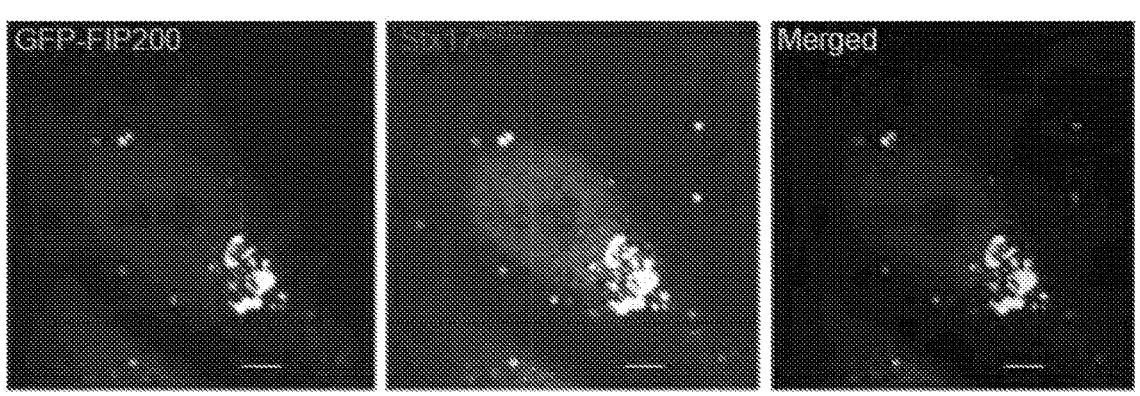

SEQUENCE LISTING

<160> NUMBER OF SEQ ID NOS: 10

<210> SEQ ID NO 1
<211> LENGTH: 302
<212> TYPE: PRT
<213> ORGANISM: Homo sapiens

<400> SEQUENCE: 1

Met Ser Glu Asp Glu Glu Lys Val Lys Leu Arg Arg Leu Glu Pro Ala
1               5                   10                  15

Ile Gln Lys Phe Ile Lys Ile Val Ile Pro Thr Asp Leu Glu Arg Leu
            20                  25                  30

-continued

Arg Lys His Gln Ile Asn Ile Glu Lys Tyr Gln Arg Cys Arg Ile Trp
        35                  40                  45

Asp Lys Leu His Glu Glu His Ile Asn Ala Gly Arg Thr Val Gln Gln
        50                  55                  60

Leu Arg Ser Asn Ile Arg Glu Ile Glu Lys Leu Cys Leu Lys Val Arg
65                  70                  75                  80

Lys Asp Asp Leu Val Leu Leu Lys Arg Met Ile Asp Pro Val Lys Glu
                    85                  90                  95

Glu Ala Ser Ala Ala Thr Ala Glu Phe Leu Gln Leu His Leu Glu Ser
                100                 105                 110

Val Glu Glu Leu Lys Lys Gln Phe Asn Asp Glu Thr Leu Leu Gln
                115                 120                 125

Pro Pro Leu Thr Arg Ser Met Thr Val Gly Gly Ala Phe His Thr Thr
    130                 135                 140

Glu Ala Glu Ala Ser Ser Gln Ser Leu Thr Gln Ile Tyr Ala Leu Pro
145                 150                 155                 160

Glu Ile Pro Gln Asp Gln Asn Ala Ala Glu Ser Trp Glu Thr Leu Glu
                165                 170                 175

Ala Asp Leu Ile Glu Leu Ser Gln Leu Val Thr Asp Phe Ser Leu Leu
                180                 185                 190

Val Asn Ser Gln Gln Glu Lys Ile Asp Ser Ile Ala Asp His Val Asn
                195                 200                 205

Ser Ala Ala Val Asn Val Glu Glu Gly Thr Lys Asn Leu Gly Lys Ala
    210                 215                 220

Ala Lys Tyr Lys Leu Ala Ala Leu Pro Val Ala Gly Ala Leu Ile Gly
225                 230                 235                 240

Gly Met Val Gly Gly Pro Ile Gly Leu Leu Ala Gly Phe Lys Val Ala
                245                 250                 255

Gly Ile Ala Ala Ala Leu Gly Gly Gly Val Leu Gly Phe Thr Gly Gly
                260                 265                 270

Lys Leu Ile Gln Arg Lys Lys Gln Lys Met Met Glu Lys Leu Thr Ser
                275                 280                 285

Ser Cys Pro Asp Leu Pro Ser Gln Thr Asp Lys Lys Cys Ser
    290                 295                 300

<210> SEQ ID NO 2
<211> LENGTH: 38
<212> TYPE: PRT
<213> ORGANISM: Homo sapiens

<400> SEQUENCE: 2

Glu Leu Ser Gln Leu Val Thr Asp Phe Ser Leu Leu Val Asn Ser Gln
1               5                   10                  15

Gln Glu Lys Ile Asp Ser Ile Ala Asp His Val Asn Ser Ala Ala Val
                20                  25                  30

Asn Val Glu Glu Gly Thr
        35

<210> SEQ ID NO 3
<211> LENGTH: 38
<212> TYPE: PRT
<213> ORGANISM: Mus musculus

-continued

<400> SEQUENCE: 3

Glu Leu Ser His Leu Val Thr Asp Met Ser Leu Leu Val Ser Gln
1               5                   10                  15

Gln Glu Lys Ile Asp Ser Ile Ala Asp His Val Asn Ser Ala Ala Val
            20                  25                  30

Asn Val Glu Glu Gly Thr
            35

<210> SEQ ID NO 4
<211> LENGTH: 6
<212> TYPE: PRT
<213> ORGANISM: Homo sapiens

<400> SEQUENCE: 4

Asp Ser Ile Ala Asp His
1               5

<210> SEQ ID NO 5
<211> LENGTH: 20
<212> TYPE: DNA
<213> ORGANISM: Homo sapiens

<400> SEQUENCE: 5
gatagtaatc ccaacagacc                                          20

<210> SEQ ID NO 6
<211> LENGTH: 20
<212> TYPE: DNA
<213> ORGANISM: Homo sapiens

<400> SEQUENCE: 6
tcaccctagt tatagcaaga                                          20

<210> SEQ ID NO 7
<211> LENGTH: 20
<212> TYPE: DNA
<213> ORGANISM: Homo sapiens

<400> SEQUENCE: 7
gatgaagatc aacctggaag                                          20

<210> SEQ ID NO 8
<211> LENGTH: 20
<212> TYPE: PRT
<213> ORGANISM: Homo sapiens

<400> SEQUENCE: 8

Ile Asp Ser Ile Ala Asp His Val Asn Ser Ala Ala Val Asn Val Glu
1               5                   10                  15

Glu Gly Thr Lys
            20

<210> SEQ ID NO 9
<211> LENGTH: 729
<212> TYPE: PRT
<213> ORGANISM: Homo sapiens

<400> SEQUENCE: 9

Met Gln Ser Thr Ser Asn His Leu Trp Leu Leu Ser Asp Ile Leu Gly
1               5                   10                  15

Gln Gly Ala Thr Ala Asn Val Phe Arg Gly Arg His Lys Lys Thr Gly
            20                  25                  30

```
Asp Leu Phe Ala Ile Lys Val Phe Asn Asn Ile Ser Phe Leu Arg Pro
         35                  40                  45

Val Asp Val Gln Met Arg Glu Phe Glu Val Leu Lys Lys Leu Asn His
 50                  55                  60

Lys Asn Ile Val Lys Leu Phe Ala Ile Glu Glu Thr Thr Thr Arg
 65                  70                  75                  80

His Lys Val Leu Ile Met Glu Phe Cys Pro Cys Gly Ser Leu Tyr Thr
                     85                  90                  95

Val Leu Glu Glu Pro Ser Asn Ala Tyr Gly Leu Pro Ser Glu Phe
                100                 105                 110

Leu Ile Val Leu Arg Asp Val Val Gly Gly Met Asn His Leu Arg Glu
                115                 120                 125

Asn Gly Ile Val His Arg Asp Ile Lys Pro Gly Asn Ile Met Arg Val
130                 135                 140

Ile Gly Glu Asp Gly Gln Ser Val Tyr Lys Leu Thr Asp Phe Gly Ala
145                 150                 155                 160

Ala Arg Glu Leu Glu Asp Asp Glu Gln Phe Val Ser Leu Tyr Gly Thr
                165                 170                 175

Glu Glu Tyr Leu His Pro Asp Met Tyr Glu Arg Ala Val Leu Arg Lys
                180                 185                 190

Asp His Gln Lys Lys Tyr Gly Ala Thr Val Asp Leu Trp Ser Ile Gly
                195                 200                 205

Val Thr Phe Tyr His Ala Ala Thr Gly Ser Leu Pro Phe Arg Pro Phe
                210                 215                 220

Glu Gly Pro Arg Arg Asn Lys Glu Val Met Tyr Lys Ile Ile Thr Gly
225                 230                 235                 240

Lys Pro Ser Gly Ala Ile Ser Gly Val Gln Lys Ala Glu Asn Gly Pro
                245                 250                 255

Ile Asp Trp Ser Gly Asp Met Pro Val Ser Cys Ser Leu Ser Arg Gly
                260                 265                 270

Leu Gln Val Leu Leu Thr Pro Val Leu Ala Asn Ile Leu Glu Ala Asp
                275                 280                 285

Gln Glu Lys Cys Trp Gly Phe Asp Gln Phe Phe Ala Glu Thr Ser Asp
                290                 295                 300

Ile Leu His Arg Met Val Ile His Val Phe Ser Leu Gln Gln Met Thr
305                 310                 315                 320

Ala His Lys Ile Tyr Ile His Ser Tyr Asn Thr Ala Thr Ile Phe His
                325                 330                 335

Glu Leu Val Tyr Lys Gln Thr Lys Ile Ile Ser Ser Asn Gln Glu Leu
                340                 345                 350

Ile Tyr Glu Gly Arg Arg Leu Val Leu Glu Pro Gly Arg Leu Ala Gln
                355                 360                 365

His Phe Pro Lys Thr Thr Glu Glu Asn Pro Ile Phe Val Val Ser Arg
                370                 375                 380

Glu Pro Leu Asn Thr Ile Gly Leu Ile Tyr Glu Lys Ile Ser Leu Pro
385                 390                 395                 400

Lys Val His Pro Arg Tyr Asp Leu Asp Gly Asp Ala Ser Met Ala Lys
                405                 410                 415

Ala Ile Thr Gly Val Val Cys Tyr Ala Cys Arg Ile Ala Ser Thr Leu
                420                 425                 430

Leu Leu Tyr Gln Glu Leu Met Arg Lys Gly Ile Arg Trp Leu Ile Glu
                435                 440                 445
```

```
Leu Ile Lys Asp Asp Tyr Asn Glu Thr Val His Lys Lys Thr Glu Val
        450                 455                 460

Val Ile Thr Leu Asp Phe Cys Ile Arg Asn Ile Glu Lys Thr Val Lys
465                 470                 475                 480

Val Tyr Glu Lys Leu Met Lys Ile Asn Leu Glu Ala Ala Glu Leu Gly
                485                 490                 495

Glu Ile Ser Asp Ile His Thr Lys Leu Leu Arg Leu Ser Ser Ser Gln
            500                 505                 510

Gly Thr Ile Glu Thr Ser Leu Gln Asp Ile Asp Ser Arg Leu Ser Pro
        515                 520                 525

Gly Gly Ser Leu Ala Asp Ala Trp Ala His Gln Glu Gly Thr His Pro
        530                 535                 540

Lys Asp Arg Asn Val Glu Lys Leu Gln Val Leu Leu Asn Cys Met Thr
545                 550                 555                 560

Glu Ile Tyr Tyr Gln Phe Lys Lys Asp Lys Ala Glu Arg Arg Leu Ala
                565                 570                 575

Tyr Asn Glu Glu Gln Ile His Lys Phe Asp Lys Gln Lys Leu Tyr Tyr
            580                 585                 590

His Ala Thr Lys Ala Met Thr His Phe Thr Asp Glu Cys Val Lys Lys
        595                 600                 605

Tyr Glu Ala Phe Leu Asn Lys Ser Glu Glu Trp Ile Arg Lys Met Leu
        610                 615                 620

His Leu Arg Lys Gln Leu Leu Ser Leu Thr Asn Gln Cys Phe Asp Ile
625                 630                 635                 640

Glu Glu Glu Val Ser Lys Tyr Gln Glu Tyr Thr Asn Glu Leu Gln Glu
                645                 650                 655

Thr Leu Pro Gln Lys Met Phe Thr Ala Ser Ser Gly Ile Lys His Thr
            660                 665                 670

Met Thr Pro Ile Tyr Pro Ser Ser Asn Thr Leu Val Glu Met Thr Leu
        675                 680                 685

Gly Met Lys Lys Leu Lys Glu Glu Met Glu Gly Val Val Lys Glu Leu
        690                 695                 700

Ala Glu Asn Asn His Ile Leu Glu Arg Phe Gly Ser Leu Thr Met Asp
705                 710                 715                 720

Gly Gly Leu Arg Asn Val Asp Cys Leu
                725

<210> SEQ ID NO 10
<211> LENGTH: 38
<212> TYPE: PRT
<213> ORGANISM: Danio rerio

<400> SEQUENCE: 10

Gln Leu Asn Gly Leu Val Asn Glu Phe Ser Thr Ile Val Tyr Ala Gln
1               5                   10                  15

Gln Glu Lys Ile Asp Ser Ile Glu Ala Asn Val Ser Ile Ala Ala Ala
            20                  25                  30

Asn Val Glu Glu Gly Thr
        35
```

PHOSPHORYLATION OF SYNTAXIN 17 BY TBK1 CONTROLS AUTOPHAGY INITIATION

RELATED APPLICATIONS

This application claims the benefit of priority of United States provisional application nos. U.S. 62/782,696, filed 20 Dec. 2018 and U.S. 62/806,197, filed 15 Feb. 2019, each of said applications being incorporated by reference in their entirety herein.

GRANT SUPPORT

This invention was made with government support under grant numbers R37AI042999 and R01AI042999 and center grant number P20GM121176, all awarded by National Institutes of Health (NIH). The government has certain rights in the invention.

FIELD OF THE INVENTION

The present invention relates to discovery that TBK1 phosphorylates Syntaxin 17 and that phosphorylation of Syntaxin 17 is intimate to control autophagy initiation. The present invention is directed to this discovery and the use of TBK1 inhibitors alone or in combination with additional bioactive agents to inhibit autophagy in the treatment of disease, especially the treatment of cancers. Methods of treating various cancers are disclosed using TBK1 inhibitors to patients with cancer and into cancerous tissues for the treatment of cancer including the inhibition, amelioration, reduction in metastasis and in recurrence of cancer in remission.

BACKGROUND AND OVERVIEW OF THE INVENTION

The autophagy pathway controlled by the ATG factors is a cytoplasmic homeostatic process that plays both metabolic and quality control roles and affects a wide range of physiological and pathological conditions. The known components of the autophagy machinery in mammalian cells include several protein complexes. One such complex contains the first autophagy pathway-dedicated protein kinase ULK1, corresponding to Atg1 in yeast (Chan et al., 2007; Mizushima et al., 2011). The ULK1 complex contains additional components, including FIP200 (Hara et al., 2008) and ATG13 (Alers et al., 2014). These and additional proteins are substrates for upstream kinases, mTOR and AMPK, which regulate the activity of the ULK1 complex in response to the classical inducer of autophagy, starvation (Inoki et al., 2012). In yeast, autophagosomes emanate from the well-defined pre-autophagosomal structure (PAS), whereas the definition of its counterpart in mammalian cells has been elusive. The ULK1 complex is often considered to be the putative mammalian equivalent of PAS (Mizushima et al., 2011), referred herein as mPAS.

The definition of the earliest components that define mPAS has been a topic of much interest, with the FIP200 and ATG13 puncta believed to represent the early precursors of autophagosomes in mammalian cells (Alers et al., 2014; Karanasios et al., 2013; Karanasios et al., 2016; Mizushima et al., 2011; Nishimura et al., 2017) and include additional components such as ATG101 (Suzuki et al., 2015). Eventually, this and additional complexes interact physically or functionally (Dooley et al., 2014; Fujita et al., 2013; Gammoh et al., 2013; Hara et al., 2008) with other protein systems, including the conjugation machinery that lipidates mammalian Atg8 proteins (mAtg8s), encompassing the well-known member LC3B (Kabeya et al., 2000) that serves as a marker of the early autophagic organelles such as phagophores/isolation membranes as they progress into closed autophagosomes. At several points along this pathway, the class III PI3K VPS34 contributes to the formation and progression of autophagic membrane intermediates, including the initiation events that transit through a structure known as omegasome, marked by the protein DFCP1 (Axe et al., 2008) that binds PI3P, the product of VPS34 (Baskaran et al., 2014; Petiot et al., 2000). Despite this progress, a number of details and the order of events remain to be defined for early stages in autophagy initiation in mammalian cells.

The degradative autophagy pathway culminates in a fusion of closed autophagosomes, after they complete cargo sequestration, with lysosomal organelles where the cargo is eventually degraded (Mizushima et al., 2011). This process is driven by several SNARE complexes including those containing Ykt6 (Bas et al., 2018; Gao et al., 2018; Matsui et al., 2018; Takats et al., 2018) and Stx17 (Diao et al., 2015; Guo et al., 2014; Itakura et al., 2012; Takats et al., 2013; Wang et al., 2016). Initially, it was thought that Stx17 was the main driver of autophagosome-lysosome fusion, but the latest studies indicate that while it contributes to these events, additional SNARE complexes are required (Bas et al., 2018; Gao et al., 2018; Matsui et al, 2018; Takats et al., 2018). The very early studies with Stx17 have also suggested that it functions in a number of ways, including potentially affecting autophagic initiation at the mitochondria ER contact sites (Arasaki et al., 2018; Arasaki et al., 2015; Hamasaki et al., 2013). However, this concept has not received general support. Another protein kinase, TBK1 (Ahmad et al., 2016), has been implicated in autophagy (Pilli et al., 2012; Thurston et al., 2009; Wild et al., 2011). Some of these studies have focused on interactions between TBK1 and selective autophagy receptors (Thurston et al., 2009; Wild et al., 2011), whereas other studies have suggested a more generalized role in autophagosomal maturation (Pilli et al., 2012) or in trafficking events associated with ATG9 (Saitoh et al., 2009). TBK1 in principle works with a number of adaptors in innate immunity responses such as type I interferon activation (Liu et al., 2015), whereas its interactions with autophagy receptors and regulators expands its repertoire beyond the interferon stimulation.

In the present application, the inventors show that TBK1 interacts with and modulates another autophagy factor, Stx17, beside the known selective autophagy receptors. The interaction of Stx17 and TBK1 is further reflected in phosphorylation of Stx17 by TBK1 and modulation of its function. Surprisingly, these interactions and phosphorylation of Stx17 by TBK1 occur at the earliest stages of autophagy, i.e. at its initiation. We demonstrate that phosphorylation of Stx17 is important for assembly of the ULK1 complex and that it is critical for autophagy initiation. We show that phosphorylated Stx17 and components of the ULK1 complex, localized to the Golgi in the resting state, respond to induction of autophagy by translocating from the Golgi to participate in the formation of mPAS during autophagy initiation.

BRIEF DESCRIPTION OF THE INVENTION

The present invention relates to the discovery that TBK1 phosphorylates Syntaxin 17 and this phosphorylation controls autophagy initiation. Accordingly, it has been discovered that compounds that inhibit TBK1 phosphorylation of Syntaxin 17 are useful in the inhibition of autophagy and in the treatment of cancer and autoimmune disease. In one embodiment, the present invention is directed to the administration of a TBK1 inhibitor and/or an inhibitor of syntaxin 17 phosphorylation such as AG1478 or AG1024 or an anti-STX17 antibody in the treatment of cancer. In another embodiment this method utilizing a TBK1 inhibitor, an inhibitor of syntaxin 17 phosphorylation such as AG1478 or AG1024 and/or an anti-STX17 antibody is useful for the treatment of autoimmune diseases, especially including rheumatoid arthritis, malaria, antiphospholipid antibody syndrome, lupus, chronic urticarial, Sjogren's disease, autoimmune-related Type 1 diabetes, rheumatoid arthritis (RA), psoriasis/psoriatic arthritis, multiple sclerosis, inflammatory bowel disease (IBD) including Crohn's disease and ulcerative colitis, Addison's disease, Grave's disease, Hashimoto's thyroiditis, Myasthenia gravis, autoimmune vasculitis, pernicious anemia and celiac disease, for example. This method comprises administering an effective amount of at least one TBK1 inhibitor to treat and/or reduce the likelihood of a cancer especially including a cancer which may metastasize or a cancer that may recur after remission. In an alternative embodiment, the TBK1 inhibitor most preferably used is BX795 or MRT67307 (from InvivoGen Corporation), but numerous other TBK1 inhibitors may be used including the 2-(Cyclicamino)-pyrimidone derivatives, especially compounds B1-B206, D1-D100, F1-F-160, amlexanox and the compounds listed in columns 249-265 of U.S. Pat. No. 8,569,294, issued Oct. 29, 2013, or a TBK1 inhibitor of LS Application Publication No. 2015/0224089, each of which is incorporated by reference in its entirety herein.

Preferred TBK1 Inhibitors from U.S. Pat. No. 8,569,294 include:
2-(3-Phenylpiperazin-1-yl)-3-methyl-6-(4-pyridyl)-3H-pyrimidin-4-one;
2-(3-(4-Fluorophenyl)piperazin-1-yl)-3-methyl-6-(4-pyridyl)-3H-pyrimidin-4-one;
2-(3-(3-Fluorophenyl)piperazin-1-yl)-3-methyl-6-(4-pyridyl)-3H-pyrimidin-4-one;
2-(3-(2-Fluorophenyl)piperazin-1-yl)-3-methyl-6-(4-pyridyl)-3H-pyrimidin-4-one;
2-(3-(4-Chlorophenyl)piperazin-1-yl)-3-methyl-6-(4-pyridyl)-3H-pyrimidin-4-one;
(S)-2-(3-(4-Chlorophenyl)piperazin-1-yl)-3-methyl-6-(4-pyridyl)-3H-pyrimidin-4-one;
(R)-2-(3-(4-Chlorophenyl)piperazin-1-yl)-3-methyl-6-(4-pyridyl)-3H-pyrimidin-4-one;
2-(3-(3-Chlorophenyl)piperazin-1-yl)-3-methyl-6-(4-pyridyl)-3H-pyrimidin-4-one;
2-(3-(2-Chlorophenyl)piperazin-1-yl)-3-methyl-6-(4-pyridyl)-3H-pyrimidin-4-one;
2-(3-(4-Bromophenyl)piperazin-1-yl)-3-methyl-6-(4-pyridyl)-3H-pyrimidin-4-one;
2(3-(3-Bromophenyl)piperazin-1-yl)-3-methyl-6-(4-pyridyl)-3H-pyrimidin-4-one;
243-(2-Bromophenyl)piperazin-1-yl)-3-methyl-6-(4-pyridyl)-3H-pyrimidin-4-one;
2-(3-(4-Methylphenyl)piperazin-1-yl)-3-methyl-6-(4-pyridyl)-3H-pyrimidin-4-one;
2-(3-(3-Methylphenyl)piperazin-1-yl)-3-methyl-6-(4-pyridyl)-3H-pyrimidin-4-one;
2-(3-(2-Methylphenyl)piperazin-1-yl)-3-methyl-6-(4-pyridyl)-3H-pyrimidin-4-one;
2-(3-(4-Cyanophenyl)piperazin-1-yl)-3-methyl-6-(4-pyridyl)-3H-pyrimidin-4-one;
2-(3-(3-Cyanophenyl)piperazin-1-yl)-3-methyl-6-(4-pyridyl)-3H-pyrimidin-4-one;
2-(3-(2-Cyanophenyl)piperazin-1-yl)-3-methyl-6-(4-pyridyl)-3H-pyrimidin-4-one;
2-(3-(4-Methoxyphenyl)piperazin-1-yl)-3-methyl-6-(4-pyridyl)-3H-pyrimidin-4-one;
2-(3-(3-Methoxyphenyl)piperazin-1-yl)-3-methyl-6-(4-pyridyl)-3H-pyrimidin-4-one;
2-(3-(2-Methoxyphenyl)piperazin-1-yl)-3-methyl-6-(4-pyridyl)-3H-pyrimidin-4-one;
2-(3-(2-Ethoxyphenyl)piperazin-1-yl)-3-methyl-6-(4-pyridyl)-3H-pyrimidin-4-one;
2-(3-(5-Fluoro-2-methoxyphenyl)piperazin-1-yl)-3-methyl-6-(4-pyridyl)-3H-pyrimidin-4-one;
2-(3-(4-Fluoro-3-methoxyphenyl)piperazin-1-yl)-3-methyl-6-(4-pyridyl)-3H-pyrimidin-4-one;
2-(3-(4-Fluoro-2-methoxyphenyl)piperazin-1-yl)-3-methyl-6-(4-pyridyl)-3H-pyrimidin-4-one;
(S)-2-(3-(4-Fluoro-2-methoxyphenyl)piperazin-1-yl)-3-methyl-6-(4-pyridyl)-3H-pyrimidin-4-one;
(R)-2-(3-(4-Fluoro-2-methoxyphenyl)piperazin-1-yl)-3-methyl-6-(4-pyridyl)-3H-pyrimidin-4-one;
2-(3-(4-Chloro-2-methoxyphenyl)piperazin-1-yl)-3-methyl-6-(4-pyridyl)-3H-pyrimidin-4-one;
2-(3-(4-Fluoro-2-methylphenyl)piperazin-1-yl)-3-methyl-6-(4-pyridyl)-3H-pyrimidin-4-one;
2-(3-(2-Fluoro-6-methoxyphenyl)piperazin-1-yl)-3-methyl-6-(4-pyridyl)-3H-pyrimidin-4-one;
2-(3-(5-Bromo-2-methoxyphenyl)piperazin-1-yl)-3-methyl-6-(4-pyridyl)-3H-pyrimidin-4-one;
2-(3-(2-Bromo-4-fluorophenyl)piperazin-1-yl)-3-methyl-6-(4-pyridyl)-3H-pyrimidin-4-one;
2-(3-(2-Chloro-6-fluorophenyl)piperazin-1-yl)-3-methyl-6-(4-pyridyl)-3H-pyrimidin-4-one;
2-(3-(2,4-Difluorophenyl)piperazin-1-yl)-3-methyl-6-(4-pyridyl)-3H-pyrimidin-4-one;
2-(3-(2,6-Difluorophenyl)piperazin-1-yl)-3-methyl-6-(4-pyridyl)-3H-pyrimidin-4-one;
2-(3-(2,6-Dichlorophenyl)piperazin-1-yl)-3-methyl-6-(4-pyridyl)-3H-pyrimidin-4-one;
2-(3-(2,4-Dimethoxyphenyl)piperazin-1-yl)-3-methyl-6-(4-pyridyl)-3H-pyrimidin-4-one;
2-(3-(3,4-Dimethoxyphenyl)piperazin-1-yl)-3-methyl-6-(4-pyridyl)-3H-pyrimidin-4-one;
2-(3-(2,5-Dimethoxyphenyl)piperazin-1-yl)-3-methyl-6-(4-pyridyl)-3H-pyrimidin-4-one;
2-(3-(2,6-Dimethoxyphenyl)piperazin-1-yl)-3-methyl-6-(4-pyridyl)-3H-pyrimidin-4-one;
2-(3-(2,4-Difluoro-6-methoxyphenyl)piperazin-1-yl)-3-methyl-6-(4-pyridyl)-3H-pyrimidin-4-one;
2-(3-(5-Cyano-2-methoxyphenyl)piperazin-1-yl)-3-methyl-6-(4-pyridyl)-3H-pyrimidin-4-one;
2-(3-(4-Cyano-2-methoxyphenyl)piperazin-1-yl)-3-methyl-6-(4-pyridyl)-3H-pyrimidin-4-one;
2-(3-(1-Naphthyl)piperazin-1-yl)-3-methyl-6-(4-pyridyl)-3H-pyrimidin-4-one;
2-(3-(2-Naphthyl)piperazin-1-yl)-3-methyl-6-(4-pyridyl)-3H-pyrimidin-4-one;
2-(3-(2,3-Dihydrobenzofuran-7-yl)piperazin-1-yl)-3-methyl-6-(4-pyridyl)-3H-pyrimidin-4-one;
2-(3-(Benzofuran-2-yl)piperazin-1-yl)-3-methyl-6-(4-pyridyl)-3H-pyrimidin-4-one;
(S)-2(3-(Benzofuran-2-yl)piperazin-1-yl)-3-methyl-6-(4-pyridyl)-3H-pyrimidin-4-one;

2-(3-(4-(Pyrrolidin-1-yl-methyl)phenyl)piperazin-1-yl)-3-methyl-6-(4-pyridyl)-3H-pyrimidin-4-one;
2-(3-(4-(Pyrrolidin-1-yl)phenyl)piperazin-1-yl)-3-methyl-6-(4-pyridyl)-3H-pyrimidin-4-one;
2-(3-(2-methoxy-4-(pyrrolidin-1-yl)phenyl)piperazin-1-yl)-3-methyl-6-(4-pyridyl)-3H-pyrimidin-4-one;
2-(3-(2-methoxy-5-(pyrrolidin-1-yl)phenyl)piperazin-1-yl)-3-methyl-6-(4-pyridyl)-3H-pyrimidin-4-one;
2-(3-(4-(Phenyl)phenyl)piperazin-1-yl)-3-methyl-6-(4-pyridyl)-3H-pyrimidin-4-one;
2-(3-(4-(4-Fluorophenyl)phenyl)piperazin-1-yl)-3-methyl-6-(4-pyridyl)-3H-pyrimidin-4-one;
2-(3-(4-(4-Methoxyphenyl)phenyl)piperazin-1-yl)-3-methyl-6-(4-pyridyl)-3H-pyrimidin-4-one;
2-(3-(4-(2-Methoxyphenyl)phenyl)piperazin-1-yl)-3-methyl-6-(4-pyridyl)-3H-pyrimidin-4-one;
2-(3-(4-(Morpholin-4-yl)phenyl)piperazin-1-yl)-3-methyl-6-(4-pyridyl)-3H-pyrimidin-4-one;
2-(3-(4-(4-Methylpiperazin-1-yl)phenyl)piperazin-1-yl)-3-methyl-6-(4-pyridyl)-3H-pyrimidin-4-one;
2-(4-Phenylpiperazin-1-yl)-3-methyl-6-(4-pyridyl)-3H-pyrimidin-4-one;
2-(4-Benzylpiperazin-1-yl)-3-methyl-6-(4-pyridyl)-3H-pyrimidin-4-one;
2-(4-Benzoylpiperazin-1-yl)-3-methyl-6-(4-pyridyl)-3H-pyrimidin-4-one;
2-(4-(1,2-Benzisothiazol-3-yl)piperazin-1-yl)-3-methyl-6-(4-pyridyl)-3H-pyrimidin-4-one;
2-(4-Methyl-3-phenylpiperazin-1-yl)-3-methyl-6-(4-pyridyl)-3H-pyrimidin-4-one;
2-(3-(4-Fluoro-2-methoxyphenyl)-4-methylpiperazin-1-yl)-3-methyl-6-(4-pyridyl)-3H-pyrimidin-4-one;
(S)-2-(3-(4-Fluoro-2-methoxyphenyl)-4-methylpiperazin-1-yl)-3-methyl-6-(4-pyridyl)-3H-pyrimidin-4-one;
(R)-2-(3-(4-Fluoro-2-methoxyphenyl)-4-methylpiperazin-1-yl)-3-methyl-6-(4-pyridyl)-3H-pyrimidin-4-one;
2-(4-Acetyl-3-(4-fluoro-2-methoxyphenyl)piperazin-1-yl)-3-methyl-6-(4-pyridyl)-3H-pyrimidin-4-one;
2-(4-Benzyl-3-(4-fluoro-2-methoxyphenyl)piperazin-1-yl)-3-methyl-6-(4-pyridyl)-3H-pyrimidin-4-one;
2-(4-Benzyl-3-(ethoxycarbonyl)piperazin-1-yl)-3-methyl-6-(4-pyridyl)-3H-pyrimidin-4-one;
2-(4-methyl-3-(1-naphthyl)piperazin-1-yl)-3-methyl-6-(4-pyridyl)-3H-pyrimidin-4-one;
2-(5,5-Dimethyl-3-(2-methoxyphenyl)piperazin-1-yl)-3-methyl-6-(4-pyridyl)-3H-pyrimidin-4-one;
2-(3-Phenylpiperidin-1-yl)-3-methyl-6-(4-pyridyl)-3H-pyrimidin-4-one;
2-(3-(4-Fluorophenyl)piperidin-1-yl)-3-methyl-6-(4-pyridyl)-3H-pyrimidin-4-one;
2-(3-(3-Fluorophenyl)piperidin-1-yl)-3-methyl-6-(4-pyridyl)-3H-pyrimidin-4-one;
2-(3-(2-Fluorophenyl)piperidin-1-yl)-3-methyl-6-(4-pyridyl)-3H-pyrimidin-4-one;
2-(3-(4-Chlorophenyl)piperidin-1-yl)-3-methyl-6-(4-pyridyl)-3H-pyrimidin-4-one;
2-(3-(4-Bromophenyl)piperidin-1-yl)-3-methyl-6-(4-pyridyl)-3H-pyrimidin-4-one;
2-(3-(4-Methoxyphenyl)piperidin-1-yl)-3-methyl-6-(4-pyridyl)-3H-pyrimidin-4-one;
2-(3(3-Methoxyphenyl)piperidin-1-yl)-3-methyl-6-(4-pyridyl)-3H-pyrimidin-4-one;
2-(3-(2-Methoxyphenyl)piperidin-1-yl)-3-methyl-6-(4-pyridyl)-3H-pyrimidin-4-one;
2-(3-(4-((Pyrrolidin-1-yl)methyl)phenyl)piperidin-1-yl)-3-methyl-6-(4-pyridyl)-3H-pyrimidin-4-one;
(S)-2-(3-(4-(Pyrrolidin-1-yl-methyl)phenyl)piperidin-1-yl)-3-methyl-6-(4-pyridyl)-3H-pyrimidin-4-one;
(R)-2-(3-(4-(Pyrrolidin-1-yl-methyl)phenyl)piperidin-1-yl)-3-methyl-6-(4-pyridyl)-3H-pyrimidin-4-one;
2-(3-Hydroxy-3-phenylpiperidin-1-yl)-3-methyl-6-(4-pyridyl)-3H-pyrimidin-4-one;
2-(3-Phenylpiperazin-1-yl)-3-methyl-6(4-pyrimidyl)-3H-pyrimidin-4-one;
243-(4-Fluorophenyl)piperazin-1-yl)-3-methyl-6-(4-pyrimidyl)-3H-pyrimidin-4-one;
2-(3-(3-Fluorophenyl)piperazin-1-yl)-3-methyl-6-(4-pyrimidyl)-3H-pyrimidin-4-one;
2-(3-(2-Fluorophenyl)piperazin-1-yl)-3-methyl-6-(4-pyrimidyl)-3H-pyrimidin-4-one;
2-(3-(4-Chlorphenyl)piperazin-1-yl)-3-methyl-6-(4-pyrimidyl)-3H-pyrimidin-4-one;
2-(3-(3-Chlorophenyl)piperazin-1-yl)-3-methyl-6-(4-pyrimidyl)-3H-pyrimidin-4-one;
2-(3-(2-Chlorophenyl)piperazin-1-yl)-3-methyl-6-(4-pyrimidyl)-3H-pyrimidin-4-one;
2-(3-(4-Bromophenyl)piperazin-1-yl)-3-methyl-6-(4-pyrimidyl)-3H-pyrimidin-4-one;
2-(3-(3-Bromophenyl)piperazin-1-yl)-3-methyl-6-(4-pyrimidyl)-3H-pyrimidin-4-one;
2-(3-(2-Bromophenyl)piperazin-1-yl)-3-methyl-6-(4-pyrimidyl)-3H-pyrimidin-4-one;
2-(3-(4-Cyanophenyl)piperazin-1-yl)-3-methyl-6-(4-pyrimidyl)-3H-pyrimidin-4-one;
2-(3-(3-Cyanophenyl)piperazin-1-yl)-3-methyl-6-(4-pyrimidyl)-3H-pyrimidin-4-one;
2-(3-(2-Cyanophenyl)piperazin-1-yl)-3-methyl-6-(4-pyrimidyl)-3H-pyrimidin-4-one;
2-(3-(4-Methoxyphenyl)piperazin-1-yl)-3-methyl-6-(4-pyrimidyl)-3H-pyrimidin-4-one;
2-(3-(3-Methoxyphenyl)piperazin-1-yl)-3-methyl-6-(4-pyrimidyl)-3H-pyrimidin-4-one;
2-(3-(2-Methoxyphenyl)piperazin-1-yl)-3-methyl-6-(4-pyrimidyl)-3H-pyrimidin-4-one;
2-(3-(2-Ethoxyphenyl)piperazin-1-yl)-3-methyl-6-(4-pyrimidyl)-3H-pyrimidin-4-one;
2-(3-(6-Fluoro-2-methoxyphenyl)piperazin-1-yl)-3-methyl-6-(4-pyrimidyl)-3H-pyrimidin-4-one;
2-(3-(5-Fluoro-2-methoxyphenyl)piperazin-1-yl)-3-methyl-6-(4-pyrimidyl)-3H-pyrimidin-4-one;
2-(3-(4-Fluoro-2-methoxyphenyl)piperazin-1-yl)-3-methyl-6-(4-pyrimidyl)-3H-pyrimidin-4-one;
(S)-2-(3-(4-Fluoro-2-methoxyphenyl)piperazin-1-yl)-3-methyl-6-(4-pyrimidyl)-3H-pyrimidin-4-one;
(R)-2-(3-(4-Fluoro-2-methoxyphenyl)piperazin-1-yl)-3-methyl-6-(4-pyrimidyl)-3H-pyrimidin-4-one;
2-(3-(4-Chloro-2-methoxyphenyl)piperazin-1-yl)-3-methyl-6-(4-pyrimidyl)-3H-pyrimidin-4-one;
2-(3-(5-Bromo-2-methoxyphenyl)piperazin-1-yl)-3-methyl-6-(4-pyrimidyl)-3H-pyrimidin-4-one;
2-(3-(2,6-Dichlorophenyl)piperazin-1-yl)-3-methyl-6-(4-pyridyl)-3H-pyrimidin-4-one;
2-(3-(2,4-Dimethoxyphenyl)piperazin-1-yl)-3-methyl-6-(4-pyridyl)-3H-pyrimidin-4-one;
2-(3-(3,4-Dimethoxyphenyl)piperazin-1-yl)-3-methyl-6-(4-pyrimidyl)-3H-pyrimidin-4-one;
2-(3-(2,5-Dimethoxyphenyl)piperazin-1-yl)-3-methyl-6-(4-pyrimidyl)-3H-pyrimidin-4-one;
2-(3-(2,6-Dimethoxyphenyl)piperazin-1-yl)-3-methyl-6-(4-pyrimidyl)-3H-pyrimidin-4-one;

2-(3-(2,4-Difluoro-6-methoxyphenyl)piperazin-1-yl)-3-methyl-6-(4-pyrimidyl)-3H-pyrimidin-4-one;
2-(3-(1-Naphthyl)piperazin-1-yl)-3-methyl-6-(4-pyrimidyl)-3H-pyrimidin-4-one;
2-(3-(2-Naphthyl)piperazin-1-yl)-3-methyl-6-(4-pyrimidyl)-3H-pyrimidin-4-one;
2-(3-(2,3-Dihydrobenzofuran-7-yl)piperazin-1-yl)-3-methyl-6-(4-pyrimidyl)-3H-pyrimidin-4-one;
2-(3-(Benzofuran-2-yl)piperazin-1-yl)-3-methyl-6-(4-pyrimidyl)-3H-pyrimidin-4-one;
2-(3-(4-(Pyrrolidin-1-yl-methyl)phenyl)piperazin-1-yl)-3-methyl-6-(4-pyrimidyl)-3H-pyrimidin-4-one;
2-(3-(4-(Pyrrolidin-1-yl)phenyl)piperazin-1-yl)-3-methyl-6-(4-pyrimidyl)-3H pyrimidin-4-one;
2-(3-(2-methoxy-4-(pyrrolidin-1-yl)phenyl)piperazin-1-yl)-3-methyl-6-(4-pyrimidyl)-3H-pyrimidin-4-one;
2-(3-(2-methoxy-5-(pyrrolidin-1-yl)phenyl)piperazin-1-yl)-3-methyl-6-(4-pyrimidyl)-3H-pyrimidin-4-one;
2-(3-(4-(Phenyl)phenyl)piperazin-1-yl)-3-methyl-6-(4-pyrimidyl)-3H-pyrimidin-4-one;
2-(3-(4-(4-Fluorophenyl)phenyl)piperazin-1-yl)-3-methyl-6-(4-pyrimidyl)-3H-pyrimidin-4-one;
2-(3-(4-(4-Methoxyphenyl)phenyl)piperazin-1-yl)-3-methyl-6-(4-pyrimidyl)-3H-pyrimidin-4-one;
2-(3-(4-(2-Methoxyphenyl)phenyl)piperazin-1-yl)-3-methyl-6-(4-pyrimidyl)-3H-pyrimidin-4-one;
2-(3-(4-(Morpholin-4-yl)phenyl)piperazin-1-yl)-3-methyl-6-(4-pyrimidyl)-3H-pyrimidin-4-one;
2-(3-(4-(4-Methylpiperazin-1-yl)phenyl)piperazin-1-yl)-3-methyl-6-(4-pyrimidyl)-3H-pyrimidin-4-one;
2-(3-(4-Fluoro-2-methoxyphenyl)-4-methylpiperazin-1-yl)-3-methyl-6-(4-pyrimidyl)-3H-pyrimidin-4-one;
(S)-2-(3-(4-Fluoro-2-methoxyphenyl)-4-methylpiperazin-1-yl)-3-methyl-6-(4-pyrimidyl)-3H-pyrimidin-4-one;
(R)-2-(3-(4-Fluoro-2-methoxyphenyl)-4-methylpiperazin-1-yl)-3-methyl-6-(4-pyrimidyl)-3H-pyrimidin-4-one;
2-(4-Acetyl-3-(4-fluoro-2-methoxyphenyl)piperazin-1-yl)-3-methyl-6-(4-pyrimidyl)-3H-pyrimidin-4-one;
2-(4-Benzyl-3-(4-fluoro-2-methoxyphenyl)piperazin-1-yl)-3-methyl-6-(4-pyrimidyl)-3H-pyrimidin-4-one;
2-(4-(4-Fluorophenyl)piperidin-1-yl)-3-methyl-6-(4-pyrimidyl)-3H-pyrimidin-4-one;
2-(4-Cyano-4-phenylpiperidin-1-yl)-3-methyl-6-(4-pyrimidyl)-3H-pyrimidin-4-one;
2-(4-(6-Fluorobenofuran-3-yl)piperidin-1-yl)-3-methyl-6-(4-pyrimidyl)-3H-pyrimidin-4-one;
2-(3-(Benzoisoxazol-3-yl)piperidin-1-yl)-3-methyl-6-(4-pyrimidyl)-3H-pyrimidin-4-one;
(S)-2-(3-(Benzoisoazol-3-yl)piperidin-1-yl)-3-methyl-6-(4-pyrimidyl)-3H-pyrimidin-4-one;
(R)-2-(3-(Benzoisoxazol-3-yl)piperidin-1-yl)-3-methyl-6-(4-pyrimidyl)-3H-pyrimidin-4-one;
2-(3-(6-Fluorobenzoisoxazol-3-yl)piperidin-1-yl)-3-methyl-6-(4-pyrimidyl)-3H-pyrimidin-4-one;
2-(4-(6-Fluorobenzoisoxazol-3-yl)piperidin-1-yl)-3-methyl-6-(4-pyrimidyl)-3H-pyrimidin-4-one;
2-(4-(5-Methylbenzofuran-3-yl)piperidin-1-yl)-3-methyl-6-(4-pyrimidyl)-3H-pyrimidin-4-one; and
2-(4-(6-Fluorobenzothiophene-3-yl)piperidin-1-yl)-3-methyl-6-(4-pyrimidyl)-3H-pyrimidin-4-one.

Additional TBK1 inhibitors for use in the present invention include compounds according to the chemical structure:

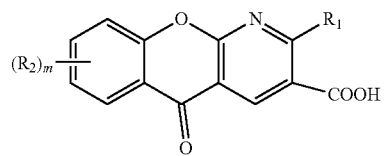

Where $R_1$ is hydrogen, $C_1$-$C_6$alkyl, phenyl, carboxyl, hydroxyl, O—$C_1$-$C_3$alkyl or amino which is optionally substituted with one $C_1$-$C_3$ alkyl group;

m is 0, 1 or 2; and $R_2$ is H, $C_1$-$C_6$ alkyl, halogen, nitro, hydroxyl, carboxyl, O—$C_1$-$C_3$alkyl, or a butadienylene (—C═C—C═C—) group which forms an unsaturated cyclic ring with any adjacent carbon atoms or nitrogen atom which may be unsubstituted or substituted with at least one $C_1$-$C_3$ alkyl group, or a pharmaceutically acceptable salt thereof.

In embodiments, the inhibitor of Syntaxin 17 phosphorylation is a small molecule compound or antibody which inhibits the phosphorylation of Syntaxin 17. In these embodiments, the preferred inhibitors of Syntaxin 17 phosphorylation include AG1478 (Tyrphostin AG1478) and AG1024 (Tyrphostin AG1024). In embodiments, the inhibitor of Syntaxin 17 is an anti-Syntaxin antibody, which is polyclonal or monoclonal, preferably a monoclonal antibody which is humanized. Examples of anti-Syntaxin antibodies which may be used in the present invention include humanized anti-Syntaxin-17 (Human) mAb which binds to STX-17 and prevents phosphorylation of Syntaxin 17. These antibodies may be delivered into the cell to effect therapy.

In embodiments, the TBK1 inhibitor, the inhibitor of Syntaxin 17 phosphorylation and/or the anti-Syntaxin 17 antibody may be combined with at least one additional autophagy modulator as describe herein, preferably an autophagy inhibitor, for example, tetrachlorisophthalonitrile, phenylmercuric acetate or a pharmaceutically acceptable salt thereof, among others as described herein and/or at least one additional anticancer agent as described herein.

In an additional embodiment, the present invention is directed to pharmaceutical compositions which comprise an effective amount of a compound which is a TBK-1 inhibitor, a Syntaxin 17 phosphorylation inhibitor such as AG1478 (Tyrphostin AG1478) AG1024 (Tyrphostin AG1024) or an anti-Syntaxin 17 antibody, as described above, in combination with at least one autophagy modulator, preferably an autophagy inhibitor for example, tetrachlorisophthalonitrile, phenylmercuric acetate or a pharmaceutically acceptable salt thereof, among others and/or at least one additional anticancer agent as described herein in combination with a pharmaceutically acceptable carrier additive and/or excipient.

In an another embodiment, the present invention is directed to treating a disease state or condition which favorably responds to autophagy inhibition, in this case a TBK1 inhibitor as described herein, an inhibitor of Syntaxin 17 phosphorylation such as AG1478 and/or AG102 and/or an anti-Syntaxin 17 antibody, preferably humanized. Disease states and/or conditions which favorably respond to therapeutic treatment with at least one TBK1 inhibitor and/or an inhibitor of Syntaxin 17 phosphorylation (e.g., anti-Syntaxin 17 antibody) and additional optional bioactive agents (including additional autophagy modulators) include cancer, rheumatoid arthritis, malaria, antiphospholipid antibody syndrome, lupus, chronic urticarial, Sjogren's disease, autoimmune-related Type I diabetes, rheumatoid arthritis (RA), psoriasis/psoriatic arthritis, multiple sclerosis, inflammatory bowel disease (IBD) including Crohn's disease and ulcerative colitis, Addison's disease, Grave's disease, Hashimoto's thyroiditis, Myasthenia gravis, autoimmune vasculitis, pernicious anemia and celiac disease.

In an embodiment, a therapeutic method for treating a patient in need comprises administering to said patient an effective amount of at least one TBK1 antagonist and/or at least one inhibitor of Syntaxin 17 phosphorylation (e.g., anti-Syntaxin 17 antibody), optionally in combination with at least one additional bioactive agent, such as an additional anti-cancer agent or autophagy modulator. The therapeutic method according to the present invention may be used to treat the patient for cancer, rheumatoid arthritis, malaria, antiphospholipid antibody syndrome, lupus, chronic urticarial, Sjogren's disease, autoimmune-related Type 1 diabetes, rheumatoid arthritis (RA), psoriasis/psoriatic arthritis, multiple sclerosis, inflammatory bowel disease (IBD) including Crohn's disease and ulcerative colitis, Addison's disease, Grave's disease, Hashimoto's thyroiditis, Myasthenia gravis, autoimmune vasculitis, pernicious anemia and celiac disease.

In another embodiment, the present invention is directed to an assay and method for identifying a compound with unknown activity (test compound) as an inhibitor of Syntaxin 17 phosphorylation. In this method, a cell or cell lysate which comprises and/or expresses TBK1 and Syntaxin 17 in the absence of test compound results in the phosphorylation of Syntaxin 17 at Serine residue 202 ($Stx17^{pS202}$). The extent of $Stx17^{pS202}$ is identified by exposure of $Stx17^{pS202}$ to a monoclonal or polyclonal antibody (capture antibody) which specifically binds to $Stx17^{pS202}$ (anti-$Stx17^{pS202}$ antibody) and a second antibody (detection antibody) as a monoclonal or polyclonal antibody which comprises a reporter and which binds to the anti-$Stx17^{pS202}$ antibody. The binding of the second (detection) antibody to the anti-$Stx17^{pS202}$ antibody identifies Stx17 phosphorylation ($Stx17^{pS202}$) by emitting a signal from the conjugated reporter of the detection antibody and measuring the signal emitted from the reporter. The assay may be conducted in vitro (e.g. in cell lysate) or partially in whole cells. In this assay, the cells or preferably, the cell lysates (which includes lysates from the whole cells) are exposed to a test compound and the absence or substantial reduction of anti-$Stx17^{pS202}$-antibody (capture antibody) in the sample evidences (by virtue of a low signal or an absence of signaling from the detection antibody) that the compound is an inhibitor of Stx 17 phosphorylation (because little, if any, phosphorylation occurred) and a potential agent for use as an autophagy modulator for the treatment of cancer or autoimmune disease as described herein, and the presence of a signal from the reporter evidences that phosphorylation of Stx17 occurred and the test compound is not an inhibitor of Stx17 phosphorylation and therefore not a potential therapeutic agent for the treatment of cancer or autoimmune disease. The intensity of the signal from the reporter (by comparison to one or more standards) may evidence that the test compound is a partial inhibitor or a full inhibitor. The reporter of the detection antibody may be a fluorescent moiety or other moiety (e.g. quantum dots, gold nanoparticles, etc. as generally described herein) which elicits a measurable signal which can identify the concentration of $Stx17^{pS202}$ in a sample. These reporters which may be used in assays according to the present invention are described in detail herein.

As indicated above, the assays may be conducted in a cell lysate (ie. in an in vitro setting, which is preferred) or at least partially in cells wherein TBK-1 and Syntaxin 17 are expressed and Syntaxin 17 is phosphorylated prior to the cells being lysed (test compound can be added to whole cells or cell lysate) and exposed to capture antibody and detection antibody. The use of cells or cell lysates (cell-free) to express proteins is well known in the art and commercial systems are available. In one embodiment, TBK-1 and Syntaxin 17 are expressed in HEK293 (human embryonic kidney 293 cells) or other eukaryotic cells. In embodiments, prokaryotic cells are used to express proteins. In embodiments, the protein expression is performed cell-free (in vitro, e.g. in cell lysate). When cell-based expression is used to phosphorylate Syntaxin, test compound is preferably added to the cells prior to lysing the cells for exposure to antibody. Alternatively, test compound can be added to a lysate of the cells. Of course, the entire assay may be performed in vitro (e.g. in cell lysate).

In an embodiment, the present invention is thus directed to a method for identifying a test compound with unknown activity as a Syntaxin 17 phosphorylation inhibitor as having inhibitory activity of Syntaxin 17 phosphorylation, comprising exposing a cell or cell lysate which comprises and/or expresses TBK-1 and Syntaxin 17 to produce phosphorylated Syntaxin 17 at serine residue 202 ($Stx^{pS202}$) to said test compound, exposing said lysate or a lysate of said cell to an anti-$Stx^{pS202}$ capture antibody and a detection antibody which binds to said capture antibody comprising a reporter and measuring a signal emitted from the detection antibody reporter wherein a low or insubstantial signal from said detection antibody is evidence that the test compound is an inhibitor of Syntaxin 17 phosphorylation and a substantial signal emitted from said detection antibody evidences that the test compound has little to no activity as an inhibitor of Syntaxin 17 phosphorylation.

Assays according to the present invention comprise a cell or cell lysate which expresses both TBK1 and Syntaxin 17 and has the ability to phosphorylate Syntaxin 17 to $Stx17^{pS202}$. The assay also comprises an anti-$Stx17^{pS202}$ antibody (monoclonal or polyclonal capture antibody) capable of binding to $Stx17^{pS202}$ and a second antibody (monoclonal or polyclonal detection antibody) which binds to the anti-$Stx17^{pS202}$ capture antibody and comprises a reporter which can elicit a signal in order to measure the amount of anti-$Stx17^{pS202}$ capture antibody which is bound to the phosphorylated Syntaxin. The signal elicited from the reporter may be compared with a standard which represents full inhibition of Stx17 phosphorylation (full or heightened signal) or an absence of inhibition of Stx17 phosphorylation (no or low signal).

In additional embodiments, the present invention is directed to a kit comprising cells or components to be added to media to provide a cell lysate which are engineered to express TBK1 and Syntaxin 17, an anti-$Stx17^{pS202}$ antibody (as a monoclonal or polyclonal capture antibody) and a second antibody (detection antibody) comprising a reporter which is capable of binding to the anti-$Stx17^{pS202}$ antibody and instructions for use of the components of the kit in identifying compounds which inhibit phosphorylation of Syntaxin17. Compounds that are determined to be inhibitors of Syntaxin phosphorylation may be potential therapeutic agents in the treatment of cancer or one or more autoimmune diseases as otherwise described herein.

Addition embodiments of the present invention may be readily gleaned from the detailed description of the invention which follows.

BRIEF DESCRIPTION OF THE FIGURES

FIG. 4 shows that Phosphorylation of Stx17 by TBK1 is required for formation of ATG13 and FIP200 puncta. (AB) HC analysis of effect of complementation of Stx17KO cells with FLAG-Stx17WT, FLAG-Stx17S202A and FLAG-Stx17S202D on formation of ATG13 dots in response to autophagy induction by incubation with EBSS for 1h. White masks, computer-identified FLAG positive cells (primary objects); red masks, computer identified ATG13 dots in FLAG transfected cells. HeLa WT (left) were left untransfected for control. (Scale bar 10 μm). , $p<0.01$, (n=3) ANOVA. (C,D) HC analysis to analyze the effect of complementation of Stx17KO with FLAG-Stx17 WT, FLAG-Stx17S202A and FLAG-Stx17S202D on formation of FIP200 dots in response to autophagy induction by incubation with EBSS for 1h. White masks, computer-identified FLAG positive cells (primary objects); red masks, computer-identified FIP200 dots in FLAG transfected cells. Scale bar 10 μm. , $p<0.01$, (n=3) ANOVA. (E,F). HC analysis of effect of cross complementation of TBK1KO cells with FLAG-Stx17WT, FLAG-Stx17S202A and FLAGStx17S202D on formation of FIP200 dots in response to autophagy induction by incubation with EBSS for 1h. White masks, computer-identified FLAG positive cells (primary objects); red masks, computer-identified ATG13 dots in FLAG transfected cells. White masks, computer-identified FLAG positive cells (primary objects); red masks, computer-identified ATG13 dots in FLAG transfected cells. Scale bar 10 μm. , $p<0.01$, (n=3) ANOVA. (G,H) HC analysis of effect of cross-complementation of TBK1KO cells with FLAG-Stx17WT, FLAG-Stx17S202A and FLAG-Stx17S202D on formation of FIP200 dots in response to autophagy induction by incubation with EBSS for 1h. White masks, computer-identified FLAG positive cells (primary objects); red masks, computer-identified ATG13 dots in FLAG transfected cells. Scale bar 10 μm. , $p<0.01$, (n=3) ANOVA. (I) A model depicting the effect of Stx17 on formation of mammalian pre-autophagosomal structures and omegasomes. In HC experiments (AH), Images are details from a large database of machine-collected and computer processed images; data are from 3-5 independent experiments (>500 primary object examined per well; minimum number of wells, 12).

S202D with endogenous FIP200 in 293T cells. (F) Graph showing quantifications between FIP200 and FLAG-Stx17 variants. , p<0.01, (n=3) ANOVA. (G) Confocal microscopy analysis of colocalization between endogenous ATG13 and Stx17pS202 in BMMs incubated with EBSS for 1 h. Scale bar 5 μm. (H,I) HC microscopy analysis and quantifications of colocalization between ATG13 and Stx17pS202 in BMMs incubated in full media or induced for autophagy by incubation with EBSS for 1h. Blue masks, algorithm-defined cell boundaries (primary objects); yellow masks, computer-identified overlap between Stx17pS202 and ATG13 dots. , p<0.01, (n=3) t-test. (J) Confocal microscopy analysis of colocalization between GFP-FIP200 and Stx17pS202 in HeLa cells incubated with EBSS for 1h. (K, L) HC microscopy analysis and quantifications showing colocalization between GFP-FIP200 and Stx17pS202 in HeLa cells transfected with GFP-FIP200 and incubated in full media or induced for autophagy by incubation with EBSS for 1h. Blue masks, computer-identified GFP-FIP200 positive cells (primary objects), yellow masks, computer-identified overlap between Stx17pS202 and GFP-FIP200 dots in GFP positive cells. , p<0.01, (n=3) t-test. (M) Confocal microscopy analysis of colocalization between GFP-ULK1 and Stx17pS202 in HeLa cells incubated with EBSS for 1h. (N, O) High content microscopy and quantifications showing colocalization between GFPULK1 and Stx17pS202 in HeLa cells transfected with GFP-ULKL1 and incubated in full media or induced for autophagy by incubation with EBSS for 1 h. White masks, computer-identified GFP-ULK1 positive cells (primary objects); yellow masks, computer identified overlap between Stx17pS202 and GFP-ULK1 dots in GFP positive cells. , p<0.01, (n=3) t-test. Masks; white: GFP-ULK1 positive objects cells; yellow: number of Stx17pS202 dots also positive for GFP-ULK1 dots. (P) A model showing Stx17pS202 as an interacting partner of mPAS complex. In HC experiments (H,I,K,L,M,O), images are details from a large database of machine-collected and computer-processed images; data are from 3 independent experiments (>500 primary object examined per well; minimum number of wells, 20).

Figure 6:
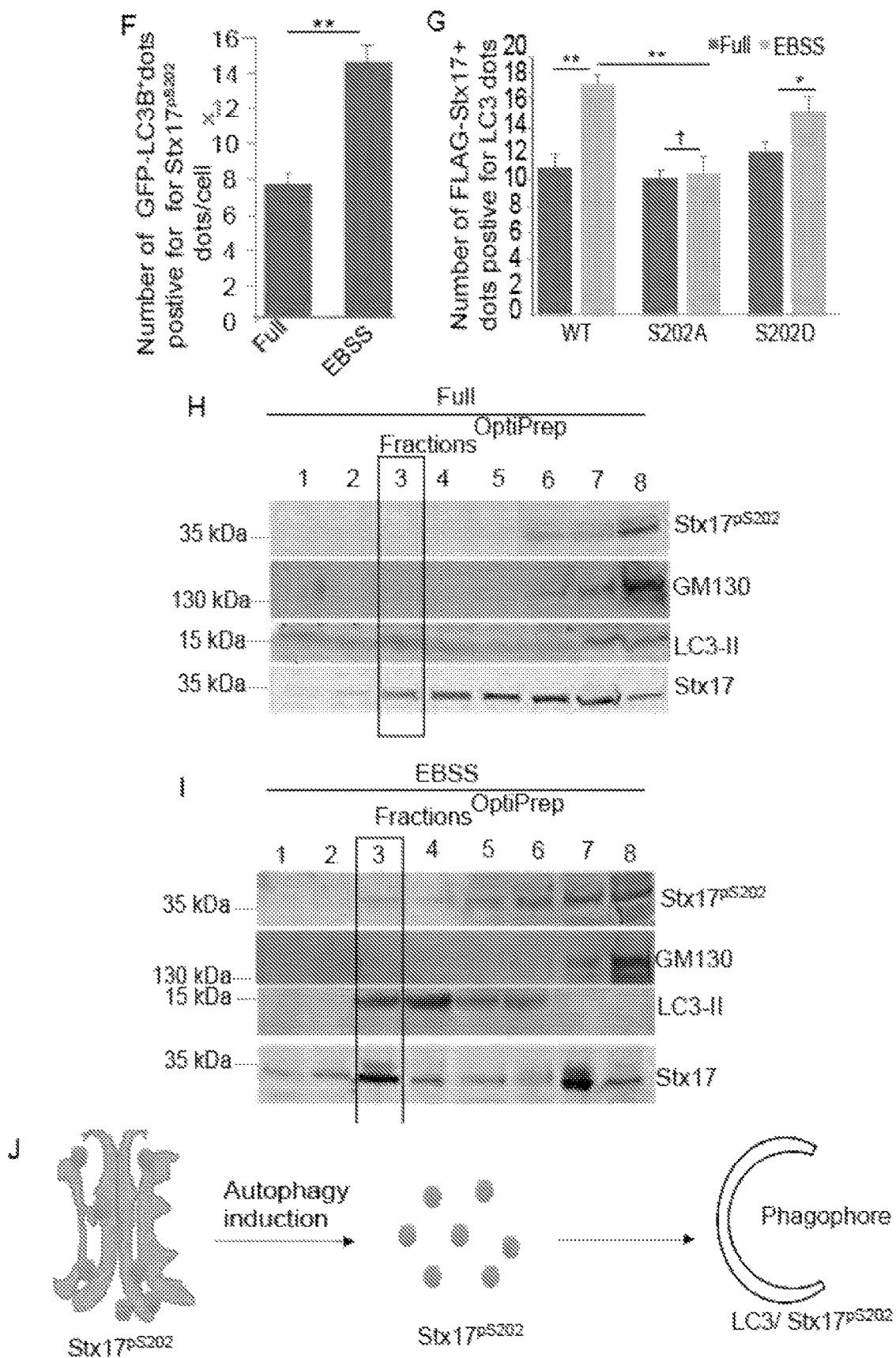

FIG. 6 shows that Stx17pS202 is on LC3-positive autophagosome upon induction of autophagy. (A) Confocal microscopy showing colocalization between GFP-LC3B and Stx17pS202 in HeLa cells incubated with EBSS for 2h. Scale bar 5 μm. (B) Pearson's correlation coefficient (>20 cells) of colocalization between GFP-LC3B and Stx17pS202. (C, D) Super-resolution microscopy to analyze colocalization between GFP-LC3B and Stx17pS202 in HeLa cells incubated with EBSS for 2h. Scale bar S00 nm. (E,F) HC microscopy and quantifications showing colocalization between GFP-LC3B and Stx17pS202 in HeLa cells incubated in full media or in EBSS for 2h. Scale bar 10 μm. . p<0.01, (n=3) t-test. Blue masks, algorithm-defined GFP-LC3B positive cells (primary objects); yellow masks, computer-identified overlap between Stx17pS202 and GFP-LC3B dots. Images are details form a large database of machine-collected and computer processed images, (G) HC quantifications showing colocalization between FLAG-Stx17 WT, FLAG-Stx17 S202A and FLAG-Stx17 S202D with LC3 in HeLa cells incubated in full media or in EBSS for 2h. , p<0.01, (n=3) ANOVA; data are from 3 independent experiments (>500 primary object examined per well; minimum number of wells, 12). (H, I) Membrane fractions using OptiPrep gradients to test redistribution of Stx17pS202 from Golgi (H) in full media to LC3-II fraction in EBSS (I). (J) A model depicting translocation of Stx17pS202 to LC3+ phagophore upon induction of autophagy.

Figure 7:
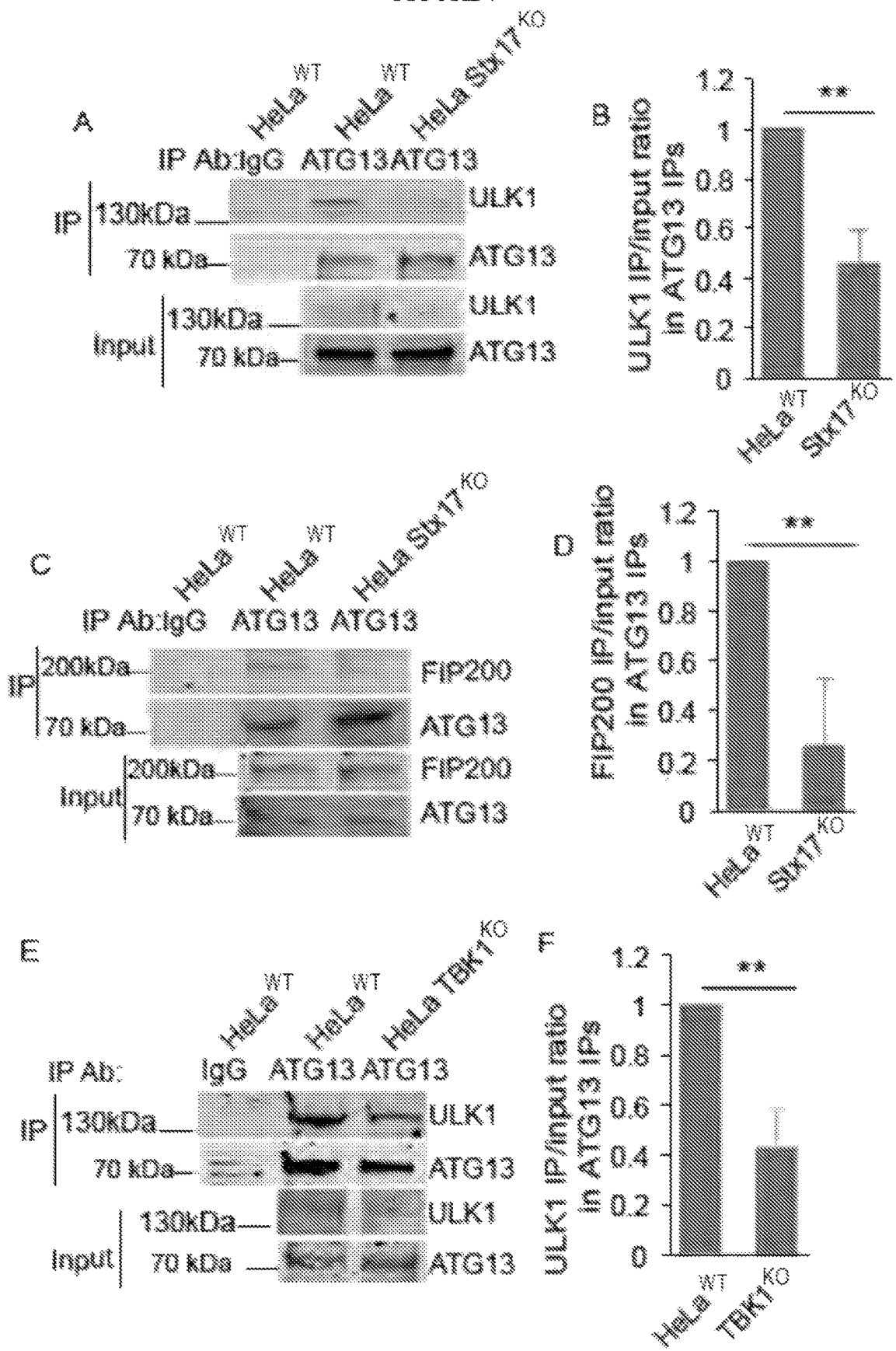
Figure 7:
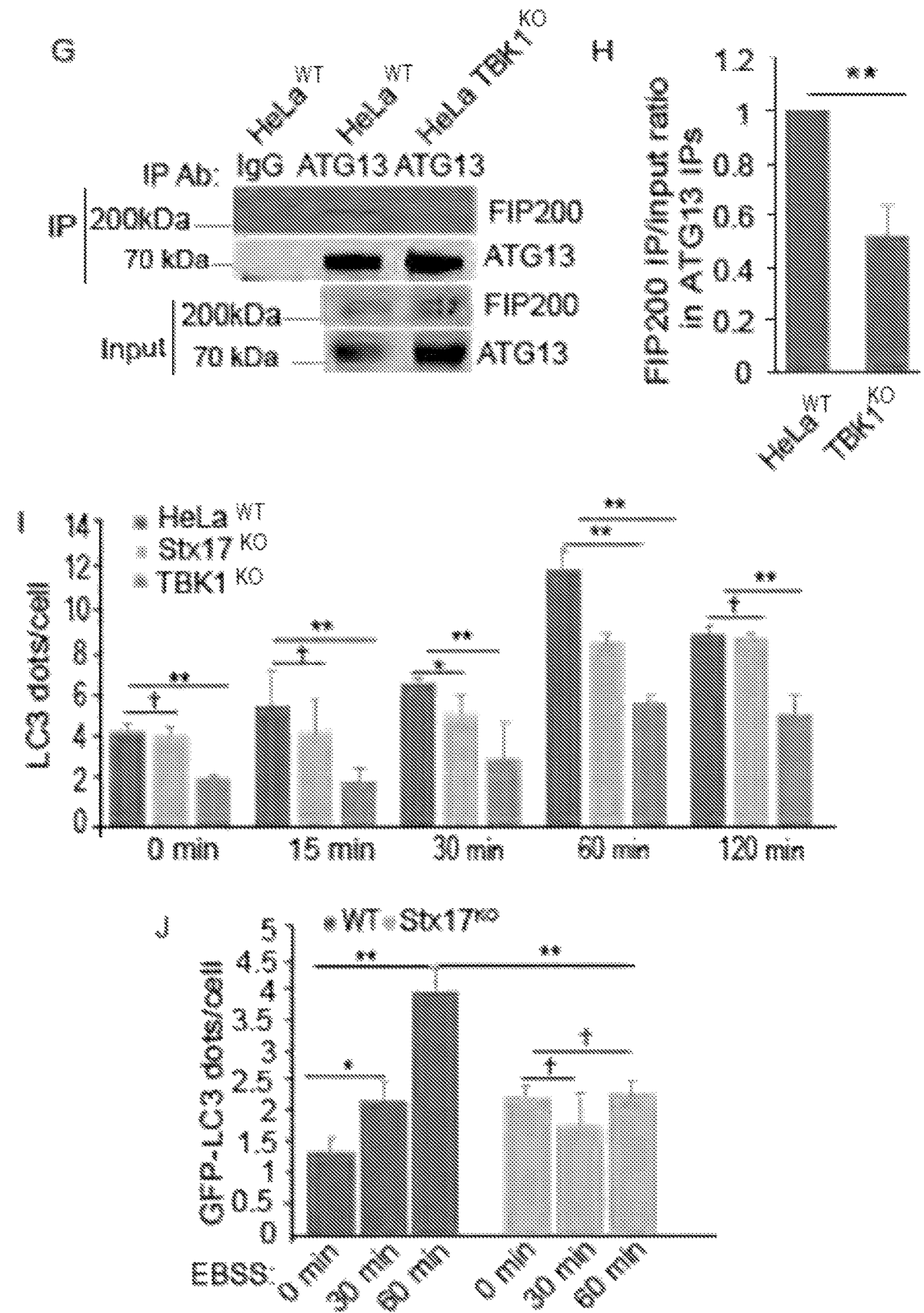

FIG. 7: Stx17 is required for autophagy initiation. (A) Co-IP analysis of interactions between ATG13 and ULK1 in HeLaWT or Stx17KO cells. (B) Graph showing quantification of IP/input ratio of ULK1 in Co-IP with ATG13 in HeLa wild type vs Stx17 knockouts. p<0.01, (n=3) t-test. (C) Co-IP analysis of interactions between ATG13 and FIP200 in HeLaWT or Stx17KO cells. (D) Graph showing quantification of IP/input ratio of ATG13 in Co-IP with FIP200 in HeLa wild type vs Stx17 knockouts. p<0.01, (n=3) test. (E,F) Co-IP analysis of interactions between ATG13 and ULK1 in HeLaWT or TBK1KO cells. (F) Quantifications from three independent experiments showing ULK1 IP/input ratio. p<0.01, (n=3) t-test. (G,H) Co-IP analysis of interactions between FIP200 and ATG13 in HeLaWT or TBK1KO cells. (H) Quantifications from three independent experiments showing ULK1 IP/input ratio. p<0.01, (n=3) t-test. (I) HC quantification showing the effect of Stx17 and TBK1 knockouts on formation of LC3 dots in time dependent starvation response. *, p<0.05; **, p<0.01, (n=3) ANOVA. data are from 4 independent experiments (>500 primary object examined per well; minimum number of wells, 12). (J) HC analysis to test the effect of Stx17KO on GFP-LC3 puncta formation after 30 min or 1h of starvation. *, p<0.05; **, p<0.01, (n=3) ANOVA, data are from 3 independent experiments (>500 primary object examined per well; minimum number of wells per plate per time point, 16). (K) Screen shot of HC-scanned 96 well plate of HeLa cells transfected with mCherry-GFP-LC3B and incubated with EBSS for 0 min, 30 min or 60 min; HeLaWT (left half of the plate) or in Stx17KO (right half of the plate). For each experimental well, a minimum of 500 valid object/cells per well were counted for GFP-LC3 puncta. (L, M) HC microscopy analysis and quantification of Keima-LC3 fluorescence at 440 nm in HeLaWT or Stx17KO cells incubated in full media or in EBSS for 6h. White masks, algorithm-defined Keima-LC3 positive cells (primary objects); purple masks, computer-identified Keima-LC3 dots. *, p<0.05; **, p<0.01, (n=3) ANOVA. (N) Schematics showing different steps in LDH sequestration assay. (O) LDH sequestration assay showing the effect of Stx17 and ATG13 knockouts on LDH sequestration in cell induced for autophagy by incubation with EBSS for 2h in presence of bafilomycin A1.3 methyladenine (10 mM) was used as a positive control. (P) LDH sequestration assay showing the effect of mATG8s knockouts on LDH sequestration in cells induced for autophagy by incubation with EBSS for 2h in presence of bafilomycin A1. (Q, R) HC analysis and quantification of LDH-keima fluorescence at 440 nm in HeLa wt or Stx17KO cells incubated in full media or with EBSS for 2h.*, p<0.05; **, p<0.01, (n=3) ANOVA. White masks, algorithm-defined LDH-Keima positive cells (primary objects); purple masks, computer-identified LDH-Keima dots. (S) Model showing Stx17 in ER membranes and moves to Golgi after its phosphorylation by TBK1. After induction of autophagy Stx17pS202 translocates from Golgi to peripheral puncta and is associated with the FIP200/ATG13/ULK1 complex, which with additional components form mPAS. In HC experiments (L,M,Q,R), images are details form a large database of machine collected and computer-processed images, and data are from 3 independent experiments (>500 primary object examined per well: minimum number of wells, 30).

Figure 1:
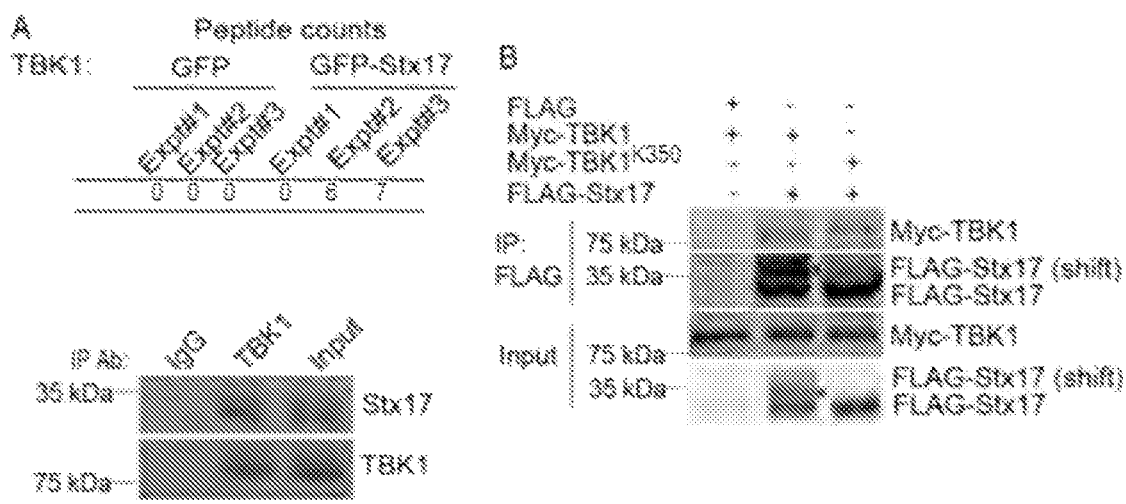
FIG. 1 shows that TBK1 interacts with and phosphorylates Stx17 at Ser-202 (A) MS analysis showing comparison of GFP or GFP-Stx17 peptides in co-IPs with TBK1, extracted from Table S1 (upper panel). Co-IP between endogenous Stx17 and TBK1 in 293T cells (lower panel). (B) Co-IP of FLAG-Stx17 with Myc-TBK1WT or Myc-TBK1K38D in 293 Tcells. * indicates the phospho-shift in FLAG-Stx17 induced by Myc-TBK1WT (lane 2) and not by Myc-TBK1K38D (lane 3). (C) Mass-spec analysis showing phosphorylation of FLAG-Stx17 at Ser-202 residue induced by Myc-TBK1 (right panel) and not by Myc alone (left panel). (D) Western blot analysis of Stx17pS202 levels in WT, Stx17KO and TBK1 KO HeLa cells treated with 500 ng/ml of LPS for 4h. White asterisk, Stx17pS202 (note minor levels in TBK1 knockout cells). (E) A schematic showing phosphorylation of Stx17 at Ser-202 residue by TBK1.
Figure 1:
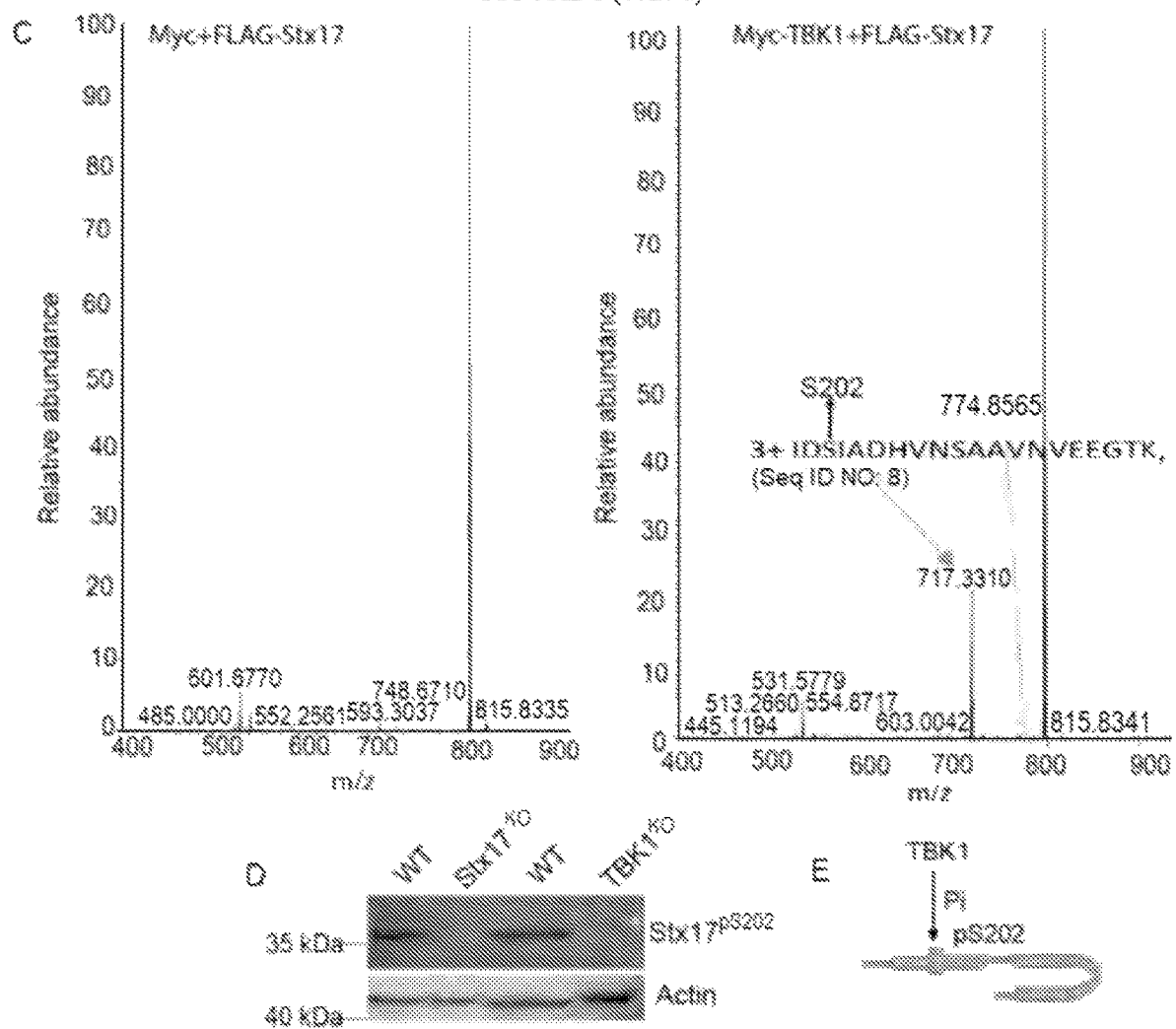
Figure 8:
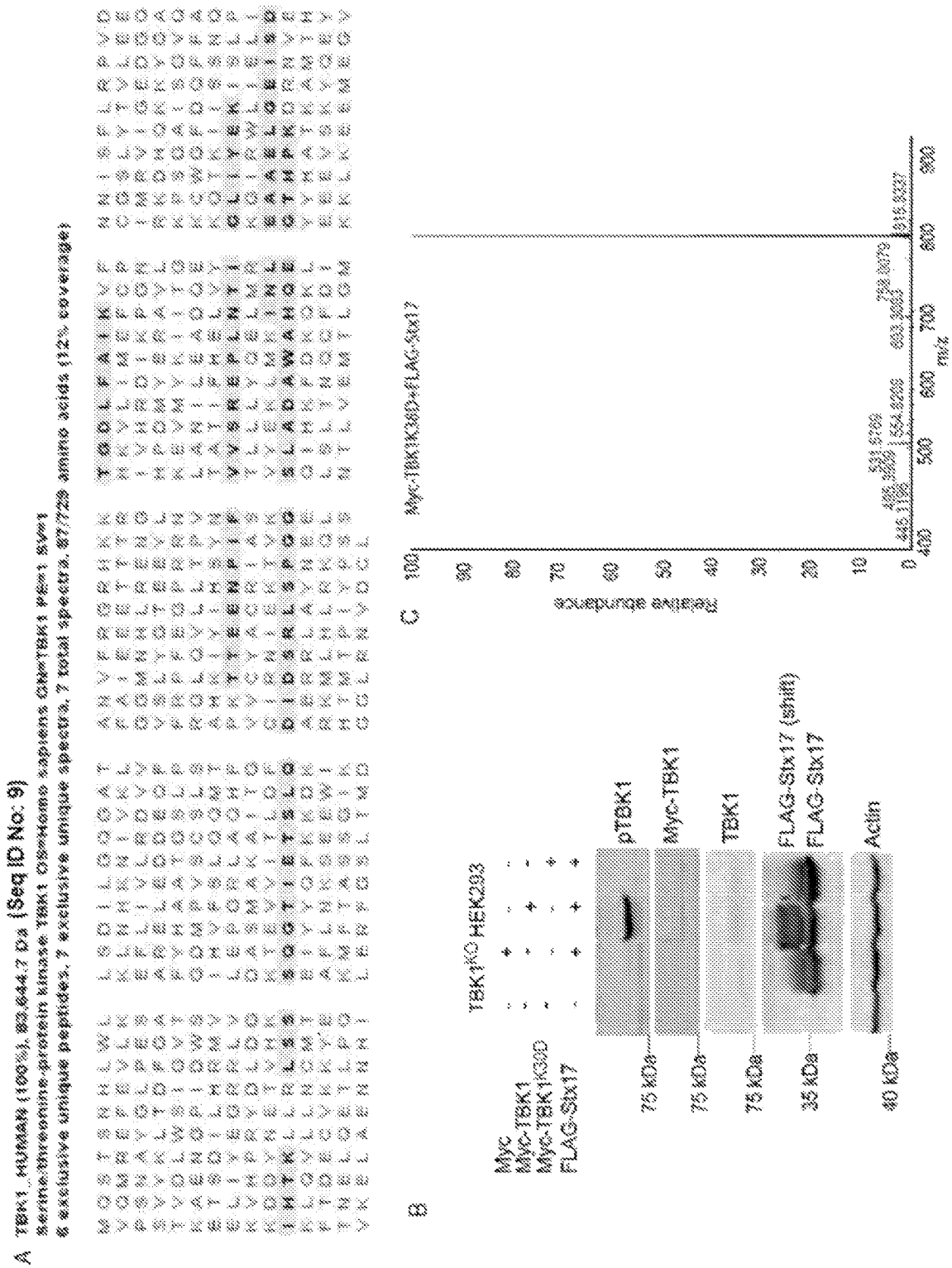

FIG. 8 (related to FIG. 1) shows that TBK1 phosphorylates Stx7. (A) A screenshot captured from the scaffold software indicating number of TBK1 peptides interacting with GFP-Stx17 in proteomics study (related to FIG. 1A). (B) Western blot from TBK1KO 293T cells expressing Myc, Myc-TBK1WT or Myc-TBK1K38D with FLAG-Stx17. "*" represents phosphorylation-induced shift. (C) MS analysis from TBK1KO 293T cells to analyze the effect of Myc-TBK1K38D on FLAG-Stx17 phosphorylation (related to FIG. 1C). (D) Sequence alignment showing conserved S202 residue in Stx17 from human to fish. (E) Crystal structure from database showing location of S202 in Stx17. (F) Western blot confirming Stx17 knock out in Stx17KO HeLa cells. (G) Western blot showing TBK1 knock out in TBK1KO HeLa cells. (H) Western blot to analyze the effect of MDP or LPS on expression of Stx17pS202 in HeLa cells. (I) Western blot to analyze the effect of TBK1 agonist LPS and inhibitor BX795 on expression of Stx17pS202 in HeLaWT or TBK1KO cells.

Figure 2:
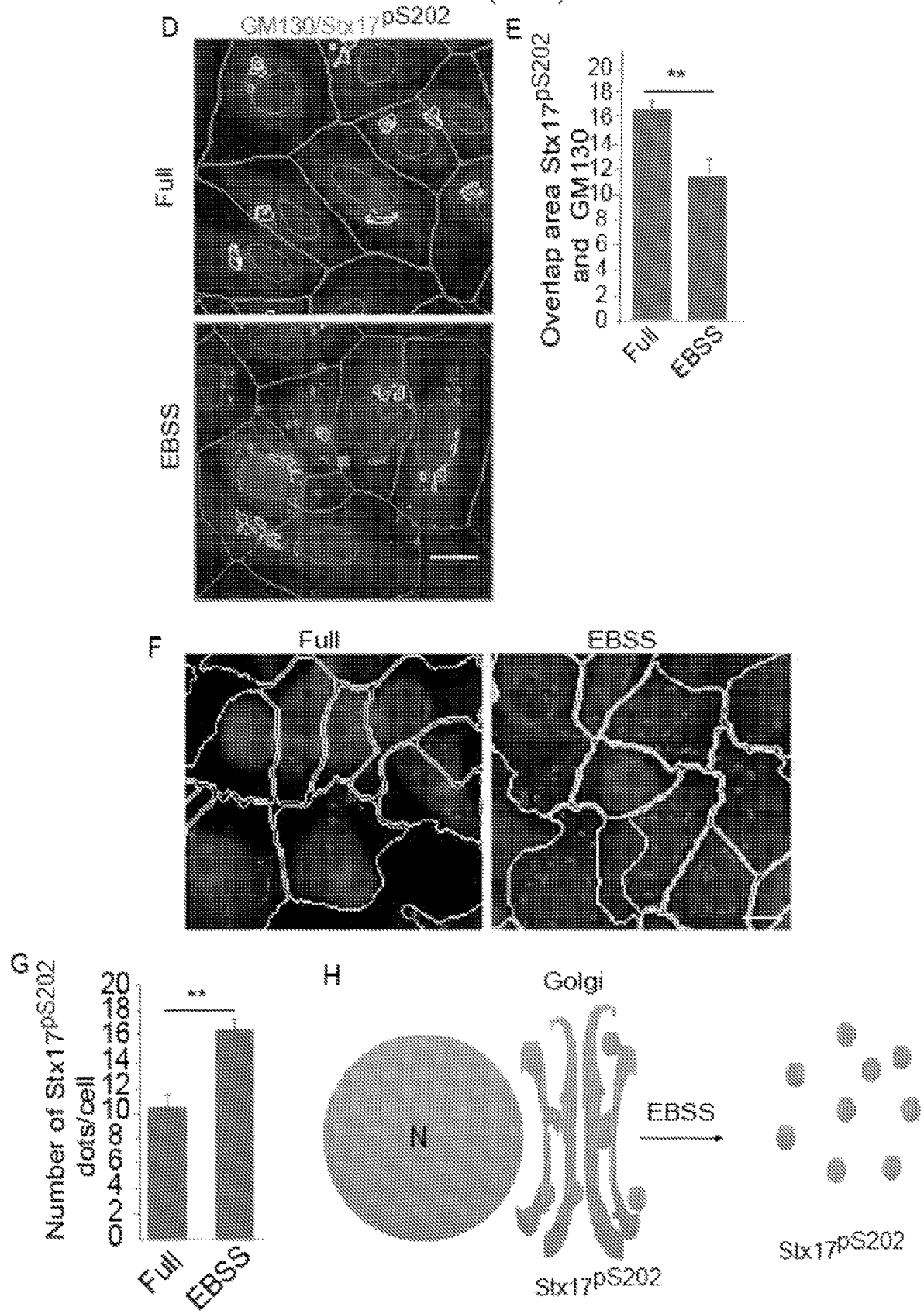
FIG. 2 shows that Stx17pS202 is localized in the Golgi. (A) Confocal microscopy analysis of colocalization between Stx17pS202 and GM130 in WT (upper panel) or Stx17KO HeLa cells (lower panel). (B) Membrane fractionation using OptiPrep gradients to analyze subcellular fractionation of Stx17pS202. (C) Confocal microscopy analysis of Stx17pS202 redistribution to peripheral puncta in response to autophagy induction by incubation with EBSS for 1h (Lower panel). (D, E) High content microscopy (HC) of HeLa cells showing colocalization between Stx17pS202 and GM130 in full and starved (1 h EBSS) conditions. *, $p<0.01$, (n=3) t-test, from 3 independent experiments (>500 primary object examined per well; minimum number of wells, 30). Green masks, algorithm-defined cell boundaries (primary objects); yellow masks, computer-identified overlap between Stx17pS202 and GM130 (target objects); green masks, computer-identified Stx17pS202 dots. Images, a detail form a large database of machine-collected and computer processed images. (F, G) High content microscopy and quantification to analyze the redistribution of Stx17pS202 to peripheral puncta in response to autophagy induction by starvation. **, $p<0.01$, (n=3) t-test. from 3 independent experiments (>500 primary object examined per well; minimum number of wells, 30). White masks, algorithm defined cell boundaries (primary objects); yellow masks, computer-identified Stx17pS202 dots. Images, a detail form a large database of machine-collected and computer processed images. (H) A model depicting translocation of Stx17pS202 from Golgi to peripheral puncta upon induction of autophagy with starvation. Scale bars: confocal images 5 μm; HC images, 10 μm.
Figure 9:
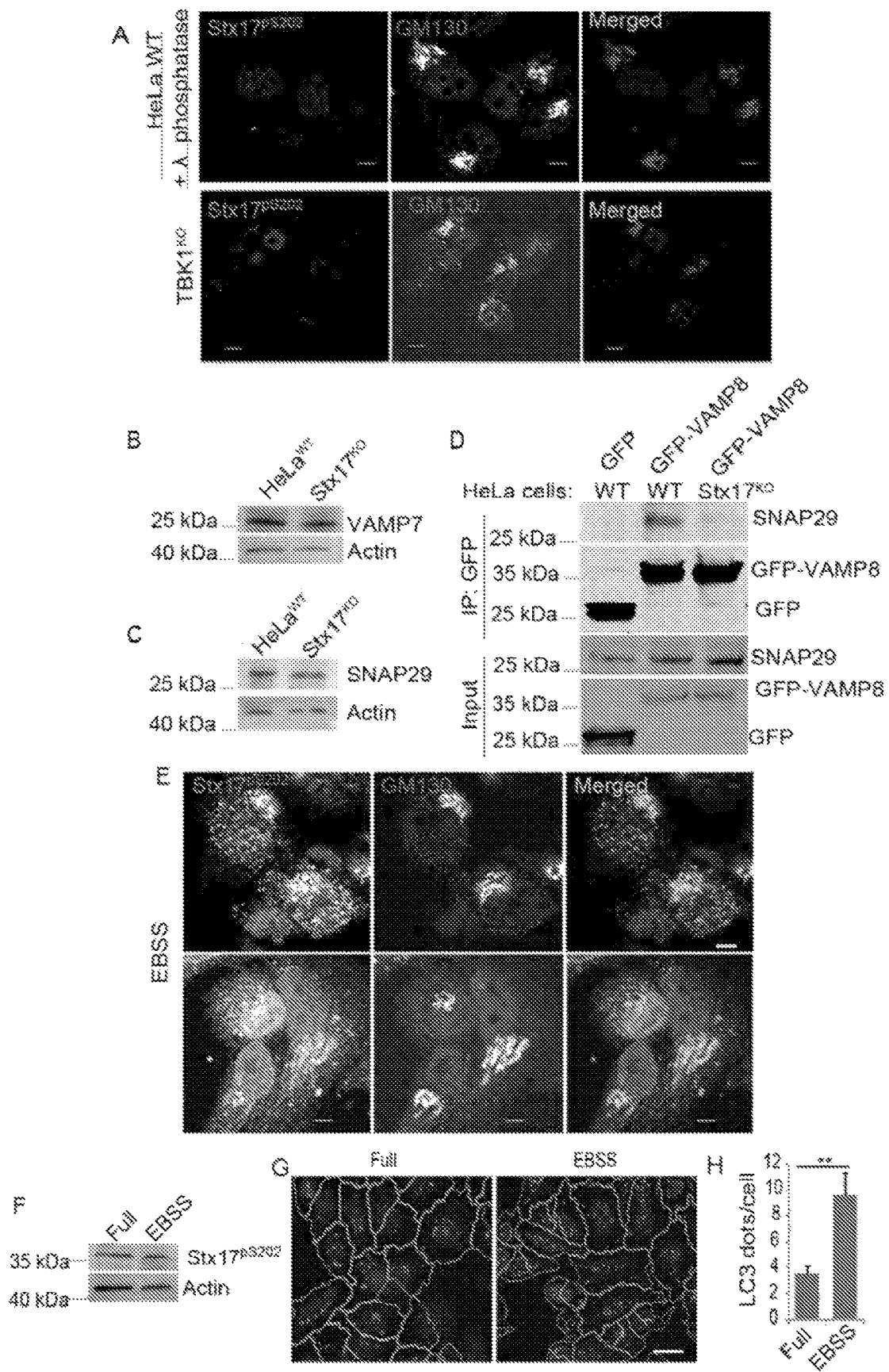

FIG. 9 (related to FIG. 2) shows that Stx7pS202 is localized In Golgi. (A) Wild type HeLa cells were treated with A phosphatase (upper row), while TBK1KO HeLa cells (lower row) were left untreated and stained with Stx17pS202 and GM130. Colocalization between Stx17pS202 and GM130 was analyzed by confocal microscopy. Scale bar 5 μm. (B, C) Western blot to analyze the effect of Stx17KO on stability of VAMP7 or SNAP29. (D) Co-IP analysis of interaction between GFP-VAMP8 and SNAP29 in HeLa WT or Stx17 KO cells. (E) Confocal microscopy to analyze the distribution of Stx17pS202 from Golgi to peripheral dots in response to autophagy induction by EBSS. GM130 is used to stain Golgi. Scale bar 5 μm. (F-H) Western blot showing effect of starvation (2h EBSS) induced autophagy (as shown by induction of LC3 dots in C,D) on levels of Stx17pS202. White masks, algorithm-defined cell boundaries (primary objects); green masks, computer-identified LC3 dots. **, $p<0.01$, (n=3) t-test.

Figure 3:
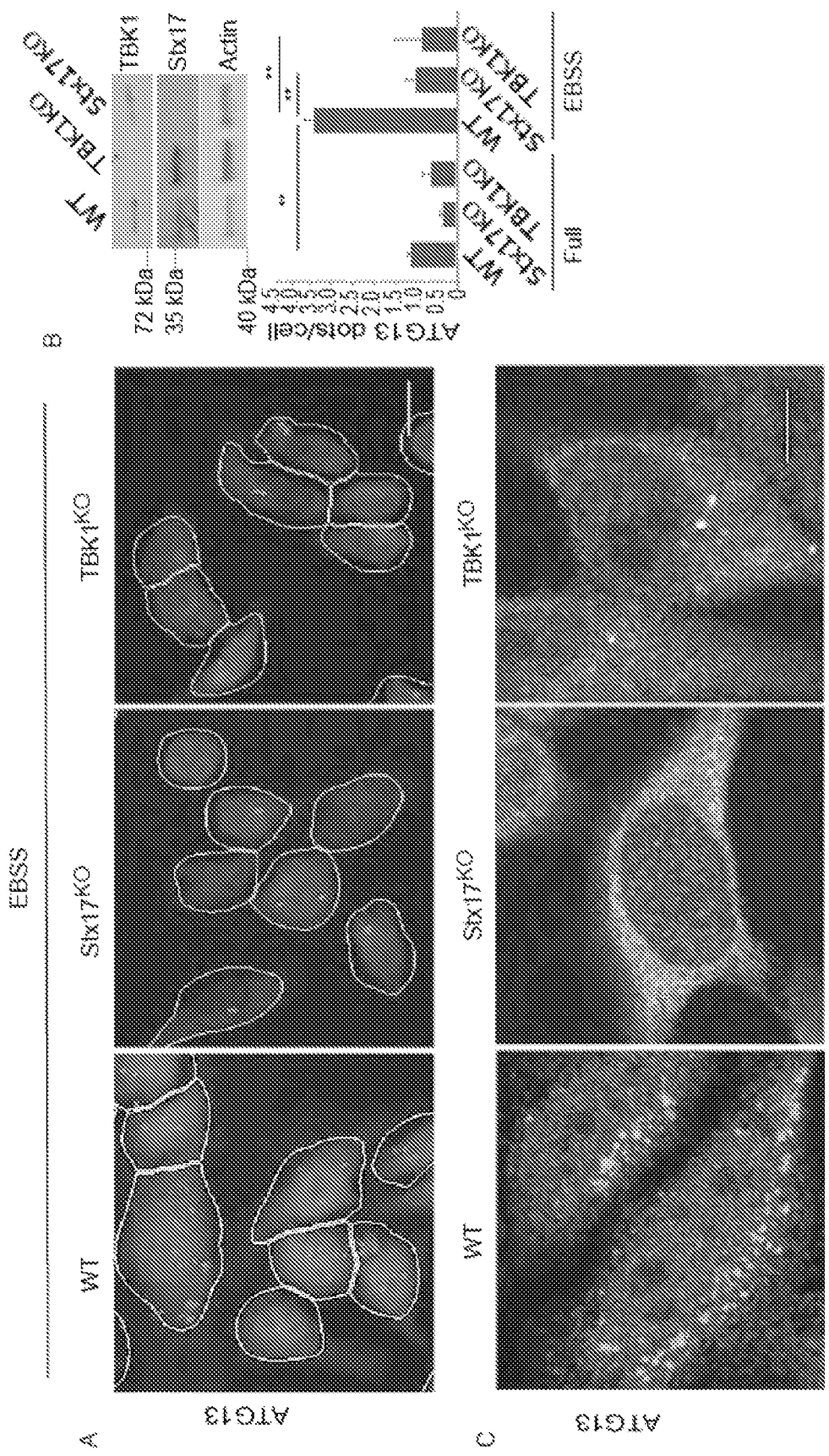
FIG. 3 shows that Stx17 and TBK1 are required for formation of mPAS. (A,B) HC analysis of effect of Stx17 and TBK1 knockouts on formation of ATG13 puncta in HeLa cells induced for autophagy by incubating in EBSS for 1h. White masks, algorithm-defined cell boundaries (primary objects); green masks, computer-identified ATG13 dots. Images, a detail from a large database of machine-collected and computer-processed images (see B). Western blot panel shows Stx17 and TBK1 knockouts in HeLa cells. Panel to the right, Western blot showing TBK1 and Stx17 knockouts in HeLa cells. (B) High content quantifications showing the effect of Stx17 and TBK1 knockouts on formation of ATG13 puncta in HeLa cells induced for autophagy by incubating in EBSS for 1h. Scale bar 10 μm. , $p<0.01$, (n=3) ANOVA; from 4 independent experiments (>500 primary object examined per well; minimum number of wells, 60). (C) Confocal microscopy showing the effect of Stx17 and TBK1 knockouts on formation of ATG13 puncta in HeLa cells incubated in full media or induced for autophagy by incubation with EBSS for 1h. Scale bar 5 μm. (D, E) High content microscopy and quantifications showing the effect of Stx17 and TBK1 knockouts on formation of FIP200 puncta in HeLa cells incubated in full media or EBSS for 1h. Scale bar 10 μm. , $p<0.01$, (n=3) ANOVA; from 4 independent experiments (>500 primary object examined per well; minimum number of wells, 60). Blue masks, algorithm-defined cell boundaries (primary objects); green masks, computer-identified FIP200 dots. Images, a detail form a large database of machine-collected and computer-processed images. (F) Confocal microscopy analysis of the effect of Stx17 and TBK1 knockouts on formation of FIP200 puncta in HeLa cells induced for autophagy by incubating in EBSS for 1h. Scale bar 5 μm.
Figure 3:
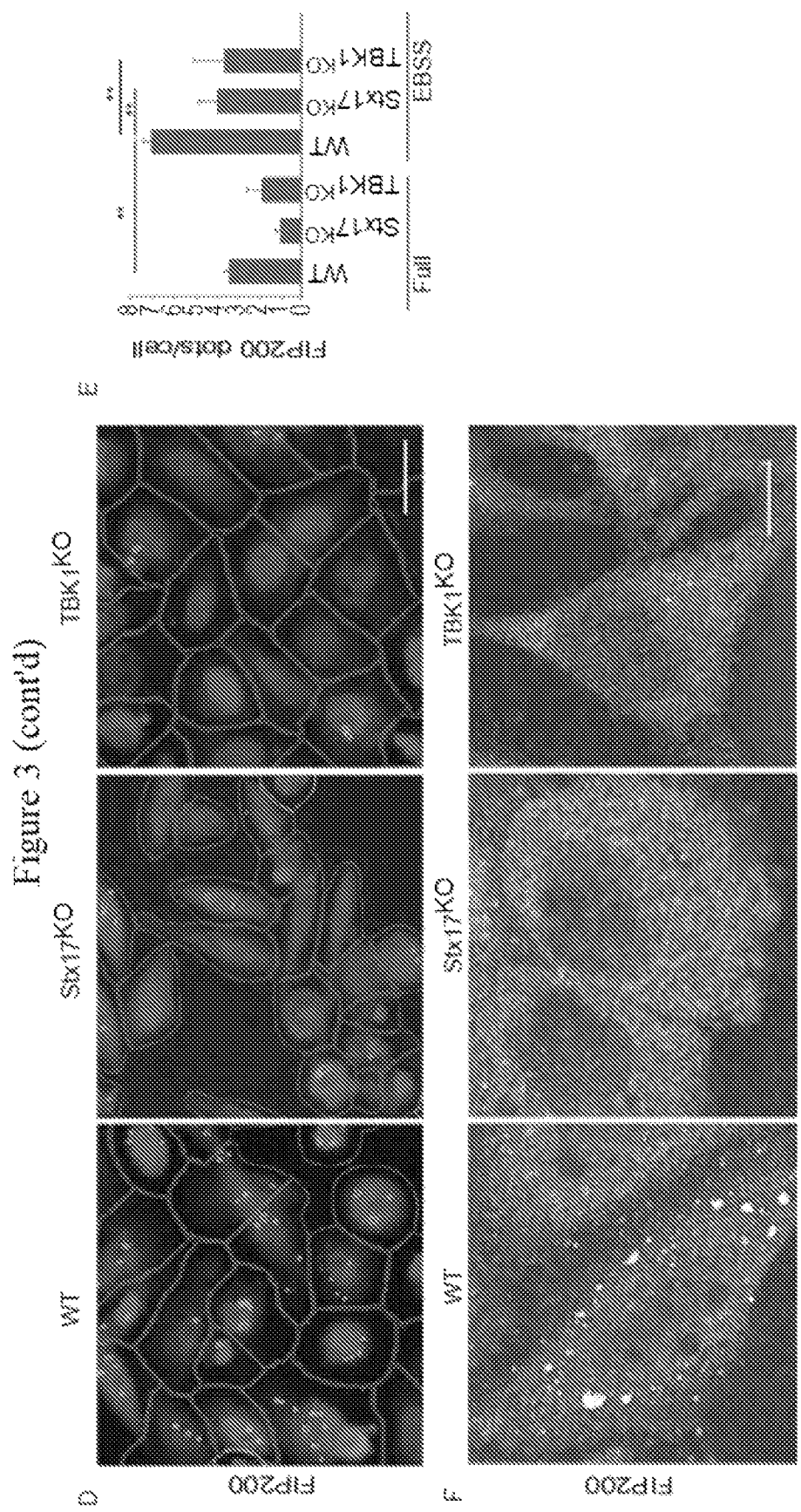
Figure 10:
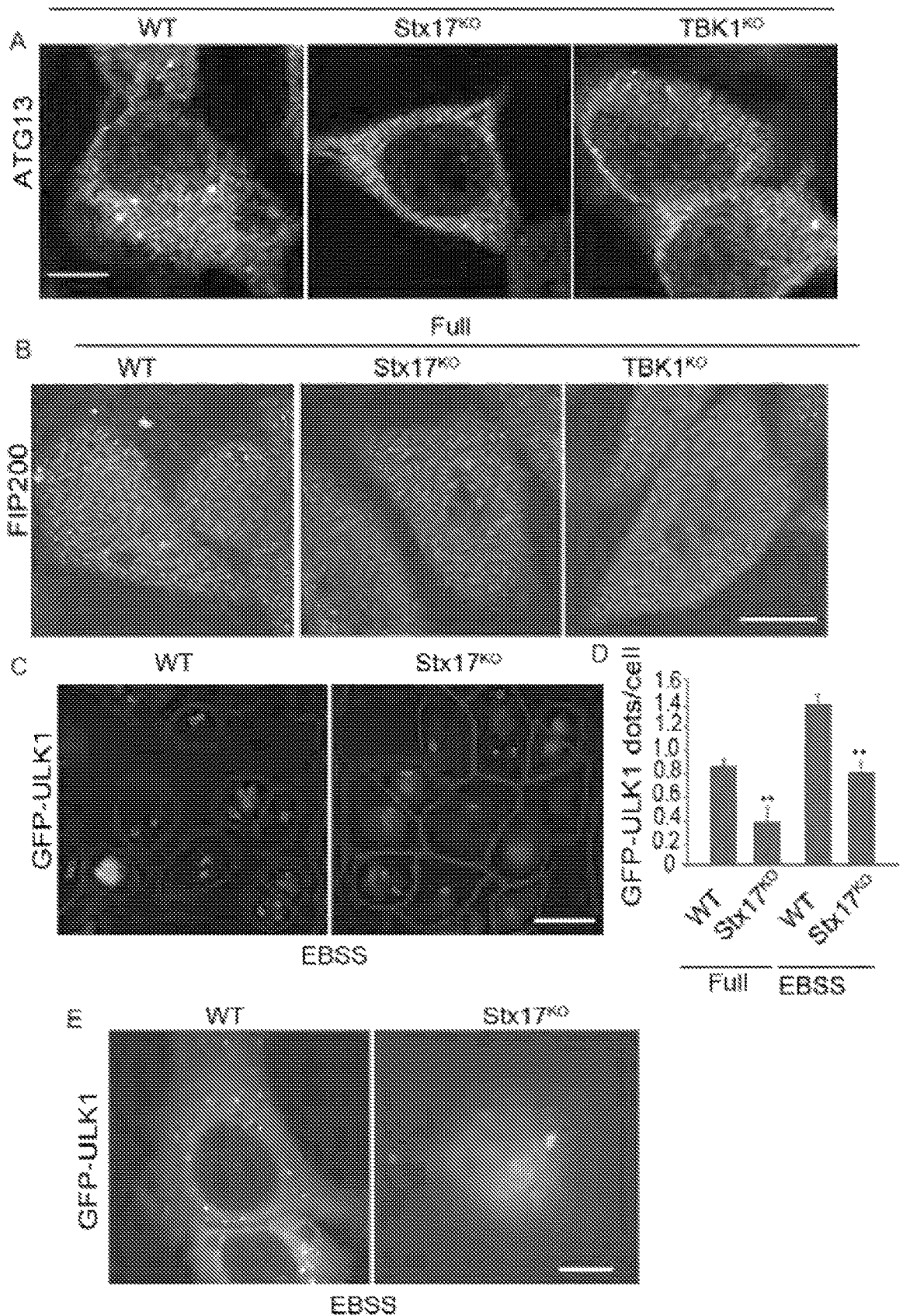
Figure 10:
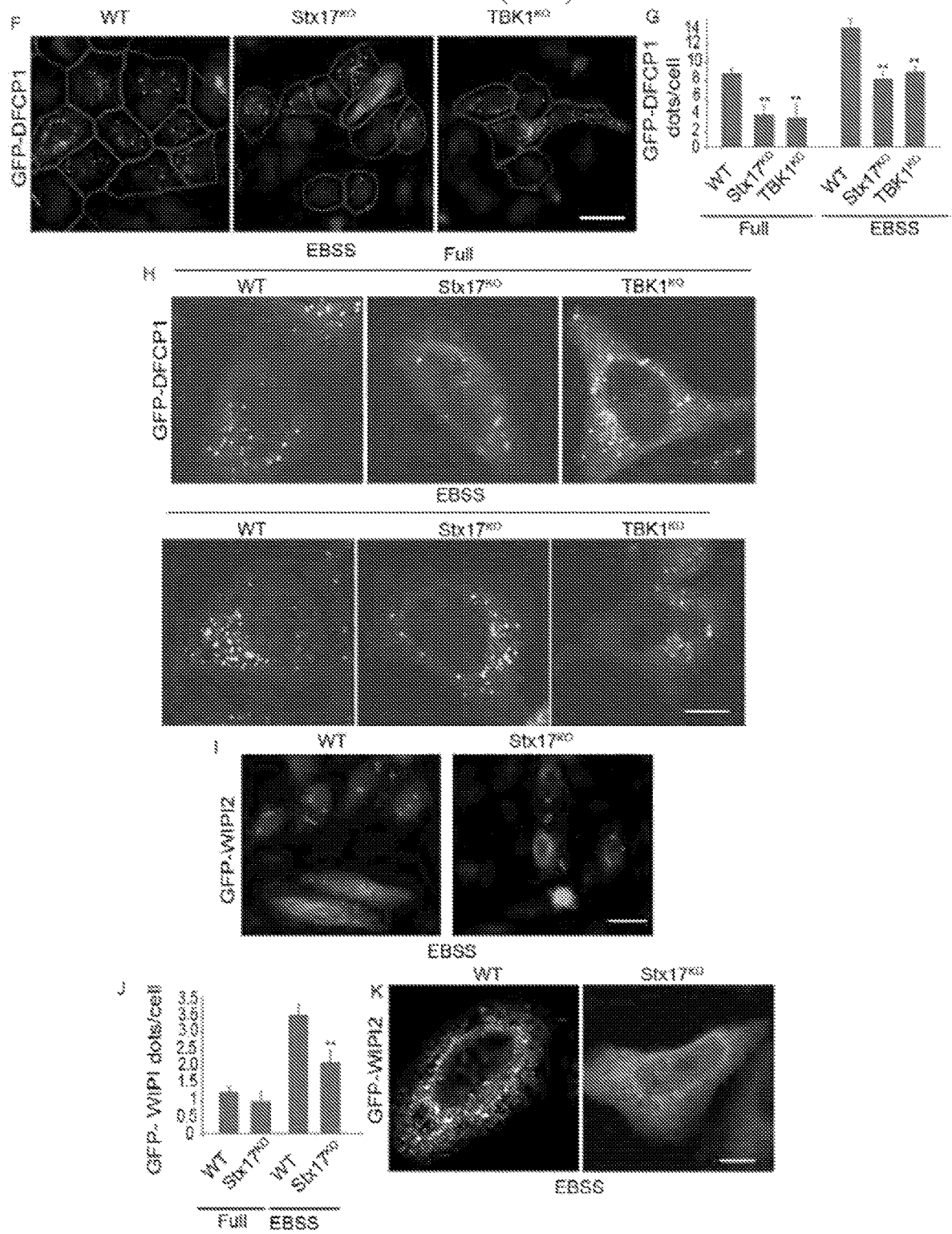

FIG. 10 (related to FIG. 3) shows that Stx17 and TBK1 are required for formation of preautophagosomal structures. (A, B) Confocal microscopy analysis of effects of Stx17KO and TBK1KO on formation of ATG13 and FIP200 dots. Scale bar 5 μm. (C, D) HC analysis of effect of Stx17KO on formation of ULK1-GFP dots in full media or cells induced for autophagy by incubating in EBSS for 1h. , $p<0.01$, (n=3) ANOVA. Blue masks, algorithm-defined ULK-GFP positive cells (primary objects); green masks, computer-identified ULK1-GFP dots. (E) Confocal microscopy to analyze the effect of Stx17KO on formation of ULK1-GFP dots. Scale bar 5 μm. (F,G) High content microscopy and quantifications showing effect of Stx17 and TBK1 knock outs on formation of GFP-DFCP1 dots in cells incubated in full media or induced for autophagy by incubating in EBSS for 1h. , $p<0.01$, (n=3) ANOVA. Blue masks, algorithm-defined GFP-DFCP1 positive cells (primary objects); green masks, computer-identified GFPDFCP1 dots. (H) Confocal microscopy to analyze the effect of Stx17 and TBK1 knock outs on formation of GFP-DFCP1 dots in cells incubated with full media or induced for autophagy by incubating with EBSS for 1h. (I, J) High content analysis showing effect of Stx17KO on formation of GFP-WIPI2 dots in full media or cells induced for autophagy by incubating in EBSS for 1h. Blue masks, algorithm-defined GFP-WIPI2 positive cells (primary objects); green masks, computer-identified GFP-WIPI2 dots. **, $p<0.01$, (n=3) ANOVA. (K) Confocal microscopy to analyze the effect of Stx17 and TBK1 knock outs on formation of GFP-WIPI2 dots.

Figure 5:
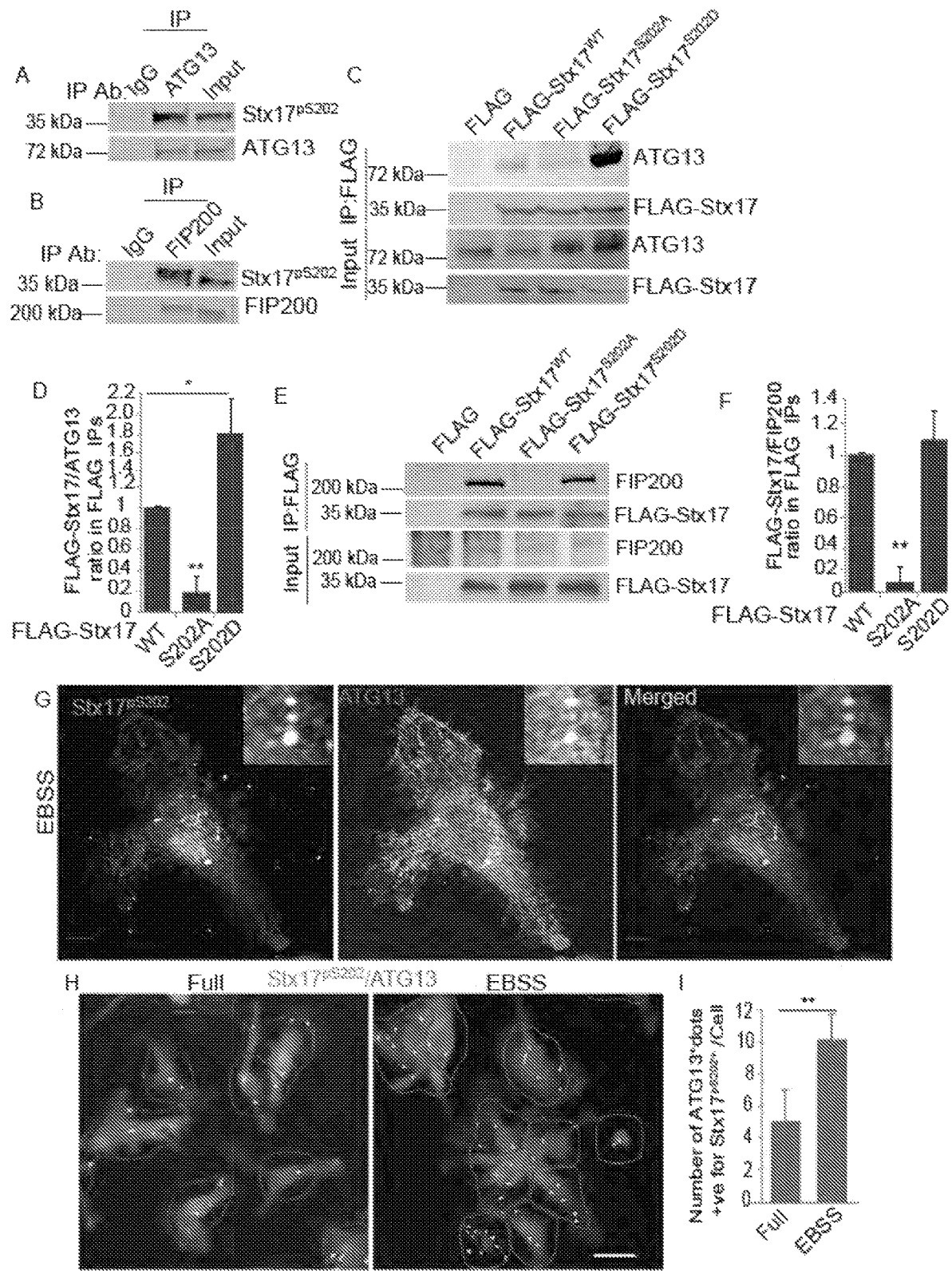
FIG. 5 shows that Stx17pS202 Interacts with ATG13 and FIP200. (A, B) Co-IP showing interactions of endogenous ATG13 (A) or FIP200 (B) with Stx17pS202 in 293 T cells. (C) Co-IP analysis of interactions between FLAG tagged Stx17 WT, Stx17 S202A or Stx17 S202D and ATG13 in 293T cells. (D) Graph showing quantifications of interactions between ATG13 and FLAG-Stx17 variants. **, $p<0.01$, (n=3) ANOVA. (E) Co-IP analysis of interactions between FLAG tagged Stx17 WT, Stx17 S202A or Stx17
Figure 5:
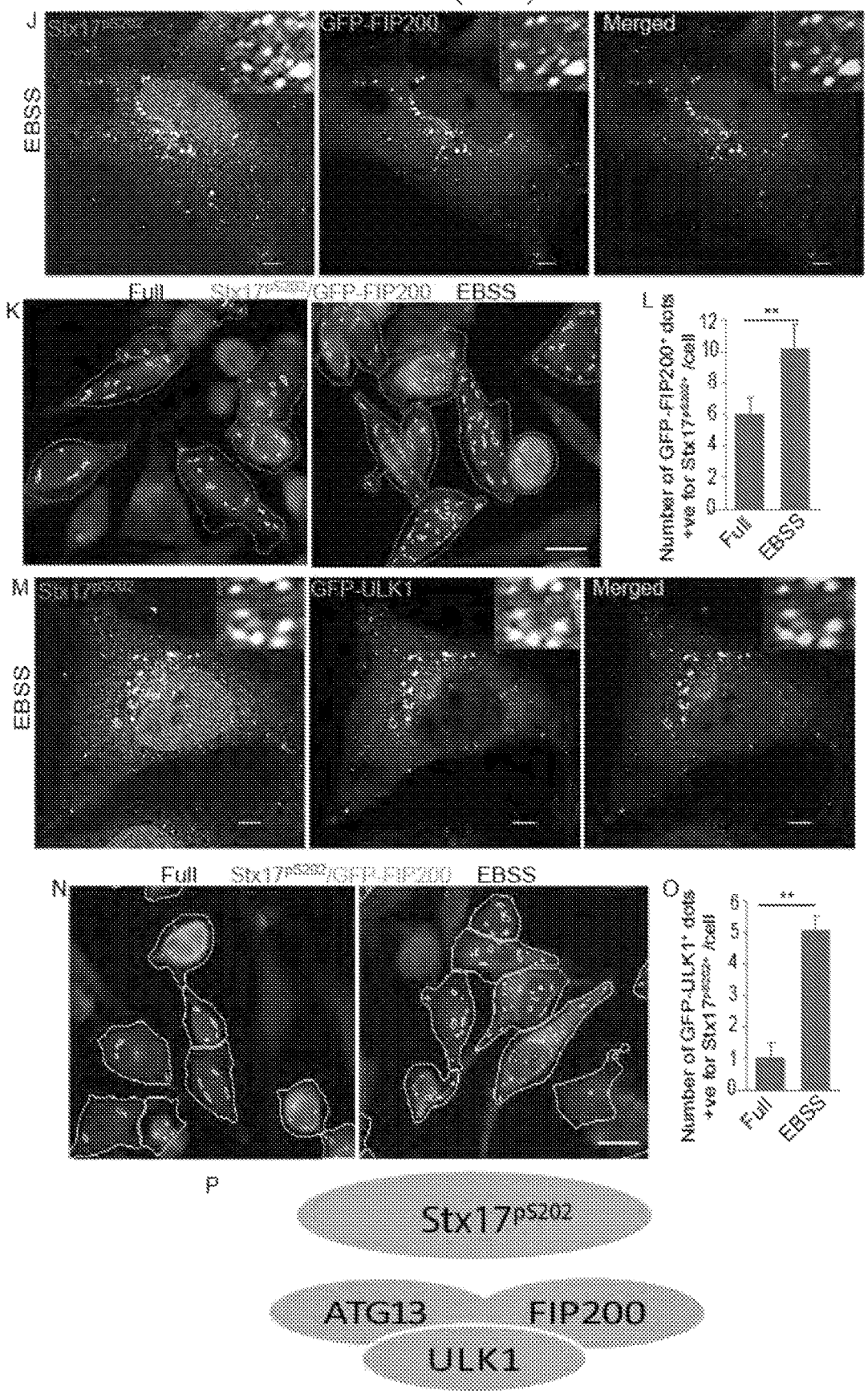
Figure 11:
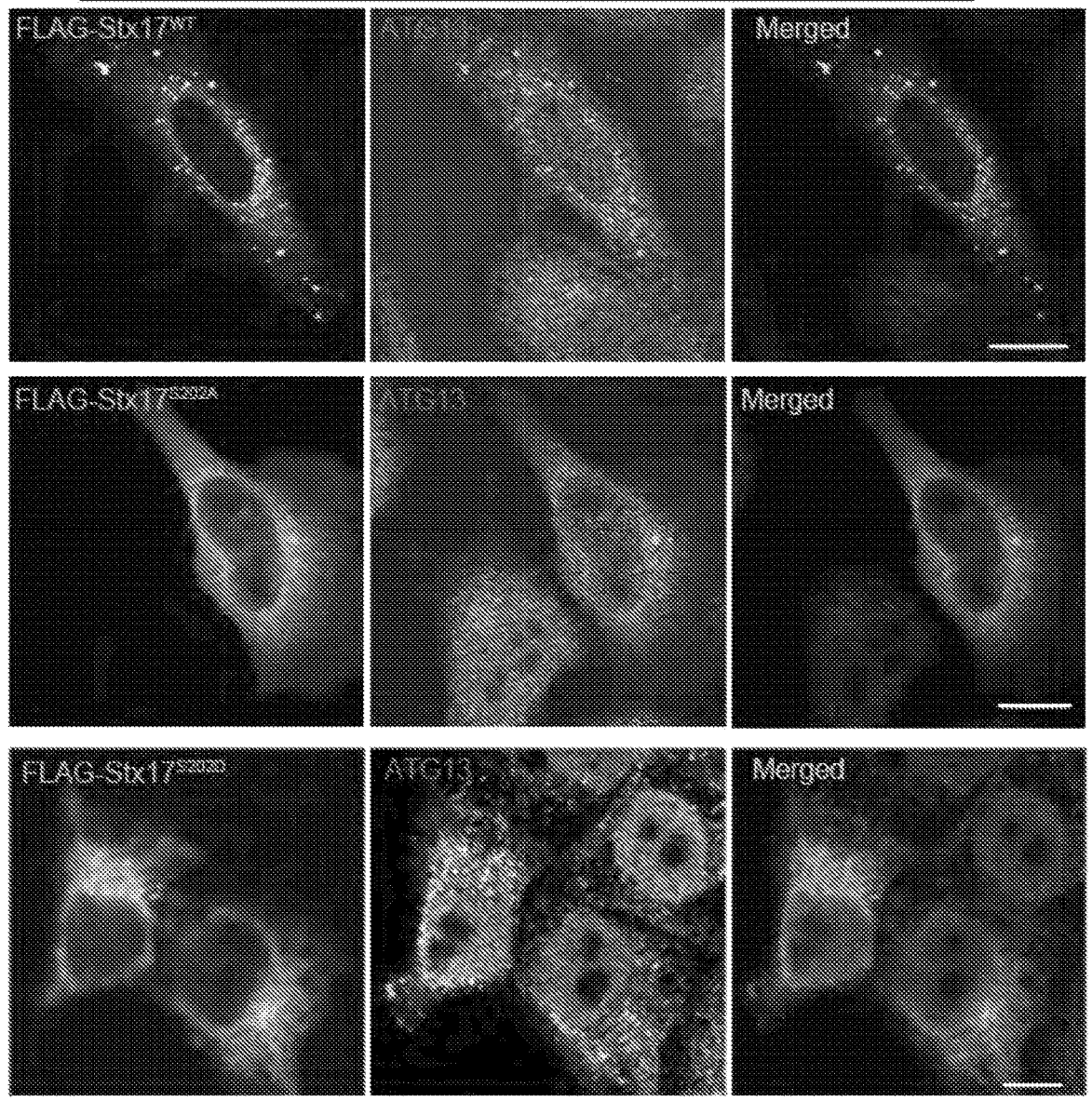
Figure 11:
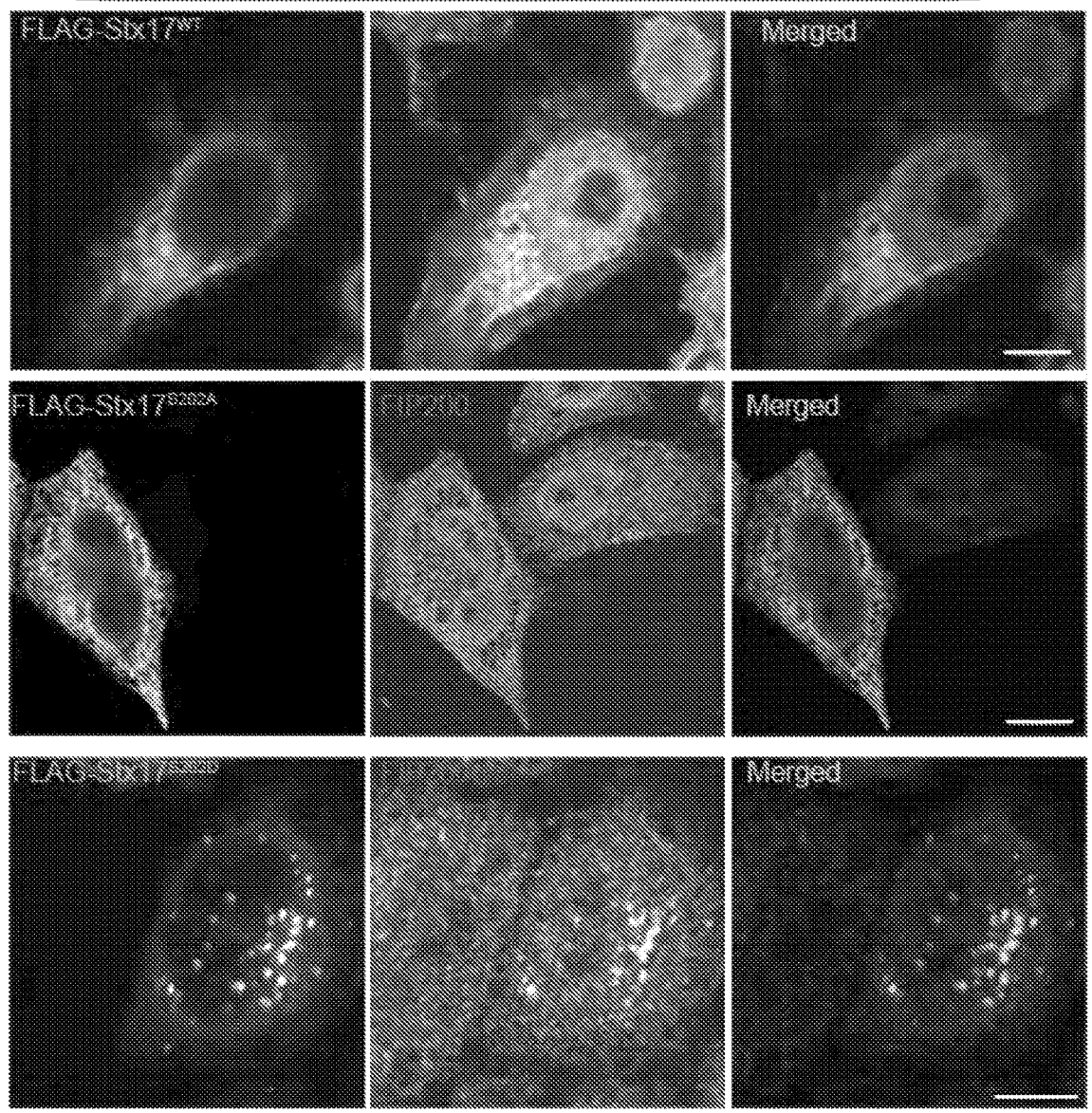
Figure 11:
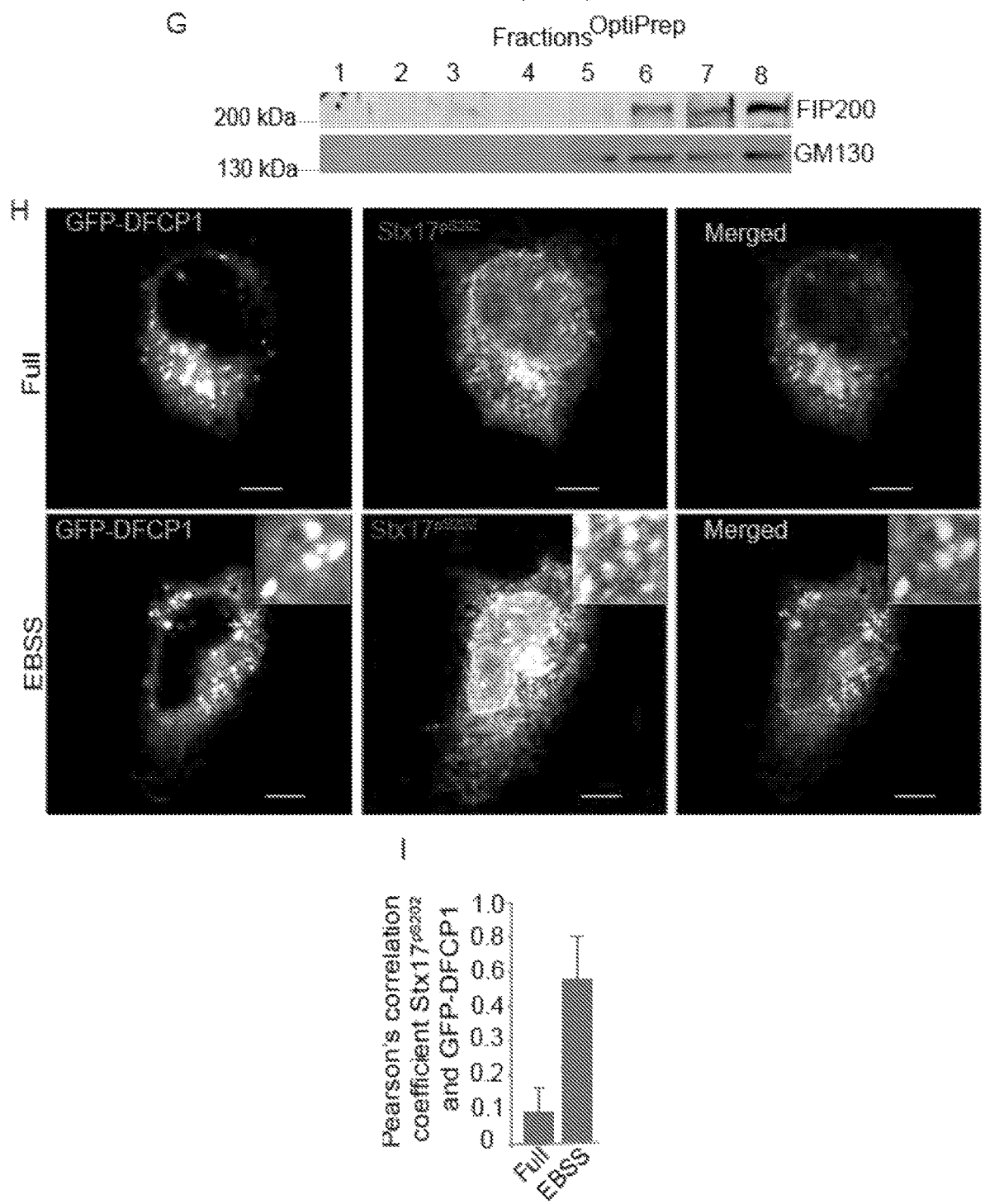

FIG. 11 (related to FIG. 4 and FIG. 5) shows that Stx17pS202 colocalizes with mPAS. (A) HC images illustrating the effect of complementation Stx17KO cells with FLAG Stx17WT, Sx17S202A and Stx17S202D. Masks: white; FLAG positive cells selected by the machine, red; ATG13 dots in FLAG transfected cells (merged images). Black and white images show unmasked epifluorescence images. White masks, algorithm-defined FLAG positive cells (primary objects); red masks, computer-identified ATG13 dots in FLAG positive cells. (B, C) Confocal microscopy to analyze the effect of complementation of Stx17KO cells with FLAG Stx17WT, Stx17S202A and Stx17S202D on formation of ATG13 (B) or FIP200 (C) dots. Scale bar 5 μm. (D) Confocal microscopy analysis of colocalization between ATG13 and Stx17pS202 in mouse BMMs. Scale bar 5 μm. (E) Confocal microscopy to analyze the colocalization between GFP-ULK1 in and Stx17pS202 in HeLa cells grown in full media. Scale bar 5 μm. (F) 293T cells were subjected to differential centrifugation and 25 k samples were layered on Optiprep gradients as described in materials and methods. Optiprep fractions were subjected to immunoblotting to analyze co-fractionation of FIP200 with Golgi marker GM130. (G) Confocal microscopy analysis of colocalization between Stx17pS202 and ULK-GFP in HeLa cell grown in full media. Scale bar 5 μm. (H) Confocal microscopy analysis of colocalization between GFPDFCP1 and Stx17pS202 in HeLa cells. Cells were left in full media (upper row) or incubated with EBSS for 1h (lower row). Arrows indicate Stx17pS202 and GFP-DFCP1 dots overlapping with each other. Scale bar 5 μm. (I) Pearson's correlation coefficient (>20 cells) of colocalization between GFP-DFCP1 and Stx17pS202.

Figure 12:
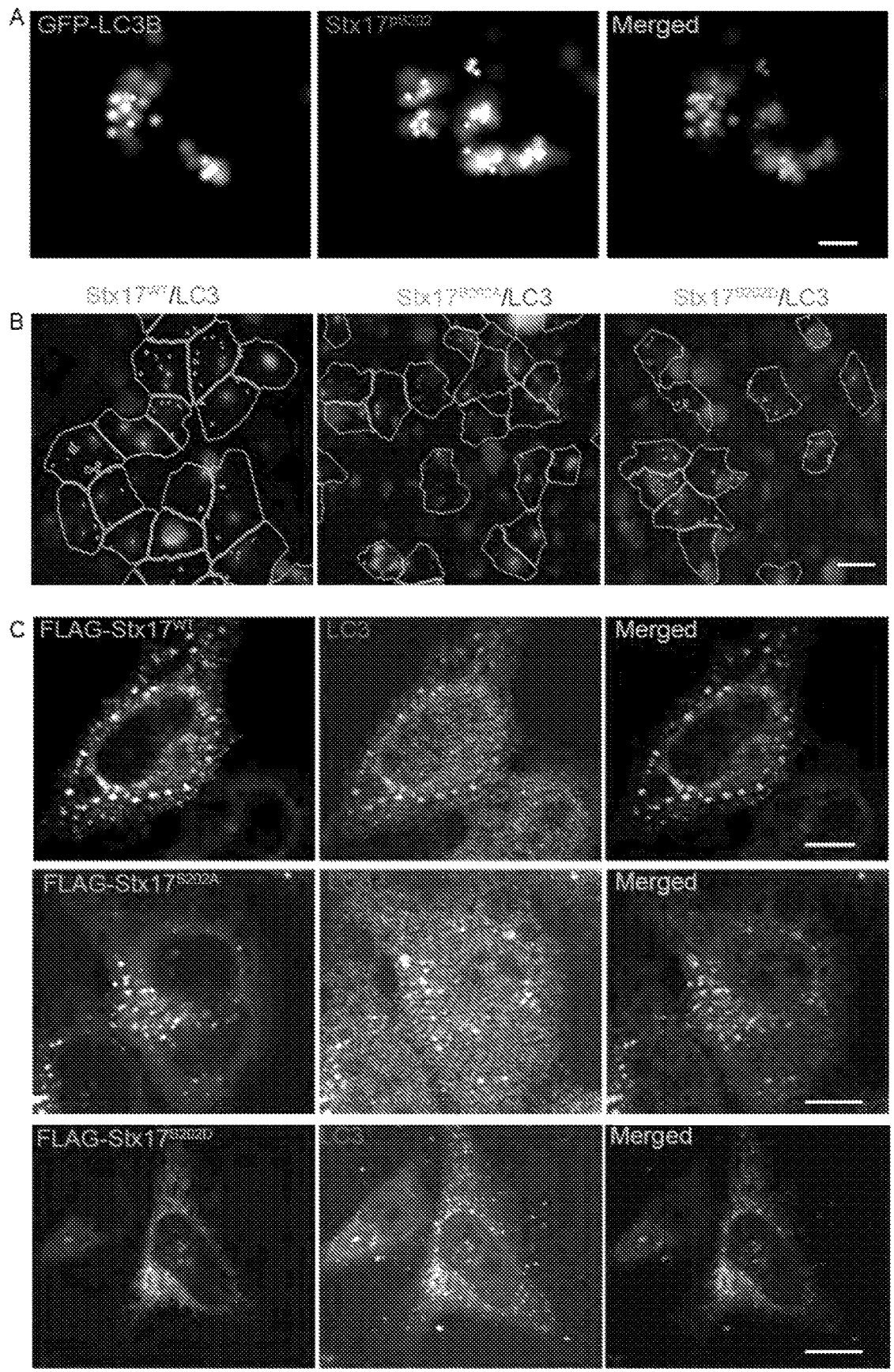
Figure 12:
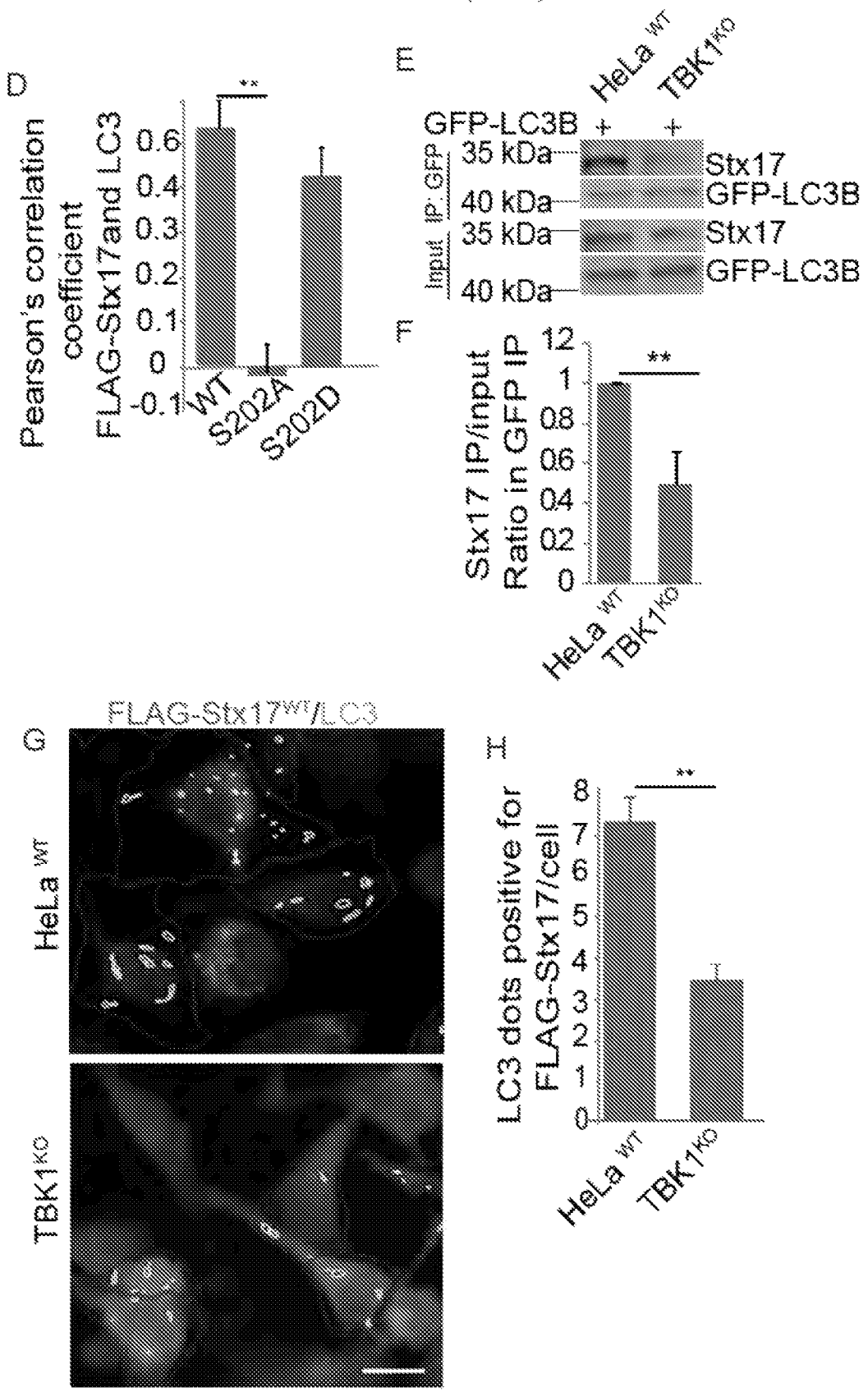

FIG. 12 (related to FIG. 6) show that WT and phosphomimetic but not non-phosphorylatable Stx17 colocalizes with LC3. (A) Super-resolution microscopy to analyze the colocalization between GFP-LC3B and $Stx17_{pS202}$ in HeLa cells incubated with EBSS for 2h. Scale bar 500 nm. (B) HC microscopy to analyze colocalization between FLAG-tagged $Sx17_{WT}$, $Stx17_{S202A}$ or $Stx17_{S202D}$ mutants with LC3 in cell induced for autophagy with starvation, Scale bar 10 μm. White masks, algorithm defined FLAG-Stx17 positive cells (primary objects); yellow masks, computer-identified overlap between FLAg-Stx17 and LC3; red, LC3. FLAG-dots. (C) Confocal Microscopy to analyze colocalization between FLAG-tagged $Stx17_{WT}$, $Stx17_{S202A}$ or $Stx17_{S202D}$ mutants with LC3 in cell induced for autophagy with starvation. Scale bar 5 μm. (D) Graph showing Pearson's correlation coefficient of colocalization between FLAG-tagged Stx17 variants and LC3. (E, F) Co-IP analysis and quantifications of interactions between Stx17 and GFP-LC3B in $HeLa_{WT}$ or $TBK1_{KO}$ cells. $p<0.05$; , $p<0.01$, (n=3) test. (G,H) HC analysis and quantifications of colocalization between FLAG-Stx17 and LC3 in $HeLa_{WT}$ or $TBK1_{KO}$ cells induced for autophagy by incubating with EBSS for 1h. Blue masks, algorithm-defined FLAG-Stx17 positive cells (primary objects); yellow masks, computer-identified overlap between FLAg-Stx17 and LC3. $p<0.05$; , $p<0.01$, (n=3) t-test.

Figure 13:
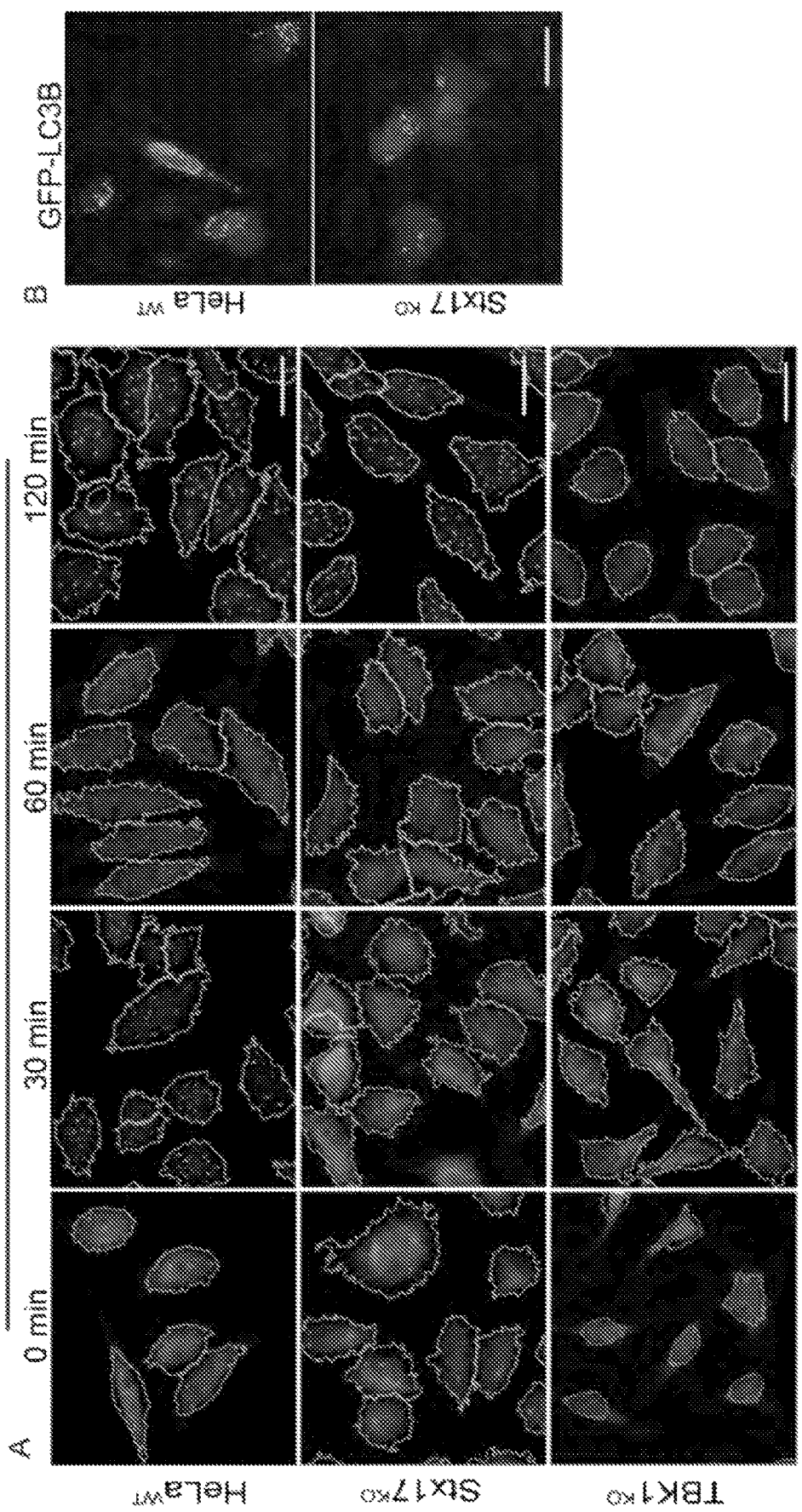
Figure 13:
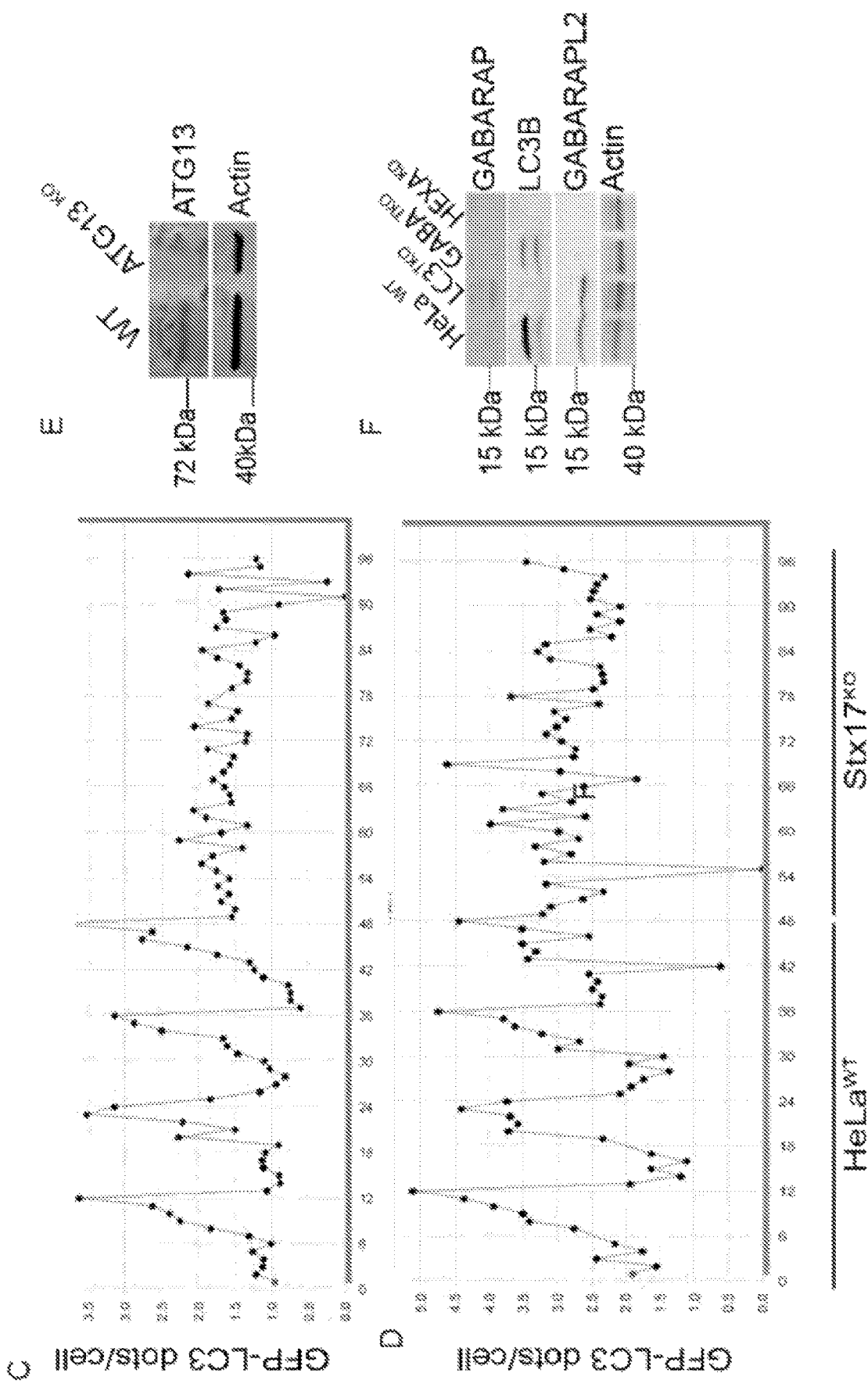

FIG. 13 (related to FIG. 7) shows that Stx17 regulates autophagy initiation (A) HC microscopy to analyze the effect of Stx17 and TBK1 knock out on LC3 puncta formation at indicated time points of autophagy induction by starvation. White masks, algorithm defined cell boundaries (primary objects); green masks, computer-identified LC3 dots. (B) High content images showing effect of Stx17 knock out on GFP-LC3 puncta formation after 1h autophagy induction with EBSS. White masks, algorithm-defined GFP-LC3 positive cells (primary objects); green masks, computer-identified GFP-LC3B dots. (C, D) Screenshots of layout of the plates used in FIGS. 7 and S7B, showing effect of Stx17 knock outs (right half of the plates) on formation of GFP-LC3B puncta. (E) Western blot showing ATG13 knock out in HeLa cells. (F) Western blot confirming LC3B, GABRAP and GABARAPL2 knock outs in mATG8s knock out cells.

DETAILED DESCRIPTION OF THE INVENTION

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound disclosed herein and includes tautomers, regioisomers, geometric isomers as applicable, and also where applicable, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation of autophagy within the context of a particular treatment or alternatively, the effect of a bioactive agent which is coadministered with the autophagy modulator (autotoxin) in the treatment of disease.

The terms "treat", "treating", and "treatment", etc., as used herein, refer to any action providing a benefit to a patient at risk for or afflicted by an autophagy mediated disease state or condition as otherwise described herein. The benefit may be in curing the disease state or condition, inhibition its progression, or ameliorating, lessening or suppressing one or more symptom of an autophagy mediated disease state or condition. Treatment, as used herein, encompasses both prophylactic and therapeutic treatment.

The term "modulator of autophagy", "regulator of autophagy" or "autostatin" is used to refer to a compound which functions as an agonist (inducer or up-regulator) or antagonist (inhibitor or down-regulator) of autophagy. Depending upon the disease state or condition, autophagy may be upregulated (and require inhibition of autophagy for therapeutic intervention) or down-regulated (and require upregulation of autophagy for therapeutic intervention). In most instances, in the case of cancer or autoimmune treatment with a modulator of autophagy as otherwise described herein, the autophagy modulator is often an antagonist of autophagy. In the case of cancer, the TPK-1 inhibitor or a Syntaxin 17 phosphorylation inhibitor may be used alone or in combination with an additional antagonist (inhibitor) of autophagy and/or an additional anticancer agent, which may be used alone or in further combination with an autophagy agonist.

The following compounds have been identified as autophagy modulators according to the present invention and can be used in the treatment of an autophagy mediated disease state or condition as otherwise described herein. It is noted that an inhibitor of autophagy is utilized where the disease state or condition is mediated through upregulation or an increase in autophagy which causes the disease state or condition and an agonist of autophagy is utilized where the disease state or condition is mediated through downregulation or a decrease in autophagy. The following compounds have been identified as autophagy modulators (autotaxins) in autophagy assays: flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, ambroxol, norcyclobenzaprine, diperodon, nortriptyline, benzethonium, niclosamide, monensin, berberine, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceflazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene and mixtures thereof and their pharmaceutically acceptable salts show activity as agonists or inducers of autophagy in the treatment of an autophagy-mediated disease, whereas tetrachlorisophthalonitrile, phenylmercuric acetate, JQ1, 2-methoxyestradiol, 3-methyladenine (3MA), epigallocatechin gallate (EGCG), 3BDO, 5-aminolevulinic acid, 5-azacytidine, 6-thioguanine, A-317491, A-867744, ABT-737, ABT-751, aceglutamide, acetazolamide, afatinib, capsaicin, actigenin, ascorbic acid, curcumin, resveratrol, SP600125, U0126, Baliomycin A1, chloroquine, LY294002, SB202190, SB203580, SC79, autophinib, wortmannin, crocin, harmines, mangiferin, and their pharmaceutically acceptable salts, find use as antagonists or inhibitors of autophagy and can be readily combined with a TBK-1 inhibitor and/or a Syntaxin 17 phosphorylation inhibitor as described herein in the treatment of cancer and/or an autoimmune disease such as rheumatoid arthritis, malaria, antiphospholipid antibody syndrome, lupus, chronic urticarial, Sjogren's disease, autoimmune-related Type 1 diabetes, rheumatoid arthritis (RA), psoriasis/psoriatic arthritis, multiple sclerosis, inflammatory bowel disease (LBD) including Crohn's disease and ulcerative colitis, Addison's disease, Grave's disease, Hashimoto's thyroiditis, Myasthenia gravis, autoimmune vasculitis, pernicious anemia and celiac disease. All of these compounds will find use as modulators of autophagy in the treatment of cancer, with the antagonists being preferred in such treatment (although inhibitors may be used alone, or in combination with the agonists) and in the case of the treatment of cancer, the inhibitors described above are preferred, alone or in combination with an autophagy agonist as described above and/or an additional anticancer agent as otherwise described herein.

Other compounds which may be used in combination with the autophagy modulators which are described above, include for example, other "additional autophagy modulators" or "additional autostatins" which are known in the art. These can be combined with one or more of the autophagy modulators which are disclosed above to provide novel pharmaceutical compositions and/or methods of treating autophagy mediated disease states and conditions which are otherwise described herein. These additional autophagy modulators include benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene, pharmaceutically acceptable salts and mixtures thereof.

The term "co-administration" or "combination therapy" is used to describe a therapy in which at least two active compounds in effective amounts are used to treat an autophagy mediated disease state or condition as otherwise described herein, especially cancer either at the same time or within dosing or administration schedules defined further herein or ascertainable by those of ordinary skill in the art. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes an administration in which one active agent (especially a TBK-1 inhibitor autophagy modulator or inhibitor of Syntaxin 17 phosphorylation) is administered at approximately the same time (contemporaneously), or from about one to several minutes to about 24 hours or more than the other bioactive agent coadministered with the TBK-1 and/or Syntaxin 17 phosphorylation inhibitor (which may be one or more of an additional autophagy inhibitor, and autophagy agonist and an anticancer agent). The additional bioactive agent may be any bioactive agent, but is generally selected from an additional autophagy mediated compound (especially an autophagy inhibitor, although an autophagy agonist may also be used in certain instances), an additional anticancer agent, or another agent, such as a mTOR inhibitor such as pp242, rapamycin, envirolimus, everolimus or cidaforollimus, among others including epigallocatechin gallate (EGCG), caffeine, curcumin or reseveratrol (which mTOR inhibitors may find use as enhancers of autophagy using the compounds disclosed herein and in addition, in the treatment of cancer with an autophagy modulator (inhibitor) as described herein, including in combination with tetrachlorisophthalonitrile, phenylmercuric acetate, JQ1, 2-methoxyestradiol, 3-methyladenine (3MA), 3BDO, 5-aminolevulinic acid, 5-azacytidine, 6-thioguanine, A-317491, A-867744, ABT-737, ABT-751, aceglutamide, acetazolamide, afatinib, capsaicin, actigenin, ascorbic acid, everolimus, SP600125, U0126, Baliomycin A1, chloroquine, LY294002, SB202190, SB203580, SC79, autophinib, wortmannin, crocin, harmines, mangiferin, and their pharmaceutically acceptable salts which are inhibitors of autophagy. It is noted that in the case of the treatment of cancer and autoimmune diseases as otherwise described herein, the use of an autophagy inhibitor is preferred, alone or in combination with an autophagy inducer (agonist) as otherwise described herein and/or a mTOR inhibitor as described above. In certain embodiments, an mTOR inhibitor selected from the group consisting of pp242, rapamycin, envirolimus, everolimus, cidaforollimus, epigallocatechin gallate (EGCG), caffeine, curcumin, reseveratrol and mixtures thereof may be used as the additional bioactive agent (along with the TBK-1 and/or inhibitor of Syntaxin 17 phosphorylation), alone or in combination with one or more additional bioactive agents, including, for example digoxin, xylazine, hexetidine, sertindole and mixtures thereof, the combination of such agents being effective as autophagy modulators in combination.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, stomach and thyroid; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, thyroid, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia. mouth/pharynx, oesophagus. larynx, kidney cancer and lymphoma, among others, which may be treated by one or more compounds according to the present invention. Because of the activity of the present compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer, a recurrent cancer or a drug resistant cancer, especially including a drug resistant cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor). Thus, the present invention is generally applicable and may be used to treat any cancer in any tissue, regardless of etiology. In the present invention, TPK-1 inhibitors and/or Syntaxin 17 phosphorylation inhibitors often are used in conjunction with additional bioactive agents, including additional autophagy modulators (including additional autophagy inhibitors as described herein), additional anticancer agents or alternative cancer therapies, such as radiation therapy, surgery, hormone therapy, immunotherapy, targeted therapy, heat or oxygenation therapy.

The term "tumor" is used to describe a malignant or benign growth or tumefacent.

The term "additional anti-cancer compound", "additional anti-cancer drug" or "additional anti-cancer agent" is used to describe any compound (including its derivatives) which may be used to treat cancer. The "additional anti-cancer compound", "additional anti-cancer drug" or "additional anti-cancer agent" can be an anticancer agent which is distinguishable from a CIAE-inducing anticancer ingredient such as a taxane, vinca alkaloid and/or radiation sensitizing agent otherwise used as chemotherapy/cancer therapy agents herein. In many instances, the co-administration of another anti-cancer compound according to the present invention results in a synergistic anti-cancer effect. Exemplary anti-cancer compounds for co-administration with formulations according to the present invention include anti-metabolites agents which are broadly characterized as antimetabolites, inhibitors of topoisomerase I and II alkylating agents and microtubule inhibitors (e.g., taxol), as well as tyrosine kinase inhibitors (e.g., surafenib), EGF kinase inhibitors (e.g., tarceva or erlotinib) and tyrosine kinase inhibitors or ABL kinase inhibitors (e.g. imatinib).

Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol), among others. Exemplary anticancer compounds for use in the present invention may include everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan. IL3-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid,N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-15-(methylsulfonylpiperadinemethyl)-indolylj-quinolone, vatalanib, AG-013736, AVE-0005, the acetate salt of [D-Ser(But)6, Azgly 10](pyro-Glu-His-Trp-Ser-Tyr-D-Ser(But)-Leu-Arg-Pro-Azgly-NH$_2$ acetate [$C_{59}H_{84}N_{18}O_{14}$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGP antibody erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SUS416, SU6668, EMD121974, interleukin-12, IM862, angiostatin, vitaxin, droloxifene, idoxyfene, spironolactone, finasteride, cimitidine, trastuzumab, denileukin diftitox, gefltinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others. Other anticancer agents which may be used in combination include immunotherapies such ipilimumab, pembrolizumab, nivolumab, alemtuzumab, atezolizumab, ofatumumab, novolumab, pembrolizumab, and rituximab, among others.

Co-administration of one of the formulations of the invention with another anticancer agent will often result in a synergistic enhancement of the anticancer activity of the other anticancer agent, an unexpected result. One or more of the present formulations comprising an autophagy modulator (autostatin) may also be co-administered with another bioactive agent (e.g., additional anticancer agents, alternative autophagy modulators, especially including autophagy inhibitors), among others as otherwise described herein).

The term "autoimmune disease" is used to describe a disease or condition arising from an abnormal immune response to normal body tissue. Virtually any body tissue can be involved in or associated with an autoimmune disease. Exemplary autoimmune diseases which are treated by the present invention include rheumatoid arthritis, malaria, antiphospholipid antibody syndrome, lupus, chronic urticarial, Sjogren's disease, autoimmune-related Type I diabetes, rheumatoid arthritis (RA), psoriasis/psoriatic arthritis, multiple sclerosis, inflammatory bowel disease (IBD) including Crohn's disease and ulcerative colitis, Addison's disease, Grave's disease, Hashimoto's thyroiditis, Myasthenia gravis, autoimmune vasculitis, pernicious anemia and celiac disease.

According to various embodiments, the compounds according to the present invention (TBK-1 inhibitors, compounds that inhibit phosphorylation of Syntaxin 17 such as AG 1478 and AG 1024 and anti-Syntaxin 17 antibodies and optionally, other bioactive agents, when combined with one or more TBK-1 inhibitors, inhibitors of Syntaxin 17 phosphorylation and/or anti-Syntaxin 17 antibodies which can be delivered into cells) may be used for treatment or prevention purposes in the form of a pharmaceutical composition. This pharmaceutical composition may comprise one or more active ingredients as described herein.

As indicated, the pharmaceutical composition may also comprise a pharmaceutically acceptable excipient, additive or inert carrier. The pharmaceutically acceptable excipient, additive or inert carrier may be in a form chosen from a solid, semi-solid, and liquid. The pharmaceutically acceptable excipient or additive may be chosen from a starch, crystalline cellulose, sodium starch glycolate, polyvinylpyrolidone, polyvinylpolypyrolidone, sodium acetate, magnesium stearate, sodium laurylsulfate, sucrose, gelatin, silicic acid, polyethylene glycol, water, alcohol, propylene glycol, vegetable oil, corn oil, peanut oil, olive oil, surfactants, lubricants, disintegrating agents, preservative agents, flavoring agents, pigments, and other conventional additives. The pharmaceutical composition may be formulated by admixing the active with a pharmaceutically acceptable excipient or additive.

The pharmaceutical composition may be in a form chosen from sterile isotonic aqueous solutions for intravenous, intramuscular, intrathecal or intratumor injection, pills, drops, pastes, cream, spray (including aerosols), capsules, tablets, sugar coating tablets, granules, suppositories, liquid, lotion, suspension, emulsion, ointment, gel, and the like. Administration route may be chosen from subcutaneous, intravenous, intrathecal, intratumor (i.e., directly into the tumorous tissue to be treated which is preferred in certain solid tumors), intestinal, parenteral, oral, buccal, nasal, intramuscular, transcutaneous, transdermal, intranasal, intraperitoneal, by inhalation and topical. The pharmaceutical compostions may be immediate release, sustained/controlled release, or a combination of immediate release and sustained/controlled release depending upon the compound(s) to be delivered, the compound(s), if any, to be coadministered, as well as the disease state and/or condition to be treated with the pharmaceutical composition. A pharmaceutical composition may be formulated with differing compartments or layers in order to facilitate effective administration of any variety consistent with good pharmaceutical practice.

The subject or patient may be chosen from, for example, a human, a mammal such as domesticated animal, or other animal. The subject may have one or more of the disease states, conditions or symptoms associated with autophagy as otherwise described herein.

The compounds according to the present invention may be administered in an effective amount to treat or reduce the likelihood of an autophagy-mediated disease and/or condition as well one or more symptoms associated with the disease state or condition, especially cancer. One of ordinary skill in the art would be readily able to determine an effective amount of active ingredient by taking into consideration several variables including, but not limited to, the animal subject, age, sex, weight, site of the disease state or condition in the patient, previous medical history, other medications, etc.

For example, the dose of an active ingredient which is useful in the treatment of an autophagy mediated disease state, condition and/or symptom such as cancer for a human patient is that which is an effective amount and may range from as little as 100 μg or even less to at least about 500 mg to a gram or more, which may be administered in a manner consistent with the delivery of the drug and the disease state or condition to be treated. In the case of oral administration, active is generally administered from one to four times or more daily. Transdermal patches or other topical administration may administer drugs continuously, one or more times a day or less frequently than daily, depending upon the absorptivity of the active and delivery to the patient's skin. Of course, in certain instances where parenteral administration represents a favorable treatment option, intramuscular administration or slow IV drip may be used to administer active. The amount of active ingredient which is administered to a human patient preferably ranges from about 0.05 mg/kg to about 25 mg/kg, 0.075 mg/kg to about 10 mg/kg, about 0.1 mg/kg to about 7.5 mg/kg, about 0.25 mg/kg to about 6 mg/kg., about 1.25 to about 5.7 mg/kg.

The dose of a compound according to the present invention may be administered at the first signs of the onset of an autophagy mediated disease state, condition or symptom such as cancer. For example, the dose may be administered for the purpose of inhibiting cancer growth, increasing the likelihood of remission of cancer, reducing the likelihood of metastatis and/or recurrence of cancer. The dose of active ingredient may be administered at the first sign of relevant symptoms prior to diagnosis, but in anticipation of the disease or disorder or in anticipation of decreased bodily function or any one or more of the other symptoms or secondary disease states or conditions associated with an autophagy mediated disorder to condition.

The term "TBK-1" or "Tank Binding Kinase 1" or "Serine Threonine Protein Kinase TBK-1" (UnitprotKB-Q9UHD2) is an enzyme with kinase activity. More specifically, TBK-1 is a serine threonine protein kinase. It is encoded by the TBK1 gene in humans. This kinase is mainly known for its role in innate immunity antiviral response. However, TBK1 also regulates cell proliferation, apoptosis, autophagy, and anti-tumor immunity. Pursuant to the present invention TBK-1 phosphorylates Syntaxin17 at amino acid residue serine 202 and this reaction can be used to identify autophagy inhibitors which are useful in the treatment of cancer and/or autoimmune diseases. Preferably, in the present invention, TBK-1 refers to human TBK-L.

The term "Syntaxin 17" or "Stx17" is used to describe an autophagy factor which is phosphorylated by TBK1. The interaction of Stx17 and TBK1 is reflected in phosphorylation of Stx17 by TBK1 and modulation of its function. Surprisingly, these interactions and phosphorylation of Stx17 by TBK1 occur at the earliest stages of autophagy, i.e. at its initiation. The present inventors demonstrate that phosphorylation of Stx17 is important for assembly of the ULK1 complex and that it is critical for autophagy initiation. Pursuant to the present invention, the inventors show that phosphorylated Stx17 and components of the ULK1 complex, localized to the Golgi in the resting state, respond to induction of autophagy by translocating from the Golgi to participate in the formation of mPAS during autophagy initiation. Accordingly, the present invention provides assays and methods for discovering compounds of unknown activity which inhibit phosphorylation of Stx17 and consequently provide activity as inhibitors of autophagy and potential therapeutic agents for the treatment of autophagy diseases and conditions which require phosphorylation of Stx17 for initiation. Preferably, in the present invention Syntaxin 17 refers to human Syntaxin 17.

The full human Syntaxin 17 amino acid sequence is as follows:

1 msedeekvkl rrlepaiqkf ikivipidle rirkhqinie kyqrcriwdk iheehinagr 61 tvqqlrsnir eieklclkvr kddlvllkrm idpvkeeasa ataeflqlhl esveelkkqf 121 ndeetllqpp ltrsmtvgga fhtteaeass qsltqiyalp eipqdqnaae swetleadli 181 elsqlvtdfs llvnsqqeki dsiadhvnsa avnveegtkn lgkaakykla alpvagalig 241 gmvggpigll agfkvagiaa algggvlgft ggkligrkkq kmmekltssc pdlpsqtdkk 301 cs (SEQIDNO:1)

The following sequences may be used to generate phosphorylated synthetic peptides which can be used to provide antibodies (monoclonal or polyclonal) which bind to Stx17$^{pS02}$ and can be used in assays and methods for identifying inhibitors of Stx17 phosphorylation and the initiation of autophagy. These inhibitors are potential therapeutic agents for the treatment of disease states and/or conditions which are mediated through autophagy and initiated by phosphorylation of Stx17.

In embodiments, a phosphorylated peptide according to a portion of the peptide sequence:

ELSQLVTDFSLLVNSQQEKIDSIADHVNSAAVNVEEGT (SEQIDNO:2). This sequence represents amino acid residues 181-218 of human Syntaxin 17 (serine 202 is found in the sequence DSIADH, SEQIDNO:4 and is phosphorylated in peptides used to raise antibodies). In embodiments a 10-30 mer, preferably a 10-25 mer, even more preferably a 15-25 mer or a 15-20 mer consisting of contiguous amino acids of SEQ ID NO: 2 which contain at least the peptide DSIADH (SEQIDNO:4) within SEQIDNO:2 and which is phosphorylated at Serine 202 (the Serine residue of DSIADH), is used to generate monoclonal and polyclonal capture antibodies which are used in assays according to the present invention to bind to Syntaxin17$^{pS02}$. Alternatively, the amino acid sequence ELSHLVTDMSLLVSSQQEKIDSIADHVNSAAVNVEEGT (SEQIDNO:3) which represents amino acid residues 181-218 of mouse/rat Syntaxin 17-serine 202 is found in sequence DSIADH (SEQIDNO:4) and is phosphorylated at the amino acid corresponding to Serine 202 in Syntaxin 17 in peptides used to raise antibodies against (the Serine residue of DSIADH SEQIDNO:4). In embodiments a 10-30 mer, preferably a 10-25 mer, even more preferably a 15-25 mer or a 15-20 mer consisting of the amino acids of SEQ ID NO: 3 which contain at least the peptide DSIADH (SEQIDNO:4) within SEQIDNO:3 which is phosphorylated at the serine in DSIADH (SEQIDNO:4) corresponding to Serine 202 of Syntasxin 17, is used to generate monoclonal and polyclonal antibodies. Phosphorylated peptides as described above which are used to raise antibodies to Syntaxin 17$^{pS02}$ are prepared by peptide chemical synthetic means which are well known in the art. The synthesis may incorporate phosphorylated serine as a reactant into the amino acid sequence during synthesis or alternatively, the peptide may be readily phosphorylated at the serine corresponding to serine 202 in the peptide after synthesis by chemical or enzymatic means well known in the art. Once obtained, the phosphorylated peptide are used to raise antibodies (monoclonal or polyclonal) using standard techniques which are well known in the art.

In embodiments, the present invention utilizes antibodies (e.g. as created using the standard methods described above) which bind to $Stx17^{pS02}$. These antibodies are used in the present invention to identify inhibitors of Stx17 phosphorylation (which occurs at amino acid residue Serine 202 of Syntaxin 17). These anti-$Stx17^{pS02}$ antibodies are relatively easy to prepare using techniques which are well known in the art. In particular, these methods are identified and described in, for example, Attard, et al., *Int. J. Pept. Res. Ther.* (2007) 13:447-468. This reference describes methods for the production of phosphorylated peptides which may be used to raise antibodies which bind to $Stx17^{pS02}$ and are useful in assays according to the present invention. These assays may be used to identify compounds of unknown activity as inhibitors of Syntaxin 17 phosphorylation, autophagy initiation and treatment of cancer and autoimmune diseases as otherwise described herein.

In an embodiment, a method for identifying a potential inhibitor of phosphorylation of Stx17 relies on an assay, preferably an immunoassay assay, which provides conditions which express TBK1 and Syntaxin 17 and the phosphorylation by TBK1 of Syntaxin 17 to produce $Stx17^{pS02}$ (phosphorylation occurs at serine amino acid residue 202 of Syntaxin 17) as an analyte. In certain embodiments, this assay is a cell based assay in part and the cells express TBK1 and Syntaxin 17 to produce phosphorylated Syntaxin 17, or alternatively, the assay is conducted in vitro (e.g. as a cell lysate). Pursuant to this method, the expression of TBK1 and Syntaxin 17 in the absence of testing compound (often in a cell lysate, but also in a whole cell) results in the phosphorylation of Syntaxin 17 at serine residue 202 ($Stx170^{20}$). $Stx17^{pS02}$ is identified by exposure of $Stx17^{pS02}$ to a monoclonal or polyclonal capture antibody which specifically binds to Stx17P (an anti-$Stx17^{pS02}$ capture antibody, prepared as described above) and preferably, a second antibody as a monoclonal or polyclonal detection antibody which comprises a reporter (preferably a conjugated reporter comprising a fluorescent moiety, quantum dots or gold nanoparticles) which binds to the anti-$Stx17^{pS02}$ antibody. Alternatively, the anti-$Stx17^{pS02}$ antibody may itself contain a reporter which elicits a signal. In embodiments, the binding of the second antibody comprising a reporter to the anti-$Stx17^{pS02}$ antibody identifies Stx17 phosphorylation ($Stx17^{pS02}$) by virtue of the conjugated reporter and the signal emitted from the reporter. The second antibody may be specific to $Stx17^{pS02}$ in a region other than the phosphorylation region (which contains amino acid residue 202) or alternatively and preferably, is specific for the first (capture) antibody, such that binding to the first antibody will occur and emit a signal associated with the report to which the second antibody is conjugated. Secondary antibodies which bind to primary antibodies are well known in the art. The phosphorylation of Syntaxin 17 by TBK-1 and optionally the testing of the test compound may be performed within whole cells, but preferably the whole cells are lysed and then exposed to capture antibody and detection antibody in vitro (preferably as a cell lysate). Alternatively the entire assay may be conducted in cells, but preferably, the assay is conducted entirely in vitro (e.g. cell lysate) for rapid testing of test compounds. In preferred aspects of the assay, if no signal is emitted after introduction of a compound of unknown activity, the compound has prevented phosphorylation of Stx17 and is an inhibitor of Stx17 phosphorylation and a potential therapeutic agent for the treatment of cancer or an autoimmune disease as described herein.

Pursuant to the present invention, the cells which exhibit Stx17 phosphorylation (by virtue of emission of a signal from the report on the second antibody) are exposed to a test compound and the absence or substantial reduction of anti-$Stx17^{pS02}$ antibody in the sample which has been analyzed evidences that the compound is an inhibitor of Stx17 phosphorylation (because little or no phosphorylation occurred) and a potential agent for use as an autophagy modulator for the treatment of cancer. The presence of a signal from the reporter evidences that phosphorylation of Stx17 occurred and the test compound is not an inhibitor of Stx17 phosphorylation. The intensity of the signal from the reporter may evidence that the test compound is a partial inhibitor or a full inhibitor. The signal emitted may be compared to a standard which evidences the activity of the test compound. The reporter may be a fluorescent moiety or other moiety which elicits a measurable signal which can identify the concentration of $Stx17^{pS02}$ in a sample. The reporters which may be used in assays according to the present invention are described in detail herein.

Assays according to the present invention comprise a cell or cell lysate which expresses both TBK1 and Syntaxin 17 and has the ability to phosphorylate Syntaxin 17 to $Stx17^{pS02}$ in the absence of an inhibitor. The assay also comprises an anti-$Stx17^{pS02}$ capture antibody (monoclonal or polyclonal) capable of binding to $Stx17^{pS02}$ and a second detection antibody (monoclonal or polyclonal) which binds to the anti-$Stx17^{pS02}$ antibody and comprises a reporter which can elicit a signal in order to measure the amount of anti-$Stx17^{pS02}$ antibody which is bound to the phosphorylated Syntaxin17. The signal elicited from the reporter may be compared with a standard which could represent little or no inhibition of Stx17 phosphorylation (based upon the strength of the emitted signal) using the same or similar assays methods or an absence of inhibition of Stx17 phosphorylation (no signal) using the same or similar assays methods used to identify the activity of the compound as a potential inhibitor of Syntaxin 17 phosphorylation. Standards and their use in assays are well known in the art.

The term "expression vector" is used to describe any vector or nucleic acid construct which expresses TBK-1 or Syntaxin17 for use in methods and assays pursuant to the present invention. An expression vector or construct, is generally a plasmid or virus designed for gene expression in cells and in vitro (cell-free). The vector may be a non-integrating or integrating vector preferably selected from the group consisting of a plasmid, a circle DNA vector (episomal DNA), a lentiviral vector, an inducible lentiviral vector or a retroviral vector, among other components, wherein each vector preferably comprises genes to express TBK-1 and/or Syntaxin 17. Collectively, these expression vectors are referred to as "expression components". The vector is often used to introduce a specific gene into a target cell, and can commandeer the cell's mechanism for protein synthesis to produce the protein encoded by the gene. Expression vectors are basic tools for the production of proteins and can be used to generate proteins in vivo and in vitro. Expression vectors are well known in the art and can readily be used to generate proteins intracellularly or in a cell free (in vitro) environment. Many of these vectors are available commercially. Protein expression vectors are well known in the art and may be readily adapted to provide components which can be used to express TBK-1 and Syntaxin 17 within whole cells or in vitro to allow phosphorylation of Syntaxin 17 by TBK-1. These vectors are incorporated into assays (in whole cells or in cell lysates) for identifying inhibitors of Syntaxin 17 phosphorylation by TBK-1 which the present invention identifies as being a critical step in the initiation of autophagy. These inhibitors of Syntaxin 17 phosphorylation may be used as therapeutic agents for the treatment of cancer and/or autoimmune diseases as described herein.

As used herein, "antibody" includes, but is not limited to, monoclonal antibodies and polyclonal antibodies The following disclosure from U.S. Patent Application Document No. 20100284921, the entire contents of which are hereby incorporated by reference, exemplifies techniques that are useful in making antibodies employed in formulations of the instant invention.

The term "anti-Stx17$^{pS02}$ antibody" is used to describe a monoclonal or polyclonal antibody (capture antibody) which specifically binds to human Stx17 which has been phosphorylated at serine 202 by TBK1. In certain embodiments, anti-Stx17$^{pS02}$ antibody is a monoclonal antibody (e.g. an anti-human mouse monoclonal antibody, anti-human rabbit monoclonal antibody, etc.) or a polyclonal antibody (e.g. an anti-human mouse polyclonal antibody or an anti-human rabbit polyclonal antibody). In embodiments, the anti-Stx17$^{pS02}$ antibody may comprise a conjugated reporter (detection antibody). In embodiments, a second antibody (detection antibody) which is conjugated to a reporter is used to bind to the anti-Stx17$^{pS02}$ antibody to determine how extensively Stx17 has been phosphorylated. Thus, upon phosphorylation by TBK1, Stx17$^{pS02}$ binds to the anti-Stx17$^{pS02}$ antibody (capture antibody) and the capture antibody binds to the detection antibody which elicits a signal and evidences the extent of phosphorylation of Stx17 by TBK1. In the presence of a compound of unknown activity, inhibition of phosphorylation of Stx17 by TBK1 will be evidenced by a low signal or the absence of a signal from the detection antibody. Absence of inhibition (no activity) or low inhibitory activity will be evidenced by a substantial signal. The signals elicited in the assay are often compared to a standard such that a low level or absence of signal evidences that a test compound is an inhibitor of phosphorylation of Stx17 by TBK1 and a potential therapeutic agent for the treatment of autophagy mediated disease states and conditions in which inhibition of autophagy provides a favorable therapeutic response (e.g. cancer or an autoimmune disease), or alternatively a high or substantial signal from the assay evidences that the compound exhibits little inhibitory activity the phosphorylation of Stx17 by TBK1 and will likely prove inactive as a potential therapeutic agent for the treatment of cancer or an autoimmune disease.

As described in U.S. Patent Application Document No. 20100284921, "antibodies . . . may be polyclonal or monoclonal. Monoclonal antibodies are preferred. The antibody is preferably a chimeric antibody. For human use, as a therapeutic agent, the antibody is preferably a humanized chimeric antibody.

An anti-target-structure antibody . . . may be monovalent, divalent or polyvalent in order to achieve target structure binding. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

The invention also includes [use of] functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application Nos. WO 1993/21319 and WO 1989/09622. Functional equivalents include polypeptides with amino acid sequences substantially the same as the amino acid sequence of the variable or hypervariable regions of the antibodies raised against target integrins according to the practice of the present invention.

Functional equivalents of the anti-target-structure antibodies further include fragments of antibodies that have the same, or substantially the same, binding characteristics to those of the whole antibody. Such fragments may contain one or both Fab fragments or the F(ab')$_2$ fragment. Preferably the antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Preferred constant regions are gamma 1 (IgG1), gamma 2 (IgG2 and IgG), gamma 3 (IgG3) and gamma 4 (IgG4). The light chain constant region can be of the kappa or lambda type.

The monoclonal antibodies may be advantageously cleaved by proteolytic enzymes to generate fragments retaining the target structure binding site. For example, proteolytic treatment of IgG antibodies with papain at neutral pH generates two identical so-called "Fab" fragments, each containing one intact light chain disulfide-bonded to a fragment of the heavy chain (Fc). Each Fab fragment contains one antigen-combining site. The remaining portion of the IgG molecule is a dimer known as "Fc". Similarly, pepsin cleavage at pH 4 results in the so-called F(ab')2 fragment.

Single chain antibodies or Fv fragments are polypeptides that consist of the variable region of the heavy chain of the antibody linked to the variable region of the light chain, with or without an interconnecting linker. Thus, the Fv comprises an antibody combining site.

Hybrid antibodies may be employed. Hybrid antibodies have constant regions derived substantially or exclusively from human antibody constant regions and variable regions derived substantially or exclusively from the sequence of the variable region of a monoclonal antibody from each stable hybridoma.

Methods for preparation of fragments of antibodies (e.g. for preparing an antibody or an antigen binding fragment thereof having specific binding affinity for either caspase-1 or an autophagy-related immunomodulatory cytokine) are either described in the experiments herein or are otherwise known to those skilled in the art. See, Goding, "Monoclonal Antibodies Principles and Practice", Academic Press (1983), p. 119-123. Fragments of the monoclonal antibodies containing the antigen binding site, such as Fab and F(ab')2 fragments, may be preferred in therapeutic applications, owing to their reduced immunogenicity. Such fragments are less immunogenic than the intact antibody, which contains the immunogenic Fc portion. Hence, as used herein, the term "antibody" includes intact antibody molecules and fragments thereof that retain antigen binding ability.

When the antibody used in the practice of the invention is a polyclonal antibody (IgG), the antibody is generated by inoculating a suitable animal with a target structure or a fragment thereof. Antibodies produced in the inoculated animal that specifically bind the target structure are then isolated from fluid obtained from the animal. Anti-target-structure antibodies may be generated in this manner in several non-human mammals such as, but not limited to, goat, sheep, horse, rabbit, and donkey. Methods for generating polyclonal antibodies are well known in the art and are described, for example in Harlow et al. (in: Antibodies, A Laboratory Manual, 1988, Cold Spring Harbor, N.Y.).

When the antibody used in the methods used in the practice of the invention is a monoclonal antibody, the antibody is generated using any well known monoclonal antibody preparation procedures such as those described, for example, in Harlow et al. (supra) and in Tuszynski et al. (Blood 1988, 72:109-115). Generally, monoclonal antibodies directed against a desired antigen are generated from mice immunized with the antigen using standard procedures as referenced herein. Monoclonal antibodies directed against full length or fragments of target structure may be prepared using the techniques described in Harlow et al. (supra).

The effects of sensitization in the therapeutic use of animal-origin monoclonal antibodies in the treatment of human disease may be diminished by employing a hybrid molecule generated from the same Fab fragment, but a different Fc fragment, than contained in monoclonal antibodies previously administered to the same subject. It is contemplated that such hybrid molecules formed from the anti-target-structure monoclonal antibodies may be used in the present invention. The effects of sensitization are further diminished by preparing animal/human chimeric antibodies, e.g., mouse/human chimeric antibodies, or humanized (i.e. CDR-grafted) antibodies. Such monoclonal antibodies comprise a variable region, i.e., antigen binding region, and a constant region derived from different species. By 'chimeric' antibody is meant an antibody that comprises elements partly derived from one species and partly derived form at least one other species, e.g., a mouse/human chimeric antibody.

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, the antibodies produced are largely human but contain antigen-binding specificities generated in mice. As demonstrated by Morrison et al., 1984, Proc. Natl. Acad. Sci. USA 81:6851-6855, both chimeric heavy chain V region exon (VH)-human heavy chain C region genes and chimeric mouse light chain V region exon (VK)-human κ light chain gene constructs may be expressed when transfected into mouse myeloma cell lines. When both chimeric heavy and light chain genes are transfected into the same myeloma cell, an intact H2L2 chimeric antibody is produced. The methodology for producing such chimeric antibodies by combining genomic clones of V and C region genes is described in the above-mentioned paper of Morrison et al., and by Boulianne et al. (Nature 1984, 312:642-646). Also see Tan et al. (J. Immunol. 1985, 135:3564-3567) for a description of high level expression from a human heavy chain promotor of a human-mouse chimeric K chain after transfection of mouse myeloma cells. As an alternative to combining genomic DNA, cDNA clones of the relevant V and C regions may be combined for production of chimeric antibodies, as described by Whitte et al. (Protein Eng. 1987, 1:499-505) and Liu et al. (Proc. Natl. Acad. Sci. USA 1987, 84:3439-3443). For examples of the preparation of chimeric antibodies, see the following U.S. Pat. Nos. 5,292,867; 5,091,313; 5,204,244; 5,202,238; and 5,169,939. The entire disclosures of these patents, and the publications mentioned in the preceding paragraph, are incorporated herein by reference. Any of these recombinant techniques are available for production of rodent/human chimeric monoclonal antibodies against target structures.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., 1986, Nature 321:522-525; Verhoeyen et al., 1988, Science 239:1534-1536; Hale et al., 1988, Lancet 2:1394-1399; Queen et al., 1989, Proc. Natl. Acad. Sci. USA 86:10029-10033). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-target structure antibodies of reduced human immunogenicity."

Further, standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, New York; Maniatis et al., 1982 Molecular Cloning, Cold Spring Harbor Laboratory, Plainview, New York; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, New York; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

High-content imaging techniques and diagnostic methods described herein can use reporters such as fluorescence-inducing compounds, e.g. a fluorescent moiety such as a fluorescein dye or a rhodamine dye. In some embodiments, the fluorescent moiety comprises two or more fluorescent dyes that can act cooperatively with one another, for example by fluorescence resonance energy transfer ("FRET"). The fluorescent moiety may be any fluorophore that is capable of producing a detectable fluorescence signal in an assay medium; the fluorescence signal can be "selfquenched" and capable of fluorescing in an aqueous medium. "Quench" refers to a reduction in the fluorescence intensity of a fluorescent group as measured at a specified wavelength, regardless of the mechanism by which the reduction is achieved. As specific examples, the quenching may be due to molecular collision, energy transfer such as FRET, a change in the fluorescence spectrum (color) of the fluorescent group or any other mechanism. The amount of the reduction is not critical and may vary over a broad range. The only requirement is that the reduction be measurable by the detection system being used. Thus, a fluorescence signal is "quenched" if its intensity at a specified wavelength is reduced by any measurable amount.

Examples of fluorophores which may be used as reporters in embodiments of the present invention include xanthenes such as fluoresceins, rhodamines and rhodols, cyanines, phtalocyanines, squairanines, bodipy dyes, pyrene, anthracene, naphthalene, acridine, stilbene, indole or benzindole, oxazole or benzoxazole, thiazole or benzothiazole, carbocyanine, carbostyryl, prophyrin, salicylate, anthranilate, azulene, perylene, pyridine, quinoline, borapolyazaindacene, xanthene, oxazine or benzoxazine, carbazine, phenalenone, coumarin, benzofuran, or benzphenalenone. Examples of rhodamine dyes include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichlorotetramethylrhodamine (dTAMRA). Examples of fluorescein dyes include, but are not limited to, 4,7-dichlorofluoresceins, 5-carboxyfluorescein (5-FAM) and 6-carboxyfluorescein (6-FAM).

For example, cells can be transfected with green fluorescent protein-tagged autophagic Syntaxin 17 marker protein (GFP-Syntaxin 17)(see e.g., Gonzalez-Polo R-A, et al. (2005) J. Cell Sci. 118:3091-3102), which is a fluorescent fusion protein that is incorporated into autophagosomes (also called autophagic vesicles, or AV); confocal microscopy can be used to score the number of autophagosomes per cell. Although this can be done using robotics and automated microscopy Detection and spatial localization in a biological sample as described herein may be based on, but not restricted to fluorescence in the ultra-violet, visible, infrared spectral regions, or may report via radiofrequencies (MRI/NMR) and well as radioactive detection. In addition, a reporter group containing heavy atoms is employed for detection using electron microscopy (EM or TEM), scanning EM (SEM) or mass spectral or equivalent techniques. In alternative embodiments, the reporter (domains or moieties) comprises functional groups that either turn off or on its reporting function from its native state, but in the presence of a biological sample (for example; pH change, presence of a specific enzyme, metal etc.) changes its state, giving further details to the biological environment in an autophagic vesicle.

In one embodiment of the invention, "sandwich" type immunoassays are utilized to measure $Stx17^{pS02}$ in a sample, preferably a blood sample, to facilitate an ease of analysis of phosphorylation inhibitor activity in the blood of a patient or subject. In one embodiment, the methods of the invention utilize a capture antibody that specifically binds to $Stx17^{pS02}$. The capture antibody may be coupled to a solid substrate or solid phase. Examples of suitable substrates include, but are not limited to, wells of microtiter plates or cuvettes, or nitrocellulose or nylon membranes. In one embodiment of the invention, the capture antibodies are coupled to paramagnetic particles in wells of microtiter plates or cuvettes. For example, biotin-coupled capture antibodies can couple to streptavidin coated paramagnetic particles via the well known avidin-biotin binding reaction. Other methods of coupling the capture antibody to the solid phase of the assays are known to those skilled in the art. Anti-$Stx17^{pS02}$ antibodies, including monoclonal antibodies are readily obtainable using methods known in the art. The use of these and/or other antibodies which are otherwise described herein or are well known in the art and may be readily adapted to the present invention.

In practicing the assay of the present invention, anti-$Stx17^{pS02}$ capture antibody may also be exposed to a detection antibody that is coupled to a detectable label, including a fluorescent moiety, quantum dots or gold nanoparticles, or as otherwise described herein. Examples of suitable labels are described above, one example of a label is an acridinium ester. Methods of coupling labels to antibodies are well known in the art. For example, acridinium, as a "sulfonyl chloride ester" can be crosslinked to the detection antibody by the reaction of the lysly moiety of the epsilon amino group of lysine in proteins, such as antibodies, to the acridinium ester. The reaction products may then be separated by size exclusion chromatography on Sepharose beads or otherwise.

In certain embodiments of the invention, the sandwich immunoassays may be chemiluminescent immunoassays, but colorimetric assays may be preferred. Monoclonal antibodies that could be used as capture and detection antibodies for $Stx17^{pS02}$ as described herein can be produced using conventional methods known in the art. See, for example. Kohler and Milstein, (1975) Nature, 256:495-97; or Sambrook et al. (2001) Molecular Cloning: A Laboratory Manual, 3rd edition, Cold Spring Harbor Laboratory Press. Briefly, animals, such as mice, are injected with an antigen, such as $Stx17^{pS02}$ or fragments thereof, that may be coupled to a carrier protein. The animals are boosted with one or more antigen injections, and are hyperimmunized by an intravenous (IV) booster about three days before fusion. Spleen cells from the mice are isolated and are fused by standard methods to myeloma cells. Hybridomas are selected in standard hypoxanthine/aminopterin/thymine (HAT) medium, according to standard methods. Hybridomas secreting antibodies which recognize different epitopes of the antigen are identified, cultured, and subcloned using standard immunological techniques. The antibodies are then screened for the desired specificity or cross reactivity using methods known in the art.

Although one embodiment of the invention employs fluorescent, colorimetric or chemiluminescent imumunoassays to practice the methods of the invention, other immunoassays, such as ELISAs and RIAs may be used. The parameters and components of the assays are determined and optimized as is well known to those skilled in the art such that the assays provide measurement of $Stx17^{pS02}$ levels in the biological samples being assayed. In addition, although certain embodiments of the invention utilize antibodies as the agents capturing $Stx17^{pS02}$, $Stx17^{pS02}$ may be captured in the assays of the invention using other chemical agents or molecules that are not antibodies. For example, such an agent may recognize amino acid profiles of $Stx17^{pS02}$ and thereby bind the $Stx17^{pS02}$ to a solid phase in a similar manner as the capture antibodies described herein.

In some embodiments of the invention, it may be desirable to automate the methods as much as practical in order to improve replicability of the results and reduce the time and costs required to conduct the assays. Automated assays used to practice the methods of the invention permit users to conduct at least about 80 tests per hour, and preferably more than about 100 test per hour.

One may also use any conventional, non-automated, assay device to practice the methods of the invention. For example, a conventional microtiter plate can be used to store the various solutions used in performing the assay. The device should permit the biological sample to be exposed to a combination of antibodies. The antibodies may recognize different epitopes of the antigen(s) being assayed. The device should also cause the bound antigen to be retained to a substrate as solutions are added and removed during the assay.

By way of example, and not by way of limitation, wells of a microtiter plate can be loaded with a solution containing streptavidin coated magnetic particles, as described herein. A solution containing biotin coupled capture antibodies (e.g., biotin coupled mAb) is added to the well to enable the coupling of the capture antibodies to the magnetic particles. A concentration of capture antibody is empirically selected (based on expected antigen concentrations) as discussed herein, to permit binding of all, or essentially all, of the test antigen that is available in the sample. In that regard, typical antigen concentrations in biological samples are in the nanogram to low microgram range (e.g. less than 1 ng/ml-5 µg/ml) so that the capture antibody concentrations are in the low to high microgram range (e.g. 1-100 µg/ml). The sample is added to the well. If the sample contains the antigens of interest (e.g., $Stx17^{pSO2}$), the antigen will bind to the capture antibodies. The plate is exposed to a magnetic field to immobilize the magnetic particles, and the solution is removed from the well; but the antigen will not be removed because it is bound to the antibodies that are bound to the magnetic particles that are immobilized by the magnetic field. A solution containing the detection antibody coupled to a label (e.g., acridinium labeled mAb) is added to the well containing the bound antigen. As indicated elsewhere herein, the concentration of the detection antibody is preferably selected so that all, or essentially all, of the test antigen molecules (e.g., $Stx17^{pSO2}$) are bound by the detection antibody. Thus, the detection antibody can be provided at concentrations at least an order of magnitude greater than the expected concentration of the test antigen. For example, if a test antigen has an expected concentration of 2 ng/ml, the detection antibody concentration can be at least 20 ng/ml (0.02 µg/ml). After a sufficient amount of time (from about 10 minutes to about 8 or more hours, which is determined in a calibration step), determined and optimized empirically as described herein. the plate is exposed to a magnetic field, the solution is then removed, and the sample is washed. The amount of label remaining in the well is then measured (e.g., by a luminometer).

The measured values can be quantitative or qualitative. Quantitative results are usually preferred. The measured values may then be compared to a standard or a threshold. One immunoassay system which may be used in the present invention is the Nichols Advantage® immunoassay system, which is a fully automated chemiluminescent system. The system is a bench-top instrument that performs solid phase chemiluminescent immunoassays. Streptavidin-coated magnetic particles and biotinylated antibodies may be employed in the assay system. Acridinium ester is typically the chemiluminescence label for signal detection. Other assay systems may also be employed in the present method, for example high throughput screening techniques, such as high throughput flow cytometry.

In practicing the methods of the invention, a control may be provided in the assay to ensure that the reactions have been successful. For example, a control could be provided with a polyclonal antibody solution for other analytes present in the biological sample or the same analytes present in other control samples. Other approaches are well known in the art.

Examples

Experimental Model and Subject Details
Cell Culture
HEK 293T and HeLa cells were obtained from ATCC and maintained in recommended media. Mouse bone marrow macrophages (BMMs) were extracted from mouse bone marrow and cultured in DMEM media supplemented with high glucose, sodium bicarbonate and 20% FBS in presence of mouse macrophage colony stimulating factor (mM-CSF). $LC3^{TKO}$, $GABARAP^{TKO}$, $Hexa^{KO}$ (all six $mATG8^{KO}$) and wild type control HeLa cells were from Michael Lazarou (Monash University, Melbourne). Cells were induced for autophagy by incubating in EBSS (Earle's Balanced Salt Solution).
Methods Details
Antibodies and Reagents
The following antibodies and dilutions were used: STX17 (rabbit; Sigma, HPA001204; 1:1000 (WB)); Flag (mouse; Sigma, F1804; 1:1,000 for (WB); 1:250 (IF)); GFP (rabbit; Abcam, ab290; 0.5 µg/ml (IP) and 1:1000 (WB)); LC3 (rabbit; MBL International PM036 1:500 (IF)); ATG13 (rabbit; Cell Signaling Technology, #13468, 1:1000 (WB); 1:150 (IF)); ATG13 (mouse; Millipore, MABC46, 1:200 (IF)); FIP200 (rabbit; Proteintech, 17250-I-AP; 1:200 (IF)); TBK1 (rabbit; Cell Signaling Technology, #3504; 1:1000 (WB, 1:200 (IP)); $TBK1^{PS172}$ (rabbit; Cell Signaling Technology, #5483, 1:1000 (WB)); FIP200 (rabbit; Cell Signaling Technology, #12436, 1:1000 (WB)); ULK1 (rabbit; Cell Signaling Technology, #6439, 1:750 (WB)); $STX17^{pSO2}$ (developed from rabbit BL31269, affinity purified over phospho-peptide. Prep: PP1) 1:250 (IF); 1:1000 (WB)); GFP-Trap (ChromoTek, Gtm-20). Goat anti-mouse IRDye 680 (LI-COR, 925-68020, 1:5000); Goat anti-Rabbit IRDye 800 (LI-COR, 926-32211, 1:5000); Trueblot anti-mouse DyLight 680, (Rockland. 18-4516-32, 1:2000); Trueblot anti-rabbit DyLight 800 (Rockland, 18-8816-31, 1:2000). Reagents: Lambda Protein Phosphatase (NEW ENGLAND BioLabs Inc.; P0753S); GM 130 (mouse BD Biosciences, RUO-610822, 1:500 (IF)); Dynabeads Protein G (Thermo Fisher Scientific 10003D 50 µl/IP); Bafilomycin A1 (InvivoGen, 13D02-MM); OptiPrep Density Gradient Medium (Sigma, D1556); Lipofictamine 2000, Thermo Scientific, 11668019; DMEM, RPMI and EBSS medias from Life Technologies. Gateway Vector Conversion System (ThermoFisher, 11828-029); LDH Assay kit (Promega, G1780).
Plasmids and Transfections
pDest-GFP-STX17 (Kumar et al., 2018),pDest-Myc-TBK1 and pDest-Myc-$TBK1^{K38D}$ (Pilli et al., 2012), pDest-mCherry-EGFP-LC3B (Pankiv et al., 2007), pEGFP-DFCP1 (Axe et al., 2008), pDest-EGFP-LC3B (Kirkin et al., 2009) have been described earlier. pMXs-IP-EGFP-hFIP200 was from Addgene (Addgene #38192), Keima-LC3 and LDH-Keima was from Heeseon An and J. Wade Harper (Harvard Medical School, Boston MA) (An and Harper, 2018), EGFP-WIPI2 was from T. Proikas-Cezanne (Eberhard Karls University Tubingen, Tübingen, Germany). GFP-ULK1 wad from N, Mizushima (The University of Tokyo, Tokyo, Japan). Plasmids and corresponding mutants used in this study, were cloned into pDONR221 using BP cloning, and expression vectors were made utilizing LR cloning (Gateway, ThermoFisher Scientific) in appropriate pDEST vectors for immunoprecipitation and other assays. Point-mutants were generated using the QuikChange Site-directed Mutagenesis Kit (Agilent, 200523). Plasmid constructs were verified by conventional restriction enzyme digestion and/or by DNA-sequencing. Plasmids were transfected using Pro-Fection Mammalian Transfection System from Promega or using Lipofectamine 2000 (Thermo Fisher Scientific).

Mass Spectrometry Analysis of STX17 Phosphorylation by TBK1

TBK1 knockout HEK293 cells were transfected with FLAG-STX17 and cotransfected with either empty Myc-tag vector, wild-type Myc-TBK1 or kinase-dead mutant Myc-TBK1 K38D. Cells were lysed and lysates were incubated with anti-FLAG M2 affinity agarose gel (Sigma-Aldrich, #A2220) for 2 hr and washed three times with Lysis buffer. Bound proteins were eluted by boiling in 2×SDS loading buffer for 10 mins. Eluted proteins were separated by SDS-PAGE. Gel pieces were subjected to in gel reduction with DTT, alkylation with iodoacetamide, and digestion using 6 ng/µl trypsin (Promega, #V511A) or chymotrypsin (Promega, #V1062)(Shevchenko et al., 1996). Peptide mixtures containing 0.1% formic acid were loaded onto a Thermo Fisher Scientific EASY-nLC1000 system and EASY-Spray column (C18, 2 µm, 100 Å, 50 µm, 50 cm). Peptides were fractionated using a 2-100% acetonitrile gradient in 0.1% formic acid over 50 min at a flow rate of 250 nl/min. The separated peptides were analysed using a Thermo Fisher Scientific Q-Exactive™ mass spectrometer. Data were collected in data dependent mode using a Top10 method. Processing of raw data was done using the Thermo Fisher Scientific Proteome Discoverer 2.2 software. The fragmentation spectra were searched against the current UniProt database using an in-house Mascot server (Matrix Sciences, UK). Peptide mass tolerances used in the search were 10 ppm, and fragment mass tolerance was 0.02 Da. Methionine oxidation and carbamidomethylation was set as variable modifications. Phosphorylation sites were verified using the PTMrs module in Proteome Discoverer™. Visualization of mass spectra was done with the Thermo Fisher Scientific Xcalibur™ software.

Mass Spectrometry Analysis of STX17 Interactors

HEK293T cells were transfected with plasmids (pDest-EGFP or pDest-EGFP-STX17) using Lipofectamine 2000 and immunoprecipitation was performed 48 h after transfection using ChromoTek GFP-Trap following the supplier's instructions. Immunoprecipitated (IPed) samples were loaded on a 12% SDS-polyacrylamide-gel and Coomassie stained. Subsequently each lane was cut into 5 slices and destained. Reduction, alkylation and proteinase digestion was carried out with trypsin overnight at 37° C. as previously described (Faeste et al., 2014; Faeste et al., 2016). Subsequent extraction of protease-generated peptides was performed as previously described (Anonsen et al., 2012). Analyses of in-gel digested peptides were done by reverse phase nanoflow liquid chromatography coupled to a nano-electrospray QExactive mass spectrometer utilizing a Higher energy induced dissociation (HCD) fragmentation (RP nLC-ESI MS2). The RP nLC was performed as previously described (Faeste et al., 2016).

Generation of CRISPR Mutant Cells

STX17 and ATG13 CRISPR in HeLa cells were generated as described (Kumar et al., 2018). Briefly, the lentiviral vector carrying both Cas9 enzyme and a gRNA targeting STX17 (GATAGTAATCCCAACAGACC, SEQ ID NO: 5), and ATG13 (TCACCCTAGTTATAGCAAGA, SEQ ID NO: 6) were transfected into HEK293T cells together with the packaging plasmids psPAX2 and pCMV-VSV-G at the ratio of 5:3:2. Two days after transfection, the supernatant containing lentiviruses was collected and used to infect the cells. 36 hours after infection, the cells were treated with puromycin (1 □g/ml for one week to select STX17-knockout cells. The knockouts were confirmed by western blotting. To generate TBK1 KO cells in HeLa and HEK293 cells, TBK1 gRNA (GATGAAGATCAACCTGGAAG, SEQ ID NO: 7) was annealed and ligated into a Bbs1 linearized PX459 vector (Addgene #62988) carrying both wild-type Cas9 and puromycin resistance genes. The gRNA containing vector was transfected into both cells using Metafectene Pro (Biontex #T020). 24 hours after transfection, cells were treated with 1 µg/ml of puromycin for 36 h to select transfected cells. Following selection, single cells were sorted into 96-well plates and expanded. The KO cells were confirmed by immunoblotting.

High Content Microscopy

Cells were plated in 96 well plates and were transfected with plasmids whenever required. Cells were stimulated for autophagy by incubating in EBSS for 1 h or 2 h followed by fixation with 4% paraformaldehyde for 10 mins. Cells were permeabilized with 0.1% saponin and blocked in 3% BSA for 20 mins followed by incubation with primary antibody for 4 h and secondary antibody for 1 h. High content microscopy with automated image acquisition and quantification was carried out using a Cellomics HCS scanner and iDEV software (Thermo Fisher Scientific) using a minimum of 500 cells per well. Scanning parameters and object mask were preset and predefined to analyze images. Hoechst 33342 staining was used for autofocusing and to define object/cells based on background staining of the cytoplasm. Regions of interest (ROI) or targets in primary objects (cells) were algorithm-defined to automatically identify puncta within valid primary objects. For transfected cells, after transfection with GFP or FLAG, cells were stained with required antibodies and HC analysis was used in a mode discriminating GFP or FLAG positive cells from non-transfected cells. A minimum of 500 transfected cells (valid primary objects determined by gating) per well were analyzed within the subpopulation of transfected cells (Mandell et al., 2014).

High Content Microscopy for Keima Probes

WT HeLa and STX17$^{KO}$ cells were plated in 96 well plates and transfected with Keima-expression plasmids as indicated in figures. Cells were incubated in full media or induced for autophagy by incubating with EBSS for the times indicated in figures. After autophagy induction cells were incubated with Hoechst 33342 for ten minutes and then images acquired for Keima fluorescence at 440 nm and 560 nm using the Cell Insight CX7 High-Content Screening (HCS) Platform (Thermo Fisher Scientific).

Super-Resolution Microscopy

Super-resolution imaging, and analysis were done as described previously (Kumar et al., 2018). HeLa cells were plated on 25 mm round coverslips (Warner instruments) and allowed to adhere overnight, followed by transfection with GFP-LC38 plasmid. Cells were induced for autophagy by incubating with EBSS for 2h. After fixation, cells were incubated with anti-rabbit-STX17$^{pS02}$ antibody for 4h and washed with PBS, followed by labeling with Alexa Fluor 647 (Invitrogen, A21245). The coverslip was mounted on an Attofluor cell chamber (A-7816, Life technologies) with 1.1 ml of the imaging buffer. The imaging and center-to-center distances between GFP-LC3B and STX17$^{pS02}$ cluster centroids per ROI (region of interest) were calculated as described earlier (Kumar et al., 2018).

Immunofluorescence Confocal Microscopy

For immunofluorescence confocal microscopy, cells were plated onto coverslips in 12-well plates. Cells were transfected with plasmids indicated in figures. Transfected cells were incubated in full media or EBSS for times indicated in figures and fixed in 4% paraformaldehyde for 10 min followed by permeabilization with 0.1% saponin in 3% BSA. Cells were then blocked in PBS containing 3% BSA and then incubated with primary antibodies for 4 h. Cells were washed three times with PBS and then incubated with appropriate secondary antibodies (Invitrogen) for 1 h at room temperature. Coverslips were then mounted using ProLong Gold Antifade Mountant (Invitrogen) and analyzed by confocal microscopy using the Zeiss LSMS10 Laser Scanning Microscope.

LDH (Lactate Dehydrogenase) Sequestration Assay

LDH sequestration assay was done as described previously (Pattingre et al., 2003); (Seglen et al., 2015). Briefly. $3\times10^6$ Hela$^{WT}$, STX17$^{KO}$ or ATG13$^{KO}$ cells were plated in 10 cm dishes, induced for autophagy using EBSS in presence of Bafilomycin A1 for 2 h. Cells were collected and washed twice with phosphate-buffered saline and then once with homogenization buffer (50 mM potassium phosphate, 1 mM EDTA, 1 mM dithiothreitol. 1 mM phenylmethylsulfonyl fluoride (PMSF), 300 mM sucrose, 100 µg/ml bovine serum albumin, and 0.01% Tween 20. Cells were homogenized in 1 ml of cold homogenization buffer by 15 strokes in a glass/Teflon homogenizer on ice, followed by centrifugation at 300×g for 10 min at 4° C. Post-nuclear material was layered on 3.5 ml of buffered Nycodenz/sucrose (10% sucrose, 8% Nycodenz, 1 mM EDTA, 100 µg/ml bovine serum albumin, and 0.01% Tween 20) and centrifuged at 7000×g for 1 h. The pellet was washed with homogenization buffer and resuspended in buffer containing 2 mM Tris-HCl (pH 7.4), 50 mM mannitol, 1 mM PMSF, 0.5 µg/ml leupeptin, 0.1 µg/ml aprotinin, and 0.7 □g/ml pepstatin. The suspension was sonicated and centrifuged at 15,000×g for 10 min. The lactate dehydrogenase activity was measured using an LDH assay kit from Promega using the manufacturer's protocols.

Membrane Fractionation

Membrane fractionation was carried out as described previously (Ge et al., 2013; Kumar et al., 2018). Briefly, HEK 293T cells (5 dishes per sample) were plated in 10 cm dishes, harvested, and homogenized by passing through a 22-G needle. Homogenates were subjected to sequential differential centrifugation at 3,000×g (10 min) and 25,000×g (20 min) to collect the pelleted membranes (TLA100.3 rotor, Beckman, polypropylene tubes; Beckman). 25K membrane pellets were suspended in 1 ml 19% OptiPrep for a step gradient containing 0.5 ml 22.5%, 1 ml 19% (sample), 0.9 ml 16%, 0.9 mi 12%, 1 ml 8%, 0.5 ml 5% and 0.2 ml 0% OptiPrep each. The OptiPrep gradient was centrifuged at 150,000×g for 3 h. Subsequently eight fractions, 0.5 ml each, were collected from the top. Fractions were diluted with B88 buffer (20 mM Hepes, pH 7.2, 150 mM potassium acetate, 5 mM magnesium acetate, 250 mM sorbitol) and membranes were collected by centrifugation at 100,000×g for 1 h. Sample were subjected to SDS-PAGE and western blot for STX17, STX17$^{pS02}$, GM130 and LC3 was done as described under immunoblotting.

Immunoblotting and Co-Immunoprecipitation Assays

Immunoblotting and co-immunoprecipitation (co-IP) were performed as described previously (Chauhan et al., 2016). Cells were lysed in NP40 buffer containing protease inhibitors cocktail (Roche, cat #11697498001) and PMSF (Sigma, cat #93482). Protein samples were boiled for 5 minutes at 100° C. followed by separation on SDS-PAGE and transfer onto PVDF membranes. The PVDF membranes were subjected to western blot analysis. Blots were developed using an ECL detection method. Alternatively, the membranes were labelled with fluorescent secondary antibody and analyzed with a LICOR-Odyssey apparatus using IMAGE STUDIO Lite software. For co-IP, cells were transfected with 10 µg of plasmids, wherever stated, and lysed as stated above. 10% input was saved, and remaining lysates were mixed with 2-5 µg antibody and incubated at 4° C. for 4 h followed by incubation with Dynabeads protein G (Life Technologies) for 2 h at 4° C. Beads were washed three times with PBS and then boiled with SDS-PAGE buffer for analysis of interacting protein by immunoblotting. Blots were quantified using Image J software.

Quantification and Statistical Analysis

MS raw files data were analyzed with Proteome Discoverer (v.1.4.7) utilizing the SEQUEST search engine and with MASCOT (version 2.4.0, Matrix Science, London, UK). Trypsin was selected as enzyme for samples treated with the respective enzymes allowing one missed cleavage site. Tolerance of 10 ppm for the precursor ion in the first search and 0.05 Da for the MS/MS fragments was applied. In addition to methionine oxidation, acetylation at protein N-terminus was allowed as variable modifications. Cysteine carbamidomethylation was set as fixed modification. High confidence peptides set at FDR<0.01 and medium confidence peptide set at FDR<0.05. Quantitative analyses using spectral counting were performed with Scaffold (version, 4.4.0, Proteome Software Inc., Portland, OR, USA). Peptide identifications were accepted at greater than 95.0% probability and protein identifications were accepted at greater than 99.0% probability. Only proteins with >1 peptide identification were considered for quantitation.

Data are expressed as means t SEM (n≥3). Data were analyzed with a paired two-tailed Student's t-test or analysis of variance (ANOVA) and multi-comparison analysis was performed with post hoc Tukey's test. Statistical significance was defined as *P<0.05, **p<0.01.

Results

Stx17 and TBK1 Interact and TBK1 Phosphorylates Stx17 at Ser-202

A set of proteomic analyses (FIG. 1A; Table S1) indicated that TBK1 was found in complexes with Stx17. Pull-down experiments comparing GFP vs GFP-Stx17 (Table S1, Tabs 1 and 2) showed 6 or 7 exclusive unique TBK1 peptides (FIG. 8A) present only with GFP-Stx17 in 2 out of 3 biological repeats (FIG. 1A). This was confirmed by co-immunoprecipitation (co-IP) of endogenous proteins (FIG. 1A, bottom panel) and FLAG-Stx17 co-IP with Myc-TBK1 (FIG. 1B). A band with lower electrophoretic mobility (a band shift) recognized by FLAG antibody appeared in FLAG-Stx17 co-IPs with enzymatically active Myc-TBK1 but not in co-IPs with enzymatically dead mutant Myc-TBK1$_{K38D}$ (FIG. 1B). Co-expression of FLAG-Stx17 with Myc-tagged proteins (Myc-TBK1 and Myc-TBK1$^{K38D}$ in TBK1$^{KO}$ HEK293 cells resulted in a similar FLAG-Stx17 mobility shift in cells expressing enzymatically active TBK1 but not in cells expressing TBK1$^{K38D}$) (FIG. 8B). A mass spectrometric (MS) analysis of FLAG-Stx17 immunoprecipitates from TBK1$^{KO}$ HEK293 cells identified a precursor ion at m/z 717.3318 corresponding to a triply charged trypsin generated Stx17 peptide IDSIADHVNSAAVN-VEEGTK (SEQ ID NO:8) with a phospho-Ser-202 (Stx17$^{pS02}$) modification (theoretical average at m/z 717.4096). Phosphorylation sites were verified using the PTMrs module in Proteome Discoverer. The MS/MS spectra from Proteome Discoverer indicated that it was Ser-202 that was phosphorylated and not the other potential sites (Table S1, Tab3). The phospho-IDSIADHVNSAAVNVEEGTK (SEQ ID NO:8)(Stx17$^{pSO2}$) peptide was 97-153 and 148-205 times (range from two experiments) more abundant in TBK1 samples relative to samples with Myc or Myc-TBK1$^{K38D}$ (FIG. 8C), indicating that TBK1 is a kinase acting on Ser-202 of Stx17. There were additional phosphorylated residues, but they either did not depend on TBK1 or had low post-translational modification probability or low peptide identification confidence.

The Ser-202 residue is within an evolutionarily highly conserved sequence in Stx17 from fish to humans (FIG. 8D), located between the SNARE layers +1 and +2 ("1.5") and predicted to face outwards of the 4-helix bundle (FIG. 8E). We raised an antibody against a pSer-202 phosphopeptide spanning this region of Stx17 and obtained antibodies recognizing a band on Western blots that was absent in Stx17 CRISPR knockout HeLa cells (FIGS. 1D and 8F), and strongly diminished in TBK1$^{KO}$ HeLa cells (FIGS. 1D, 8G and 8I). The Stx17$^{pSO2}$ band was responsive to agonists of TBK1 (muramyl-dipeptide/MDP and LPS), albeit it was also detectable in resting cells (FIG. 8H). A TBK1 inhibitor BX795 inhibited Stx17 phosphorylation (Stx17$^{pSO2}$) in cells stimulated with LPS, and also reduced the low baseline levels seen in unstimulated cells (FIG. 8I). Thus, TBK1 phosphorylates Stx17 at Ser202 (FIG. 1E).

Phosphorylated Stx17 Localizes to the Golgi

Using the antibody against Stx17$^{pSO2}$ we found that it labeled specifically Stx17 at the Golgi apparatus. FIG. 2A shows that Stx17$^{pSO2}$ colocalizes in resting cells with the Golgi marker GM130. Antibody labeling of Stx17$^{pSO2}$ was not detected in Stx17$^{KO}$ cells (FIG. 2A) and the signal was absent in cells pretreated with λ phosphatase (FIG. 9A). In TB1K$^{KO}$ cells, there was still some labeling, but the signal was dramatically reduced (FIG. 9A). We could not compare Stx17$^{pSO2}$ with the distribution of total endogenous Stx17 by immunofluorescence since there are at present no commercial antibodies that can reveal authentic endogenous Stx17, but it is in general known to be in various membranes including ER (Steegmaier et al., 2000; Steegmaier et al., 1998), mitochondria (Arasaki et al., 2015; Hamasaki et al., 2013; Itakura et al., 2012) ER-mitochondria contact sites (Hamasaki et al., 2013), and, when Stx17's putative C-terminal ER retrieval signal sequence (Popoff et al., 2011), KKCS, is deleted, in the Golgi (Itakura et al., 2012). A question arose whether Stx17 changes, i.e. its knockout, can affect other SNAREs implicated in autophagy. We tested but did not detect changes in levels of SNAREs, VAMP7 (Moreau et al., 2011) and SNAP29 (Itakura et al., 2012) (FIGS. 9B,C), albeit as expected SNAP29 and VAMP8 complexes were reduced in Stx17$^{KO}$ cells (FIG. 9D), in keeping with prior reports in the context of autophagosomal maturation (Diao et al., 2015; Itakura et al., 2012). Thus, changes in other SNAREs or their complexes, are unlikely to explain the Golgi localization of Stx17$^{pSO2}$. Further confirmation that Stx17$^{pSO2}$ localized to the Golgi was established by subcellular membrane fractionation (FIG. 2B). Thus, the data shown here indicate that Stx17$^{pSO2}$ specifically localizes to the Golgi apparatus.

Upon starvation, which is a classical inducer of autophagy, Stx17$^{pSO2}$ partially translocated from the Golgi to peripheral puncta and lost its tight Golgi-ribbon like morphology otherwise observed in resting cells (FIGS. 2C, 9E). When this was quantified by high content microscopy (HC), a significant reduction in colocalization between Stx17$^{pSO2}$ and GM130 was observed (FIG. 2D,E), whereas the total number of peripheral Stx17$^{pSO2}$ increased (FIG. 2F,G). The total level of Stx17$^{pSO2}$ did not change with starvation (FIG. 9F). Thus, starvation-induced autophagy (FIGS. 9G,H) is not associated with changes in Stx17$^{pSO2}$ levels but is associated with redistribution of Stx17$^{pSO2}$ from the Golgi apparatus to peripheral punctate sites (FIG. 2H).

Stx17 and TBK1 Affect Mammalian PAS Formation

The intriguing phenotype of Stx17$^{pSO2}$ translocation to peripheral puncta during induction of autophagy prompted us to test whether the mPAS formation was affected in Stx17 and TBK1 knockouts. Using ATG13, a component of the mammalian ULK1-ATG13-FIP200 complex often used as an early surrogate marker for mPAS (Ganley et al., 2009; Jung et al., 2009; Karanasios et al., 2013; Karanasios et al., 2016; Koyama-Honda et al., 2013; Lamb et al., 2013), we observed that endogenous ATG13 puncta formation in response to starvation is severely reduced in Stx17$^{KO}$ and cells (FIGS. 3A-C and 10A). Along with ATG13, another component of the ULK1 autophagosomal initiation complex is FIP200/RB1CC1 (Ganley et al., 2009; Jung et al., 2009). Endogenous FIP200 puncta were also severely reduced in Stx17$^{KO}$ and TBK1$^{KO}$ cells (FIGS. 3D-F and 10B). The ULK1 puncta (GFP-ULK1) were correspondingly reduced in Stx17$^{KO}$ cells (FIGS. 10C-E). DFCP1 (Axe et al., 2008) profiles were reduced in Stx17$^{KO}$ and TBK1$^{KO}$ cells (Figures 10F-H). Another well-known marker of early stages of autophagy, WIPI2, displayed reduced number of puncta in Stx17 knockout cells (FIG. 10 I-K). Thus, Stx17 and TBK1 are required for formation of mPAS and early autophagosomal intermediate structures.

Only Phosphorylatable or Phosphomimetic Stx17 can Complement ATG13 and FIP200 Phenotypes in Stx17$^{KO}$ Cells We next asked the question of whether Stx17$^{KO}$ can be complemented to restore ATG13 and FIP200 responses to autophagy induction by starvation. We generated phosphomimetic and unphosphorylatable mutants of Stx17, Stx17$^{S202D}$ and Stx17$^{S202A}$ and used FLAG-Stx17 WT, S202A, and S202D variants in subsequent experiments. Only Stx17$^{WT}$ and Stx17$^{S202D}$ complemented Stx17$^{KO}$ in HeLa cells, as quantified by HC analysis of cells gated for transfected cells and judged by both markers, ATG13 and FIP200 puncta, in starved cells (FIGS. 4A-D and 11A), these data were further confirmed by confocal microscopy, where Stx17$^{KO}$ cells complemented with Stx17$^{WT}$ and Stx17$^{S202D}$ restored ATG13 and FIP200 response to autophagy (FIGS. 11B,C). Furthermore, we cross-complemented TBK1 knockout cells with FLAG-Stx17$^{WT}$, FLAG-Stx17$^{S202A}$, and FLAG-Stx17$^{202D}$ variants, HC microscopy quantification revealed that Stx17$^{S202D}$ fully complemented the reduced ATG13 and FIP200 puncta formation in TBK1$^{KO}$ cells whereas Stx17$^{S202A}$ had no effect. Nevertheless, FLAG-Stx17$^{WT}$ showed lower in magnitude but measurable cross-complementation in TBK1$^{KO}$, likely due to another kinase (FIG. 4E-H). Thus, preventing Stx17 from being phosphorylated at the S202 site precludes its functionality in autophagy initiation. Stx17 and its phosphorylation by TBK1 affect autophagy initiation as summarized in FIG. 4I.

Phosphorylated Stx17 Interacts with ATG13 and FIP200

We next tested whether Stx17$^{pSO2}$ associated with members of the mPAS complex. Stx17$^{pSO2}$ co-IP'ed with endogenous ATG13 (Figure A). It also interacted with FIP200 (FIG. 5B). We therefore used phosphomimetic and unphosphorylatable mutants of Stx17, Stx17$^{S202D}$ and Stx17$^{S202A}$, to test their capacity in these interactions. Only Stx17$^{S202D}$ and wild type Stx17 were found in co-IPs with ATG13 (with Stx17$^{S202D}$ showing enhanced binding; FIGS. 5C,D), and with FIP200 (FIGS. 5E,F). We tested whether Stx17$^{pS02}$, which translocates from the Golgi to peripheral sites/puncta (FIG. 2B), colocalized with ATG13 upon induction of autophagy. For this, antibodies were not compatible for testing in HeLa cells and thus we resorted to mouse cells, using primary macrophages (bone marrow-derived macrophages; BMMs). In BMMs, Stx17$^{pS02}$ colocalized with ATG13 puncta and this colocalization increased upon induction of autophagy (FIGS. 5G-I, FIG. 11D). Stx17$^{pS02}$ also colocalized with GFP-FIP200 and GFP-ULK1 (FIGS. 5J-O and 11E,F). GFP-FIP200 and Stx17$^{pS02}$ colocalized in resting cells and the colocalization appeared to be in the Golgi, where pools of Stx17$^{pS02}$ reside. Subcellular membrane separation showed co-fractionation of FIP200 and Stx17$^{pS02}$ with the Golgi marker GM130 (FIG. 11G). Thus, not only does Stx17 affect mPAS components but it also interacts and colocalizes with them (FIG. 5P).

Translocation of Stx17 to DFCP1 and LC3 Profiles in Cells Induced for Autophagy

We next asked the question whether in cells induced for autophagy, Six17$^{pS02}$ eventually transfers to nascent autophagosomes. Formation of DFCP1$^+$ omegasome heralds formation of autophagosomes (Axe et al., 2008). We found that Stx17$^{pS02}$ colocalized with DFCP1 (FIGS. 11H,I), which was tested at a time point later than ATG13 colocalization, compatible with the expectation that ATG13-FIP200 mPAS precedes autophagosome formation. Similarly, Stx17$^{pS02}$ colocalized with LC3 (using GFP-LCB; FIGS. 6A,B). Super-resolution microscopy showed that Stx17$^{pS02}$ colocalizes with LC3 at a distance of 40 nm (FIGS. 6C,D and 12A), which places them very near each other on the autophagosomes, compatible with our prior report of direct binding between Stx17 and mAtg8s (Kumar et al., 2018). HC analyses further confirmed increased colocalization between Stx17$^{pS02}$ and LC3B (FIGS. 6E,F). Mutant forms of Stx17 showed differences in colocalization with LC3B, as quantified by HC: WT and the phosphomimetic Stx17$^{S202D}$ mutant colocalized with LC3B more so than the non-phosphorylatable Stx17$^{S202A}$ mutant (FIGS. 6G, 12B), reflected also in confocal analyses and Pearson's colocalization coefficients (FIGS. 12C,D). Stx17$^{S202A}$ showed dispersed cytoplasmic punctate structures (FIG. 12C, middle panels) mostly negative for LC3 (FIG. 12D), whereas, Stx17$^{S202D}$ showed a Golgi-like localization (FIG. 12C, bottom panels; typical of Stx17$^{pS02}$) along with peripheral puncta which were positive for LC3 (FIGS. 12C,D). Furthermore, in cells knocked out for TBK1, there was reduced association of Stx17 and GFP-LC3B in co-IP experiments (FIGS. 12E,F). Consistent with this, HC analyses showed reduced colocalization between FLAG-Stx17 and LC3 in TBK1$^{KO}$ cells (FIGS. 12G,H). Thus, phosphorylation of Stx17 is important for its colocalization and association with LC3.

Finally, we tested by subcellular fractionation and density separation on OptiPrep gradients where Stx17$^{pS02}$ co-fractionates before and after induction of autophagy. We found that most of Stx17$^{pS02}$ in resting (full medium) cells co-fractionates with the Golgi marker GM130 (FIG. 6H), compatible with our immunofluorescence findings. In contrast, the spread of total Stx17 in gradients was much wider and it was dis-enriched in the Golgi fractions (FIG. 6H). Following induction of autophagy by starvation in EBSS, some of Stx17$^{pS02}$ translocated to a subset of LC3-II° (autophagosomal) fractions (FIG. 6I). Thus, as determined by various methods. Stx17$^{pS02}$ eventually ends in autophagosomal compartments (FIG. 6I).

Stx17 and TBK1 are Required for Efficient Assembly of ULK1-ATG13-FIP200 Complexes and LC3 Puncta Formation We next wondered whether Stx17 affected the formation of ULK1 complexes. Hela cells knocked out for Stx17 showed less ULK1 in protein complexes with ATG13 when compared to wild type cells (FIG. 7A,B). Likewise, HeLa Stx17$^{KO}$ cells showed less FIP200 in complexes with ATC13 (FIG. 7C,D). Similarly, TBK1$^{KO}$ HeLa cells displayed reduced ULK1 (FIG. 7E,F) and FIP200 (FIG. 7G,H) levels in protein complexes with ATG13. Thus, Stx17 and its phosphorylation by TBK1 are necessary for efficient assembly of components of the mPAS. Further, knockouts of Stx17 and TBK1 reduced LC3 puncta formation at 30 min and 1 h post-induction by starvation. This was tested by monitoring endogenous LC3 response (FIGS. 7I and 13A). We also used fusion of LC3 with fluorescent proteins to monitor autophagy induction. The GFP-LC3 reporter showed no response in Stx17$^{KO}$ cells, and yet parental wild type cells showed a time response (FIGS. 7J,K and FIG. 13B-D). Using Keima-LC3 (An and Harper, 2018; Katayama et al., 2011), we also observed fewer fluorescent puncta detected by excitation at 440 nm in Stx17$^{KO}$ cells relative to wild type cells (FIG. 7L,M). Thus, Stx17 matters for autophagy initiation.

Stx17 is Required for Efficient Bulk Autophagy Cargo Sequestration

If Stx17 is important for autophagosomal initiation, and not only for autophagosome-lysosome fusion as previously reported (Itakura et al., 2012), one prediction is that Stx17$^{KO}$ cells would display less bulk autophagy cargo sequestration. A classical cargo for this is uptake of cytosolic lactate dehydrogenase (LDH) into autophagosomes, that can be tested in a well-established cargo sequestration assay (Kopitz et al., 1990; Pattingre et al., 2003; Seglen and Gordon, 1984; Seglen et al., 2015). Employing this assay, we found that Stx17$^{KO}$ reduced LDH sequestration in autophagosomes comparably to the reduction in cargo sequestration caused by a knockout in ATG13 (FIG. 13E), or upon treatment of WT cells with classical inhibitor of autophagy 3MA (FIG. 7N,O). Published knockouts (Nguyen et al., 2016) of mAtg8s in combinations as triple LC3A-C combination, or triple GABARAPs (GABARAP, L1 and L2), or all six mAtg8s (Hexa) also reduced LDH sequestration (FIGS. 7P and 13F), albeit the effect of LC3 triple knockouts was milder than effects of GABARAP triple knockouts and Hexa knockout cells, in keeping with a prior report (Engedal and Seglen, 2016; Szalai et al., 2015). In all the above experiments the cells were inhibited for autophagosomal maturation using bafilomycin A1. We also employed LDH-mKeima construct (An and Harper, 2018) and observed reduced Keima fluorescence at 440 nm (excitation) in Stx17$^{KO}$ cells (FIGS. 7Q,R). Thus, Stx17 is necessary for autophagy initiation and for the sequestration of nonselective, bulk autophagy cargo into non-degradative early autophagosomal organelles (FIG. 7S).

Discussion

Pursuant to the present invention, we found that Stx17 is a substrate for TBK1 phosphorylation and that both TBK1 and Stx17 play a role in autophagy initiation. The phosphorylated form of Stx17 is localized to the Golgi in resting cells. During induction of autophagy, these pools of Stx17 redistribute from the Golgi to peripheral vesicles, which are the likely sites contributing to pre-autophagosomal structures, i.e. the FIP200 and ATG13 puncta, the early precursors of autophagosomes in mammalian cells (Alers et al., 2014; Karanasios et al., 2013; Karanasios et al., 2016; Mizushima et al., 2011; Nishimura et al., 2017). Phosphorylation of Stx17 is necessary for efficient formation of the ATG13 and FIP200 puncta in response to starvation, and Stx17 is required for robust interactions between components of the FIP200-ATG3-ULK1 complex, Stx17 knockout cells do not respond to autophagy induction, reflected in diminished LC3 puncta formation and reduced sequestration of LDH, a classical substrate for starvation-induced bulk autophagy (Kopitz et al., 1990; Pattingre et al., 2003; Seglen and Gordon, 1984; Seglen et al., 2015). Thus, TBK1 and Stx17 cooperate in autophagy initiation during starvation responses.

TBK1, a kinase often associated with immune responses such as type I interferon induction and with roles in cancer and neurodegeneration (Ahmad et al., 2016), has been implicated in autophagy in several ways including interactions with or phosphorylation of autophagy receptors such as NDP52 (Thurston et al., 2009). Optineurin (Wild et al, 2011) and p62 (Pilli et al., 2012). Our present study shows that TBK1 has additional substrates implicated in autophagy, such as Stx17. Previously, both TBK1 (Pilli et al., 2012) and Stxl7 (Itakura et al., 2012) have been shown to play a role in autophagy maturation. Our new findings do not contradict this role but indicate that TBK1 plays a role at multiple stages of autophagy, as already evident from modifications of selective autophagy receptors by TBK1 (Wild et al., 2011).

Stx17 has been well studied in the context of autophagy maturation (Diao et al., 2015; Guo et al., 2014; Itakura et al., 2012; Takats et al., 2013; Wang et al., 2016), although more recent studies have implicated additional SNAREs, such as Ykt6. in autophagosome-lysosome fusion (Bas et al, 2018; Gao et al., 2018: Matsui et al., 2018: Takats et al., 2018). Furthermore, Stx17 has diverse functions, some of which am compatible with autophagy initiation (Arasaki et al., 2018; Hamasaki et al., 2013). These additional roles include various processes such as mitochondrial fission (Arasaki et al., 2015), fusion with lysosomes of specialized mitochondria-derived vesicles (McLelland et al., 2016), and fusion of ER-derived vesicles with lysosomes (Fregno et al., 2018), the latter being compatible with the early description of Stx17 localization to the ER (Steegmaier et al., 2000).

Our findings place $Stx17^{pS02}$ at the Golgi. It has previously been shown that mutation of the putative ER-retrieval signal at the C-terminus of Stx17 leads to re-localization of the bulk Stx17 to the Golgi (Itakura et al., 2012). It is possible that the phosphorylated form of Stx17 conformationally escapes recognition by COPI-dependent ER-retrieval machinery (Popoff et al., 2011). Our MS analyses (Table S1), indicate extensive interactions of Stxl7 with the components of the COP complex (COPA, COPB2, COPG2 and COPG1), in keeping with the above trafficking routes of Stx17.

Upon autophagy induction, $Stx17^{pS02}$ translocates from the Golgi to the peripheral pools where it colocalizes with FIP200, ATG13, and ULK1. Of interest is that FIP200, like $Stx17^{pS02}$, co-fractionates with the Golgi membranes. It is possible that a fraction of FIP200 destined for mPAS translocates via a route related to that of $Stx17^{pS02}$. The Golgi apparatus appears to serve as a depot of Stx17 and possibly of FIP200 until they are needed at the sites of autophagosome formation. This is similar to the presence of ATG9 in the Golgi (Saitoh et al., 2009: Young et al., 2006) until it is mobilized into peripheral Atg9 vesicular pools (Lamb et al., 2016; Soreng et al., 2018). Of note, TBK1 responds to various inputs, in combinations with different receptors/adaptors that it interacts with (Liu et al., 2015), and thus Stx17 could play a role of a novel adaptor/effector for TBK1. One of the previously defined pathways with well-studied adaptors (Liu et al., 2015), includes STING, which traffics from the ER to the Golgi and then to post-Golgi compartments (Saitoh et al., 2009). It is likely that Stx17 and TBK1 intersect at some point along such routes. Of note, the response to starvation is not linked to phosphorylation of Stx17 by TBK1, which appears tonic in nature and is prominently present in resting cells. Rather, starvation induces trafficking events relocating phosphorylated Stx17 from the Golgi to mPAS. The mechanism of this is unknown at present but may share the Atg9 route or depend on another membrane trafficking pathway.

We previously reported that Stx17 interacts with LC3 (Kumar et al., 2018), further extended hem to the phosphorylated form of Stx17, $Stx17^{pS02}$. Since TBK1 knockout reduced this interaction, it is likely that phosphorylation by TBK1 of Stx17, affects the ability of Stx17 to associate with early autophagosomal structures, possibly contributing to transitions between mPAS and LC3-positive autophagosomes. In support of this view is the finding that $Stx17^{pS02}$ also colocalizes with DFCP1, a marker for an intermediate omegasome structure from which nascent autophagosomes emerge (Axe et al., 2008). Thus, Stx17 transits sequential sites along the autophagosomal pathway.

The interconnections between different parts of autophagy initiation machinery have several well-known precedents, expanded through studies presented here whereby Stx17 and TBK1 integrate additional components with previously appreciated ones. For example, FIP200 links the ULK1 complexes (Hara et al, 2008) with ATG161 (Fujita et al., 2013; Gammoh et al., 2013), and hence connects the LC3 conjugation machinery with the mPAS. Furthermore, WIPI2, a PI3P-binding factor, directly interacts with ATG16L1 (Dooley et al., 2014). TBK1 binds, phosphorylates and modulates autophagy receptors such as p62 (Pilli et al., 2012). Optineurin (Wild et al., 2011), and NDP52 (Thurston et al., 2009), and, as shown here, phosphorylates Stx17 and modulates its role in mPAS assembly, thus linking selective autophagy with the core mPAS machinery. Stx17 provides multiple links to the PI3K complex as well: Six17 binds ATG14 (Arasaki et al., 2018; Diao et al., 2015), a component of the PI3K complex engaged in autophagy initiation. Stx17 and TBK1 role in the assembly of FIP200-ATG13-ULK1 mPAS complexes, most likely including the constitutive partner of ATG13, ATG101 (Suzuki et al., 2015)(albeit this was not specifically verified here) may affect ATG13 interactions with ATG14 and the PI3K complex (Park et al., 2016). Our previous report that Stx17 can bind unlipidated LC3/mAtg8s (Kumar et al., 2018) suggests the possibility that Stx17 may present LC3/mAtg8s as substrates to the conjugation/lipidation machinery. However, other roles for LC3 binding to the Stx17 SNARE domain are possible, such as temporarily blocking Stx17's engagement in a premature SNARE bundle assembly until the later stages, i.e. maturation. The incorporation of Stx17 at the outset, within the autophagy complexes governing the earliest stages of autophagosome formation. coordinates initiation with subsequent autophagy stages culminating in fusion with the lysosome. This ensures that once the cargo sequestration process is initiated it can be completed to accomplish its degradative role.

REFERENCES

Ahmad, L, Zhang, S. Y., Casanova, J. L., and Sancho-Shimizu, V. (2016). Human TBK1: A Gatekeeper of Neuroinflammation. Trends Mol Med 22, 511-527.

Alers, S., Wesselborg, S., and Stork, B. (2014). ATG13: just a companion, or an executor of the autophagic program? Autophagy 10, 944-956.

An, H., and Harper, J. W. (2018). Systematic analysis of ribophagy in human cells reveals bystander flux during selective autophagy. Nat Cell Biol 20, 135-143.

Arasaki, K., Nagashima, H., Kurosawa, Y., Kimura, H., Nishida, N., Dohmae, N., Yamamoto, A., Yanagi, S., Wakana, Y., Inoue, H., el al. (2018). MAP1B-LC1 prevents autophagosome formation by linking syntaxin 17 to microtubules. EMBO Rep.

Arasaki, K., Shimizu, H., Mogari, H., Nishida, N., Hirota, N., Furuno, A., Kudo, Y., Baba, M., Baba, N., Cheng, J., et al. (2015). A role for the ancient SNARE syntaxin 17 in regulating mitochondrial division. Dev Cell 32, 304-317.

Axe, E. L., Walker, S. A., Manifava, M., Chandra, P., Roderick, H. L., Habermann, A., Griffiths, G., and Ktistakis, N. T. (2008). Autophagosome formation from membrane compartments enriched in phosphatidylinositol 3-phosphate and dynamically connected to the endoplasmic reticulum. J Cell Biol 182, 685-701.

Bas, L., Papinski, D., Licheva, M., Torggler, R., Rohringer, S., Schuschnig, M., and Kraft, C. (2018). Reconstitution reveals Ykt6 as the autophagosomal SNARE in autophagosome-vacuole fusion. J Cell Biol.

Baskaran, S., Carlson, L. A., Stjepanovic, G., Young, L. N., Kim do, J., Grob, P., Stanley, R. E., Nogales, E., and Hurley, J. H. (2014). Architecture and dynamics of the autophagic phosphatidylinositol 3-kinase complex. Elife 3.

Chan, E. Y., Kir, S., and Tooze, S. A. (2007). siRNA screening of the kinome identifies ULK1 as a multidomain modulator of autophagy. J Biol Chem 282, 25464-25474.

Diao, J., Liu, R., Rong, Y., Zhao, M., Zhang, J., Lai, Y., Zhou, Q., Wilz, L. M., Li, J., Vivona, S., et al. (2015). ATG14 promotes membrane tethering and fusion of autophagosomes to endolysosomes. Nature 520, 563-566.

Dooley, H. C., Razi, M., Polson, H. E., Girardin, S. E., Wilson, M. I., and Tooze, S. A. (2014). WIPI2 Links LC3 Conjugation with PI3P, Autophagosome Formation, and Pathogen Clearance by Recruiting Atg12-5-16L1. Mol Cell 55, 238-252.

Engedal, N., and Seglen, P. O. (2016). Autophagy of cytoplasmic bulk cargo does not require LC3. Autophagy 12, 439-441.

Fregno, I., Fasana, E., Bergmann, T. J., Raimondi, A., Loi, M., Solda, T., Galli, C., D'Antuono, R., Morone, D., Danieli, A., et al. (2018). ER-to-lysosome-associated degradation of proteasome-resistant ATZ polymers occurs via receptor-mediated vesicular transport. EMBO J 37.

Fujita, N., Morita, E., Itoh, T., Tanaka, A., Nakaoka, M., Osada, Y., Umemoto, T., Saitoh, T., Nakatogawa, H., Kobayashi, S., et al. (2013). Recruitment of the autophagic machinery to endosomes during infection is mediated by ubiquitin. J Cell Biol 203, 115-128.

Gammoh, N., Florey, O., Overholizer, M., and Jiang, X. (2013). Interaction between FIP200 and ATG16L1 distinguishes ULK1 complex-dependent and -independent autophagy. Nat Struct Mol Biol 20, 144-149.

Ganley, I. G., Lam du, H., Wang, J., Ding, X., Chen, S., and Jiang, X. (2009). ULK1.ATG13.FIP200 complex mediates mTOR signaling and is essential for autophagy. J Biol Chem 284, 12297-12305.

Gao, J., Reggiori, F., and Ungermann, C. (2018). A novel in vitro assay reveals SNARE topology and the role of Ykt6 in autophagosome fusion with vacuoles. J Cell Biol.

Guo, B., Liang, Q., Li, L, Hu, Z., Wu, P., Zhang, P., Ma, Y., Zhao, B., Kovacs, A. L., Zhang, Z., et al. (2014). O-GcNAc-modification of SNAP-29 regulates autophagosome maturation. Nat Cell Biol 16, 1215-1226.

Hamasaki, M., Furuta, N., Matsuda, A., Nezu, A., Yamamoto, A., Fujita, N., Oomori, H., Noda, T., Haraguchi, T., Hiraoka, Y., et al. (2013). Autophagosomes form atER-mitochondria contact sites. Nature 495, 389-393.

Hara, T., Takamura, A., Kishi, C., Iemura, S., Natsume, T., Guan, J. L., and Mizushima, N. (2008). FIP200, a ULK-interacting protein, is required for autophagosome formation in mammalian cells. J Cell Biol 181, 497-510.

Inoki, K., Kim, J., and Guan, K. L, (2012). AMPK and mTOR in cellular energy homeostasis and drug targets. Annu Rev Pharmacol Toxicol 52, 381-400. Itakura, E., Kishi-Itakura, C., and Mizushima, N. (2012). The hairpin-type tail-anchored SNARE syntaxin 17 targets to autophagosomes for fusion with endosomes/lysosomes. Cell 151, 1256-1269.

Jung, C. H., Jun, C. B., Ro, S. H., Kim, Y. M., Otto, N. M., Cao, J., Kundu, M., and Kim, D. H. (2009). ULK-Atg13-FIP200 complexes mediate mTOR signaling to the autophagy machinery. Mol Biol Cell 20, 1992-2003.

Kabeya, Y., Mizushima, N., Ueno, T., Yamamoto, A., Kirisako, T., Noda, T., Kominami, E., Ohsumi, Y., and Yoshimori, T. (2000). LC3, a mammalian homologue of yeast Apg8p, is localized in autophagosome membranes after processing. Embo J 19, 5720-5728.

Karanasios, E., Stapleton, E., Manifava, M., Kaizuka, T., Mizushima, N., Walker, S. A., and Ktistakis, N. T. (2013). Dynamic association of the ULK1 complex with omegasomes during autophagy induction. J Cell Sci 126, 5224-5238.

Karanasios, E., Walker, S. A., Okkenhaug, H., Manifava, M., Hummel, E., Zimmermann, H., Ahmed, Q., Domart, M. C., Collinson, L., and Ktistakis, N. T. (2016). Autophagy initiation by ULK complex assembly on ER tubulovesicular regions marked by ATG9 vesicles. Nature communications 7, 12420.

Katayama, H., Kogure, T., Mizushima, N., Yoshimori, T., and Miyawaki, A. (2011). A sensitive and quantitative technique for detecting autophagic events based on lysosomal delivery. Chem Biol 18, 1042-1052.

Kopitz, J., Kisen, G. O., Gordon, P. B., Bohley, P., and Seglen, P. O. (1990). Nonselective autophagy of cytosolic enzymes by isolated rat hepatocytes. J Cell Biol 111, 941-953.

Koyama-Honda, I., Itakura, E., Fujiwara, T. K., and Mizushima, N. (2013). Temporal analysis of recruitment of mammalian ATG proteins to the autophagosome formation site. Autophagy 9, 1491-1499.

Kumar, S., Jain, A., Farzam, F., Jia, J., Gu, Y., Choi, S. W., Mudd, M. H., Claude-Taupin, A., Wester, M. J., Lidke, K. A., et al. (2018). Mechanism of Stx17 recruitment to autophagosomes via IRGM and mammalian Atg8 proteins. J Cell Biol 217, 997-1013.

Lamb, C. A., Nuhlen, S., Judith, D., Frith, D., Snijders, A. P., Behrends, C., and Tooze, S. A. (2016). TBC1D14 regulates autophagy via the TRAPP complex and ATG9 traffic. EMBO J 35, 281-301.

Lamb, C. A., Yoshimori, T., and Tooze, S. A. (2013). The autophagosome: origins unknown, biogenesis complex. Nat Rev Mol Cell Biol 14, 759-774.

Liu, S., Cai, X., Wu, J., Cong, Q., Chen, X., Li, T., Du, F., Ren, J., Wu, Y. T., Grishin, N. V., et al. (2015). Phosphorylation of innate immune adaptor proteins MAVS, STING, and TRIF induces IRF3 activation. Science 347, aaa2630.

Matsui, T., Jiang, P., Nakano, S., Sakamaki, Y., Yamamoto, H., and Mizushima, N. (2018). Autophagosomal YKT6 is required for fusion with lysosomes independently of syntaxin 17. J Cell Biol 217, 2633-2645.

McLelland, G. L., Lee, S. A., McBride, H. M., and Fon, E. A. (2016). Syntaxin-17 delivers PINK1/parkin-dependent mitochondrial vesicles to the endolysosomal system. J Cell Biol 214, 275-291.

Mizushima, N., Yoshimori, T., and Ohsumi, Y. (2011). The role of Atg proteins in autophagosome formation. Annu Rev Cell Dev Biol 27, 107-132.

Moreau, K., Ravikumar, B., Renna, M., Puri, C., and Rubinsztein, D. C. (2011). Autophagosome precursor maturation requires homotypic fusion. Cell 146, 303-317.

Nguyen, T. N., Padman, B. S., Usher, J., Oorschot, V., Ramm, G., and Lazarou, M. (2016). Atg8 family LC3/GABARAP proteins are crucial for autophagosome-lysosome fusion but not autophagosome formation during PINK1/Parkin mitophagy and starvation. J Cell Biol 215, 857-874.

Nishimura, T., Tamura, N., Kono, N., Shimanaka, Y., Arai, H., Yamamoto, H., and Mizushima, N. (2017). Autophagosome formation is initiated at phosphatidylinositol synthase-enriched ER subdomains. EMBO J 36, 1719-1735.

Park, J. M., Jung, C. H., Seo, M., Otto, N. M., Grunwald, D., Kim, K. H., Moriarity, B., Kim, Y. M., Starker, C., Nho, R. S., et al. (2016). The ULK1 complex mediates MTORC1 signaling to the autophagy initiation machinery via binding and phosphorylating ATG14. Autophagy 12, 547-564.

Pattingre, S., Bauvy, C., and Codogno, P. (2003). Amino acids interfere with the ERK1/2-dependent control of macroautophagy by controlling the activation of Raf-1 in human colon cancer HT-29 cells. J Biol Chem 278, 16667-16674.

Petiot, A., Ogier-Denis, E., Blommaart, E. F., Meijer, A. J., and Codogno, P. (2000). Distinct classes of phosphatidylinositol Y-kinases are involved in signaling pathways that control macroautophagy in HT-29 cells. J Biol Chem 275, 992-998.

Pilli, M., Arko-Mensah, J., Ponpuak, M., Roberts, E., Master, S., Mandell, M. A., Dupont, N., Ornatowski, W., Jiang, S., Bradfute, S. B., et al. (2012). TBK-1 Promotes Autophagy-Mediated Antimicrobial Defense by Controlling Autophagosome Maturation. Immunity 37, 223-234.

Popoff, V., Adolf, F., Brugger, B., and Wieland, F. (2011). COPI budding within the Golgi stack. Cold Spring Harb Perspect Biol 3, a005231.

Saitoh, T., Fujita, N., Hayashi, T., Takahara, K., Satoh, T., Lee, H., Matsunaga, K., Kageyama, S., Omori, H., Noda, T., et al. (2009). Atg9a controls dsDNA-driven dynamic translocation of STING and the innate immune response. Proc Natl Acad Sci USA 106, 20842-20846.

Seglen, P. O., and Gordon, P. B. (1984). Amino acid control of autophagic sequestration and protein degradation in isolated rat hepatocytes. J Cell Biol 99, 435-444.

Seglen, P. O., Luhr, M., Mills, I. G., Saetre, F., Szalai, P., and Engedal, N. (2015). Macroautophagic cargo sequestration assays. Methods 75, 25-36.

Soreng, K., Munson, M. J., Lamb, C. A., Bjorndal, G. T., Pankiv, S., Carlsson, S. R., Tooze, S. A., and Simonsen, A. (2018). SNX18 regulates ATG9A trafficking from recycling endosomes by recruiting Dynamin-2. EMBO Rep.

Steegmaier, M., Oorschot, V., Klumperman, J., and Scheller, R. H. (2000). Syntaxin 17 is abundant in steroidogenic cells and implicated in smooth endoplasmic reticulum membrane dynamics. Mol Biol Cell 11, 2719-2731.

Steegmaier, M., Yang, B., Yoo, J. S., Huang, B., Shen, M., Yu, S., Luo, Y., and Scheller, R. H. (1998). Three novel proteins of the syntaxin/SNAP-25 family. J Biol Chem 273, 34171-34179.

Suzuki, H., Kaizuka, T., Mizushima, N., and Noda, N. N. (2015). Structure of the Atg101-Atg13 complex reveals essential roles of Atg101 in autophagy initiation. Nat Struct Mol Biol 22, 572-580.

Szalai, P., Hagen, L. K., Saetre, F., Luhr, M., Sponheim, M., Overbye, A., Mills, I. G., Seglen, P. O., and Engedal, N. (2015). Autophagic bulk sequestration of cytosolic cargo is independent of LC3, but requires GABARAPs. Exp Cell Res 333, 21-38.

Takats, S., Glatz, G., Szenci, G., Boda, A., Horvath, G. V., Hegedus, K., Kovacs, A. L., and Juhasz, G. (2018). Non-canonical role of the SNARE protein Ykt6 in autophagosome-lysosome fusion. PLoS Genet 14, e1007359.

Takats, S., Nagy, P., Varga, A., Pires, K., Karpati, M., Varga, K., Kovacs, A. L., Hegedus, K., and Juhasz, G. (2013). Autophagosomal Syntaxin17-dependent lysosomal degradation maintains neuronal function in *Drosophila*. J Cell Biol 201, 531-539.

Thurston, T. L, Ryzhakov, G., Bloor, S., von Muhlinen, N., and Randow, F. (2009). The TBK1 adaptor and autophagy receptor NDP52 restricts the proliferation of ubiquitin coated bacteria. Nat Immunol 10, 1215-1221.

Wang, Z., Miao, G., Xue, X., Guo, X., Yuan, C., Wang, Z., Zhang, G., Chen, Y., Feng, D., Hu, J., et al. (2016). The Vici Syndrome Protein EPG5 Is a Rab7 Effector that Determines the Fusion Specificity of Autophagosomes with Late Endosomes/Lysosomes. Mol Cell 63, 781-795.

Wild, P., Farhan, H., McEwan, D. G., Wagner, S., Rogov, V. V., Brady, N. R., Richter, B., Korac, J., Waidmann, O., Choudhary, C., et al. (2011). Phosphorylation of the autophagy receptor optineurin restricts *Salmonella* growth. Science 333, 228-233.

Young, A. R., Chan, E. Y., Hu, X. W., Kochi, R., Crawshaw, S. G., High, S., Hailey, D. W., Lippincott-Schwartz, J., and Tooze, S. A. (2006). Starvation and ULK1-dependent cycling of mammalian Atg9 between the TGN and endosomes. J Cell Sci 119, 3888-3900.

The invention claimed is:

1. A method of therapeutically treating cancer in a patient in need, the method comprising administering to said patient an effective amount of a TBK-1 inhibitor and an inhibitor of Syntaxin 17 phosphorylation to said patient, wherein said TBK-1 inhibitor is BX795, MRT67307, B1-B206, D1-D100, F1-F-160, amlexanox or a mixture thereof and said inhibitor of Syntaxin 17 phosphorylation is Tyrphostin AG1478 and/or Tyrphostin AG1024.

2. The method according to claim 1 wherein said TBK-1 inhibitor and said inhibitor of Syntaxin 17 phosphorylation are co-administered with at least one additional bioactive agent.

3. The method according to claim 2 wherein said additional bioactive agent is an autophagy inhibitor, an autophagy agonist or an additional agent for treating cancer.

4. The method according to claim 3 wherein said additional bioactive agent is an additional autophagy inhibitor.

5. The method according to claim 4 wherein said additional autophagy inhibitor is tetrachlorisophthalonitrile, phenylmercuric acetate, JQ1, 2-methoxyestradiol, 3-methyladenine (3MA), epigallocatechin gallate (EGCG), 3BDO, 5-aminolevulinic acid, 5-azacytidine, 6-thioguanine, A-317491, A-867744, ABT-737, ABT-751, aceglutamide, acetazolamide, afatinib, capsaicin, actigenin, ascorbic acid, curcumin, resveratrol, SP600125, U0126, Baliomycin A1, chloroquine, LY294002, SB202190, SB203580, SC79, autophinib, wortmannin, crocin, harmines, mangiferin or a pharmaceutically acceptable salt thereof.

6. The method according to claim 2 wherein said additional bioactive agent is or includes an additional agent for treating cancer or an autoimmune disease.

7. The method according to claim 6 wherein said additional agent for treating cancer is an antimetabolite, an inhibitor of topoisomerase I and II, an alkylating agent, a microtubule inhibitor, a tyrosine kinase inhibitor, an EGF kinase inhibitor, a tyrosine kinase inhibitor, an ABL kinase inhibitor or mixtures thereof.

8. The method according to claim 6 wherein said additional agent for treating cancer is everolimus, trabectedin, nab-paclitaxel, ILK 286, AV-299, DN-101, pazopanib, GSK690693, RTA 744, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR, inhibitor, an EGER TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-EGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatinib, nilotinib, decatanib, panitumumab, amrubicin, oregovomab, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, PD0325901, capecitabine, L-Glutamic add, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714, TAK-165, HKI-272, erlotinib, lapatanib, canertinib, ABX EGF antibody, erbitux, EKB-569, PKI-166, GW-572016, Ionafarnib, BMS-214662, tipifarnib, amifostine, NVP-LAQ824, suberoyl analide hydroxamic acid, valproic acid, trichostatin A, FK-228, SU-11248, sorafenib, KRN951 aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, imatinib mesylate, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine cytosine arabinoside, 6-mecaptopurine, deoxycoformycin, calcitriol, valrubicin, mithramycin, vinblastine, vinorelbine, topotecan, razoxin, marimastat, COL 3, neovastat, BMS-275291 squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilimumab, pembrolizumab, nivolumab, alemtuzumab, atezolizumab, ofatumumab, novolumab, pembrolizumab, rituximab or a mixture thereof.

9. The method according claim 3 wherein said cancer is a carcinoma, a leukemia, a lymphoma, melanoma, a myeloproliferative disease, a sarcoma, a tumor of the central nervous system, a germ-line tumor, a mixed type of neoplasia or a tumor of mixed origin.

10. The method according to claim 6 wherein said autoimmune disease is rheumatoid arthritis, antiphospholipid antibody syndrome, lupus, chronic urticarial, Sjogren's disease, autoimmune-related Type 1 diabetes, rheumatoid arthritis (RA), psoriasis/psoriatic arthritis, multiple sclerosis, inflammatory bowel disease (IBD) including Crohn's disease and ulcerative colitis, Addison's disease, Grave's disease, Hashimoto's thyroiditis, Myasthenia gravis, autoimmune vasculitis, pernicious anemia or celiac disease.

11. The method according to claim 1 wherein said TBK1 inhibitor is BX795 or MRT67307.

12. The method according to claim 2 wherein said TBK1 inhibitor is BX795 or MRT67307.

13. The method according to claim 3 wherein said TBK1 inhibitor is BX795 or MRT67307.

14. The method according to claim 4 wherein said TBK1 inhibitor is BX795 or MRT67307.

15. The method according to claim 5 wherein said TBK1 inhibitor is BX795 or MRT67307.

16. The method according to claim 6 wherein said TBK1 inhibitor is BX795 or MRT67307.

17. The method according to claim 7 wherein said TBK1 inhibitor is BX795 or MRT67307.

18. The method according to claim 8 wherein said TBK1 inhibitor is BX795 or MRT67307.

19. The method according to claim 9 wherein said TBK1 inhibitor is BX795 or MRT67307.

20. The method according to claim 10 wherein said TBK1 inhibitor is BX795 or MRT67307.

* * * * *